(12) United States Patent
Cassayre et al.

(10) Patent No.: US 8,735,362 B2
(45) Date of Patent: May 27, 2014

(54) INSECTICIDAL COMPOUNDS BASED ON ISOXAZOLINE DERIVATIVES

(75) Inventors: Jerome Yves Cassayre, Stein (CH); Peter Renold, Stein (CH); Myriem El Qacemi, Stein (CH); Thomas Pitterna, Stein (CH); Julie Clementine Toueg, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 43 days.

(21) Appl. No.: 13/512,820

(22) PCT Filed: Dec. 1, 2010

(86) PCT No.: PCT/EP2010/068605
§ 371 (c)(1),
(2), (4) Date: May 30, 2012

(87) PCT Pub. No.: WO2011/067272
PCT Pub. Date: Jun. 9, 2011

(65) Prior Publication Data
US 2012/0238517 A1    Sep. 20, 2012

(30) Foreign Application Priority Data

Dec. 1, 2009    (EP) .................................... 09177640
Oct. 5, 2010    (EP) .................................... 10186537

(51) Int. Cl.
| | | |
|---|---|---|
| *A01N 43/80* | (2006.01) |
| *A01N 43/90* | (2006.01) |
| *A01N 53/08* | (2006.01) |
| *A01P 7/04* | (2006.01) |
| *C07D 413/14* | (2006.01) |
| *C07D 417/12* | (2006.01) |
| *C07D 419/12* | (2006.01) |

(52) U.S. Cl.
USPC .......... 514/30; 514/202; 514/226.5; 514/250; 514/314; 514/340; 514/360; 514/372; 514/378; 546/167; 546/272.1; 548/122; 548/214; 548/240; 548/243; 548/245

(58) Field of Classification Search
None
See application file for complete search history.

(56) References Cited

U.S. PATENT DOCUMENTS

2009/0156643 A1    6/2009   Mita et al.

FOREIGN PATENT DOCUMENTS

| EP | 1731512 | 12/2006 |
|---|---|---|
| EP | 1932836 | 6/2008 |
| EP | 1 997 813 A1 | 12/2008 |
| EP | 2 151 437 A1 | 2/2010 |
| EP | 2186804 A1 | 5/2010 |
| EP | 2199287 A1 | 6/2010 |
| EP | 2 412 239 A1 | 7/2011 |
| EP | 2 412 240 A1 | 7/2011 |
| EP | 2 412 241 A1 | 7/2011 |
| EP | 2 412 238 A1 | 2/2012 |
| JP | 2007-16017 | 1/2007 |
| JP | 2007-91708 | 4/2007 |
| JP | 2007-106756 | 4/2007 |
| JP | 2008-110971 | 5/2008 |
| JP | 2008-133273 | 6/2008 |
| JP | 2008-239611 | 10/2008 |
| JP | 2009-108046 | 5/2009 |
| JP | 2010-83883 | 4/2010 |
| JP | 2010-235590 | 10/2010 |
| JP | 2010-254629 | 11/2010 |
| JP | 2011-37817 | 2/2011 |
| JP | 2011-178673 | 9/2011 |
| JP | 2012-31093 | 2/2012 |
| JP | 2012-31094 | 2/2012 |
| JP | 2012-31095 | 2/2012 |
| JP | 2012-31148 | 2/2012 |
| JP | 2012-51843 | 3/2012 |
| WO | 2007/070606 A2 | 6/2007 |
| WO | 2007/075459 A2 | 7/2007 |
| WO | 2007/079162 A1 | 7/2007 |
| WO | 2007/123853 A2 | 11/2007 |
| WO | 2007/123855 A2 | 11/2007 |
| WO | 2007/125984 A1 | 11/2007 |
| WO | 2008/019760 A1 | 2/2008 |
| WO | 2008/126665 A2 | 3/2008 |
| WO | 2008/122375 A2 | 10/2008 |
| WO | 2008/128711 A1 | 10/2008 |
| WO | 2008/130651 A2 | 10/2008 |
| WO | 2008/150393 A1 | 12/2008 |
| WO | 2008/154528 A2 | 12/2008 |

(Continued)

OTHER PUBLICATIONS

Ozoe et al., Biochemical and Biophysical Research Communications, 391, 2010, 744-749.

*Primary Examiner* — Kamal Saeed
(74) *Attorney, Agent, or Firm* — R. Kody Jones

(57) ABSTRACT

The present invention relates to compounds of formula (I): Wherein $A^1, A^2, A^3, A^4, G^1, L, Y^1, Y^2, Y^3, Y^4, R^1, R^2, R^3$ and $R^4$ are as defined in claim 1; or a salt or N-oxide thereof. Furthermore, the present invention relates to intermediates for preparing compounds of formula (I), to compositions comprising them and to methods of using them to combat and control insect, acarine, nematode and mollusc pests.

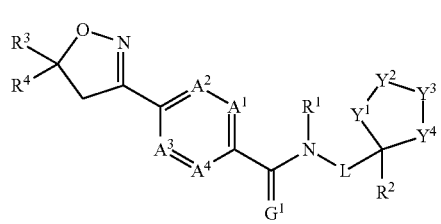

(I)

15 Claims, No Drawings

(56) References Cited

FOREIGN PATENT DOCUMENTS

| | | |
|---|---|---|
| WO | 2009/002809 A2 | 12/2008 |
| WO | 2009/003075 A1 | 12/2008 |
| WO | 2009/024541 A2 | 2/2009 |
| WO | 2009/045999 A1 | 4/2009 |
| WO | 2009/049846 A1 | 4/2009 |
| WO | 2009/051956 A2 | 4/2009 |
| WO | 2009/072621 A1 | 6/2009 |
| WO | 2009/077197 A1 | 6/2009 |
| WO | 2009/080250 | 7/2009 |
| WO | 2009/097992 A1 | 8/2009 |
| WO | 2009/112275 A1 | 9/2009 |
| WO | 2009/141096 A1 | 11/2009 |
| WO | 2010/003877 A1 | 1/2010 |
| WO | 2010/003923 A1 | 1/2010 |
| WO | 2010/020521 A1 | 2/2010 |
| WO | 2010/020522 A1 | 2/2010 |
| WO | 2010/025998 A1 | 3/2010 |
| WO | 2010/032437 A1 | 3/2010 |
| WO | 2010/043315 A1 | 4/2010 |
| WO | 2010/070068 A2 | 6/2010 |
| WO | 2010/072602 A2 | 7/2010 |
| WO | 2010/072781 A2 | 7/2010 |
| WO | 2010/079077 A1 | 7/2010 |
| WO | 2010/084067 A2 | 7/2010 |
| WO | 2010/086225 | 8/2010 |
| WO | 2010/086225 A1 | 8/2010 |
| WO | 2010/108733 A1 | 9/2010 |
| WO | 2010/112545 A1 | 10/2010 |
| WO | 2010/124845 A1 | 11/2010 |
| WO | 2010/133336 A1 | 11/2010 |
| WO | 2010/149506 A1 | 12/2010 |
| WO | 2011/051455 A1 | 5/2011 |
| WO | 2011/054871 A1 | 5/2011 |
| WO | 2011/073444 A2 | 6/2011 |
| WO | 2011/075591 A1 | 6/2011 |
| WO | 2011/092287 A1 | 8/2011 |
| WO | 2011/101229 A1 | 8/2011 |
| WO | 2011/101402 A1 | 8/2011 |
| WO | 2011/104087 A1 | 9/2011 |
| WO | 2011/104088 A1 | 9/2011 |
| WO | 2011/104089 A1 | 9/2011 |
| WO | 2011/124998 A1 | 10/2011 |
| WO | 2011/128299 A1 | 10/2011 |
| WO | 2011/149749 A1 | 12/2011 |
| WO | 2011/154433 A2 | 12/2011 |
| WO | 2011/154434 A2 | 12/2011 |
| WO | 2011/154494 A2 | 12/2011 |
| WO | 2011/157733 A2 | 12/2011 |
| WO | 2011/157748 A1 | 12/2011 |
| WO | 2012/004326 A1 | 1/2012 |
| WO | 2012/007426 A1 | 1/2012 |
| WO | 2012/017359 A1 | 2/2012 |
| WO | 2012/026403 A1 | 3/2012 |
| WO | 2012/034957 A1 | 3/2012 |
| WO | 2012/035011 A1 | 3/2012 |
| WO | 2012/038851 A1 | 3/2012 |
| WO | 2012/045700 A1 | 4/2012 |
| WO | 2012/049327 A2 | 4/2012 |
| WO | 2012/060317 A1 | 5/2012 |
| WO | 2012/067235 A1 | 5/2012 |

INSECTICIDAL COMPOUNDS BASED ON ISOXAZOLINE DERIVATIVES

This application is a 371 of International Application No. PCT/EP2010/068605 filed Dec. 1, 2010, which claims priority to EP 09177640.1 filed Dec. 1, 2009, and EP 10186537.6 filed Oct. 5, 2012, the contents of which are incorporated herein by reference.

The present invention relates to certain benzamide isoxazolines, to processes and intermediates for preparing them, to insecticidal, acaricidal, nematicidal and molluscicidal compositions comprising them and to methods of using them to combat and control insect, acarine, nematode and mollusc pests.

Certain isoxazoline derivatives with insecticidal properties are disclosed, for example, in EP 1,731,512, US 2007/066617, JP 2007/008914, JP 2007/016017, WO 07/026,965, JP 2007/106756, WO 07/070,606, WO 07/074,789 and WO 07/075,459.

It has now surprisingly been found that certain novel isoxazolines have insecticidal properties.

The present invention therefore provides a compound of formula (I):

wherein
$A^1$, $A^2$, $A^3$ and $A^4$ are independently of one another C—H, C—$R^5$, or nitrogen;
$G^1$ is oxygen or sulfur;
L is a single bond or $C_1$-$C_8$alkylene;
$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl, or $C_1$-$C_8$alkoxycarbonyl-;
$R^2$ is hydrogen, $C_1$-$C_8$haloalkyl or $C_1$-$C_8$alkyl;
$R^3$ is $C_1$-$C_8$haloalkyl;
$R^4$ is aryl or aryl substituted by one to three $R^6$, or $R^4$ is heterocyclyl or heterocyclyl substituted by one to three $R^6$;
each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH=CH—CH=CH— bridge or a —N=CH—CH=CH— bridge;
each $R^6$ is independently halogen, cyano, nitro, $C_1$-$C_8$alkyl, $C_1$-$C_8$haloalkyl, $C_1$-$C_8$alkoxy, or $C_1$-$C_8$-haloalkoxy;
$Y^1$ is $CR^7R^8$ or C=O;
$Y^2$, $Y^3$ and $Y^4$ are independently $CR^7R^8$, C=O, N—$R^9$, O, S, SO or $SO_2$;
wherein at least two adjacent ring atoms in the ring formed by $Y^1$, $Y^2$, $Y^3$ and $Y^4$ are heteroatoms;
each $R^7$ and $R^8$ is independently hydrogen, halogen, $C_1$-$C_8$alkyl, or $C_1$-$C_8$haloalkyl;
each $R^9$ is independently hydrogen, cyano, cyano-$C_1$-$C_8$alkyl, $C_1$-$C_8$ alkyl, $C_1$-$C_8$ haloalkyl, $C_3$-$C_8$cycloalkyl, $C_3$-$C_8$cycloalkyl where one carbon atom is replaced by O, S, S(O) or $SO_2$, or $C_3$-$C_8$ cycloalkyl-$C_1$-$C_8$ alkyl, $C_3$-$C_8$ cycloalkyl-$C_1$-$C_8$ alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$ hydroxyalkyl, $C_1$-$C_8$ alkoxy-$C_1$-$C_8$ alkyl, $C_2$-$C_8$alkenyl, $C_2$-$C_8$ haloalkenyl, $C_2$-$C_8$ alkynyl, $C_2$-$C_8$haloalkynyl, phenyl, phenyl substituted by one to three $R^{10}$, phenyl-$C_1$-$C_4$alkyl, phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$, or
$C_1$-$C_4$ alkyl-($C_1$-$C_4$ alkyl-O—N=)C—$CH_2$—;
each $R^{10}$ is independently halogen, cyano, nitro, $C_1$-$C_8$ alkyl, $C_1$-$C_8$ haloalkyl, $C_1$-$C_8$ alkoxy, or $C_1$-$C_8$ haloalkoxy;
or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, in the —$CR^3R^4$— group or at the L$R^2Y^1Y^4$ carbon and may exist as enantiomers (or as pairs of diastereoisomers) or as mixtures of such. Further, where any Y group is SO, the compounds of the invention are sulfoxides, which can also exist in two enantiomeric forms.

Each alkyl moiety either alone or as part of a larger group (such as alkoxy, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$-$C_6$ alkyl groups, more preferably $C_1$-$C_4$ and most preferably $C_1$-$C_3$ alkyl groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl moieties can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Halogen is fluorine, chlorine, bromine or iodine.

Haloalkyl groups (either alone or as part of a larger group, such as haloalkoxy) are alkyl groups which are substituted by one or more of the same or different halogen atoms and are, for example, trifluoromethyl, chlorodifluoromethyl, 2,2,2-trifluoro-ethyl or 2,2-difluoro-ethyl.

Haloalkenyl groups are alkenyl groups, respectively, which are substituted with one or more of the same or different halogen atoms and are, for example, 2,2-difluorovinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of (5-6 membered) monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably monocyclic rings containing 1 to 3 heterotoms selected from O, N or S, e.g. pyridyl, pyridazinyl, pyrimidinyl, pyrazinyl, pyrazolyl, furanyl, thiophenyl, oxazolyl, isoxazolyl, thiazolyl, preferably pyridyl, pyrazolyl, furanyl, thiophenyl, thiazolyl, pyridyl being most preferred.

The term "heterocyclyl" is defined to include heteroaryl and in addition their unsaturated or partially unsaturated analogues.

Preferred values of $A^1$, $A^2$, $A^3$, $A^4$, $G^1$, L, $R^1$, $R^2$, $R^3$, $R^4$, $Y^1$, $Y^2$, $Y^3$, $Y^4$, $R^5$, $R^6$, $R^7$, $R^8$, $R^9$ and $R^{10}$, are, in any combination, as set out below.

Preferably no more than two of $A^1$, $A^2$, $A^3$ and $A^4$ are nitrogen.

Preferably $A^1$ is C—H or C—$R^5$, most preferably $A^1$ is C—$R^5$.

Preferably $A^2$ is C—H or C—$R^5$, most preferably $A^2$ is C—H.

Preferably $A^3$ is C—H or N, most preferably $A^3$ is C—H.
Preferably $A^4$ is C—H or N, most preferably $A^4$ is C—H.
Preferably $G^1$ is oxygen.

Preferably L is a single bond or $C_1$-$C_4$alkylene. More preferably L is a single bond or $CH_2$, most preferably a single bond.

Preferably $R^1$ is hydrogen, methyl, ethyl, methylcarbonyl-, or methoxycarbonyl-, more preferably hydrogen, methyl or ethyl, even more preferably hydrogen or methyl, most preferably hydrogen.

Preferably $R^2$ is hydrogen or methyl, most preferably hydrogen.

Preferably $R^3$ is chlorodifluoromethyl or trifluoromethyl, most preferably trifluoromethyl.

Preferably $R^4$ is aryl or aryl substituted by one to three $R^6$, more preferably $R^4$ is phenyl or phenyl substituted by one to three $R^6$, even more preferably $R^4$ is phenyl substituted by one to three $R^6$, more preferably $R^4$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichloro-phenyl, 4-fluoro-3,5-dichloro-phenyl or 3,4,5-trichloro-phenyl, yet even more preferably $R^4$ is 3,5-dibromo-phenyl, 3,5-dichloro-phenyl, 3,5-bis-(trifluoromethyl)-phenyl, 4-bromo-3,5-dichlorophenyl, or 3,4,5-trichloro-phenyl, most preferably $R^4$ is 3,5-dichlorophenyl.

Preferably each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, or two $R^5$ on adjacent carbon atoms together form a —CH=CH—CH=CH— bridge, more preferably halogen, cyano, nitro, $C_1$-$C_8$alkyl, $C_2$-$C_8$alkenyl, $C_3$-$C_8$cycloalkyl, $C_1$-$C_8$haloalkyl, even more preferably bromo, chloro, fluoro, cyano, nitro, methyl, ethyl, trifluoromethyl, cyclopropyl, vinyl, yet even more preferably bromo, chloro, fluoro, cyclopropyl, trifluoromethyl, vinyl, or methyl, most preferably chloro, fluoro, or methyl.

Preferably each $R^6$ is independently bromo, chloro, fluoro, cyano, nitro, methyl, ethyl, trifluoromethyl, methoxy, difluoromethoxy, trifluoromethoxy, more preferably chloro, fluoro, cyano, nitro, methyl, ethyl, trifluoromethyl, methoxy, or trifluoromethoxy, most preferably bromo, chloro, or trifluoromethyl.

Preferably $Y^1$ is $CR^7R^8$.

Preferably two of $Y^2$, $Y^3$ and $Y^4$ in the grouping —$Y^2$—$Y^3$—$Y^4$— together are —S—S—, —S—SO—, —SO—SO—, —SO—$SO_2$—, —$SO_2$—$SO_2$—, —O—N(—$R^9$)—, —O—S—, —O—SO—, —O—$SO_2$—, —N(—$R^9$)—N(—$R^9$)—, —N(—$R^9$)—S—, —N(—$R^9$)—S(O)—, or —N(—$R^9$)—$SO_2$—, more preferably —S—S—, —O—N(—$R^9$)—, —O—SO—, —N(—$R^9$)—N(—$R^9$)—, —N(—$R^9$)—S, —N(—$R^9$)—S(O)— or —N(—$R^9$)—$SO_2$.

The grouping —$Y^2$—$Y^3$—$Y^4$— may be selected from —C($R^7$)($R^8$)—N(—$R^9$)—N(—$R^9$)—, —C($R^7$)($R^8$)—N(—$R^9$)—O—, —C($R^7$)($R^8$)—N(—$R^9$)—S—, —C($R^7$)($R^8$)—N(—$R^9$)—SO—, —C($R^7$)($R^8$)—N(—$R^9$)—$SO_2$—, —C($R^7$)($R^8$)—O—N(—$R^9$)—, —C($R^7$)($R^8$)—O—S—, —C($R^7$)($R^8$)—O—SO—, —C($R^7$)($R^8$)—O—$SO_2$—, —C($R^7$)($R^8$)—S—N(—$R^9$)—, —C($R^7$)($R^8$)—S—O—, —C($R^7$)($R^8$)—S—S—, —C($R^7$)($R^8$)—S—SO—, —C(R)($R^8$)—S—$SO_2$—, —C($R^7$)($R^8$)—SO—N(—$R^9$)—, —C($R^7$)($R^8$)—SO—O—, —C($R^7$)($R^8$)—SO—S—, —C(R)($R^8$)—SO—SO—, —C($R^7$)($R^8$)—SO—$SO_2$—, —C($R^7$)($R^8$)—$SO_2$-M-$R^9$)—, —C($R^7$)($R^8$)—$SO_2$—O—, —C($R^7$)($R^8$)—$SO_2$—S—, —C($R^7$)($R^8$)—$SO_2$—SO—, —C($R^7$)($R^8$)—$SO_2$—$SO_2$—, —C(=O)—N(—$R^9$)—N(—$R^9$)—, —C(=O)—N(—$R^9$)—O—, —C(=O)—N(—$R^9$)—S—, —C(=O)—N(—$R^9$)—SO—, —C(=O)—N(—$R^9$)—$SO_2$—, —C(=O)—O—N(—$R^9$)—, —C(=O)—O—S—, —C(=O)—O—SO—, —C(=O)—O—$SO_2$—, —C(=O)—S—N(—$R^9$)—, —C(=O)—S—O—, —C(=O)—S—S—, —C(=O)—S—SO—, —C(=O)—S—$SO_2$—, —N(—$R^9$)—N(—$R^9$)—C($R^7$)($R^8$), —N(—$R^9$)—N(—$R^9$)—C(=O), —N(—$R^9$)—N(—$R^9$)—S—, —N(—$R^9$)—N(—$R^9$)—SO—, —N(—$R^9$)—N(—$R^9$)—$SO_2$—, —N(—$R^9$)—O—C($R^7$)($R^8$), —N(—$R^9$)—O—C(=O)—, —N(—$R^9$)—O—N(—$R^9$)—, —N(—$R^9$)—O—S—, —N(—$R^9$)—O—SO—, —N(—$R^9$)—O—$SO_2$—, —N(—$R^9$)—S—C($R^7$)($R^8$), —N(—$R^9$)—S—C(=O)—, —N(—$R^9$)—S—N(—$R^9$)—, —N(—$R^9$)—S—O—, —N(—$R^9$)—S—S—, —N(—$R^9$)—S—SO—, —N(—$R^9$)—S—$SO_2$—, —N(—$R^9$)—SO—C($R^7$)($R^8$), —N(—$R^9$)—SO—N(—$R^9$)—, —N(—$R^9$)—SO—O—, —N(—$R^9$)—SO—S—, —N(—$R^9$)—$SO_2$—C($R^7$)($R^8$), —N(—$R^9$)—$SO_2$—N(—$R^9$)—, —N(—$R^9$)—$SO_2$—O—, —N(—$R^9$)—$SO_2$—S—, —O—N(—$R^9$)—C($R^7$)($R^8$)—, —O—N(—$R^9$)—C(=O)—, —O—N(—$R^9$)—S—, —O—N(—$R^9$)—SO—, —O—N(—$R^9$)—$SO_2$—, —N(—$R^9$)—O—S—, —N(—$R^9$)—O—SO—, —N(—$R^9$)—O—$SO_2$—, —N(—$R^9$)—S—C($R^7$)($R^8$)—, —N(—$R^9$)—S—C(=O)—, —N(—$R^9$)—S—N(—$R^9$)—, —N(—$R^9$)—S—O—, —N(—$R^9$)—S—S—, —N(—$R^9$)—S—SO—, —N(—$R^9$)—S—$SO_2$—, —N(—$R^9$)—SO—C($R^7$)($R^8$)—, —N(—$R^9$)—SO—N(—$R^9$)—, —N(—$R^9$)—SO—O—, —N(—$R^9$)—SO—S—, —N(—$R^9$)—$SO_2$—C($R^7$)($R^8$)—, —N(—$R^9$)—$SO_2$—N(—$R^9$)—, —N(—$R^9$)—$SO_2$—O—, —N(—$R^9$)—$SO_2$—S—, —S—N(—$R^9$)—C($R^7$)($R^8$)—, —S—N(—$R^9$)—C(=O)—, —S—N(—$R^9$)—N(—$R^9$)—, —S—N(—$R^9$)—O—, —S—N(—$R^9$)—S—, —S—N(—$R^9$)—SO—, —S—N(—$R^9$)—$SO_2$—, —S—O—C($R^7$)($R^8$)—, —S—O—C(=O)—, —S—O—N(—$R^9$)—, —S—S—C($R^7$)($R^8$)—, —S—S—C(=O)—, —S—S—S—, —S—SO—C($R^7$)($R^8$)—, —S—SO—C(=O)—, —S—$SO_2$—C($R^7$)($R^8$)—, —S—$SO_2$—C(=O)—, —SO—N(—$R^9$)—C($R^7$)($R^8$)—, —SO—N(—$R^9$)—C(=O)—, —SO—N(—$R^9$)—N(—$R^9$)—, —SO—N(—$R^9$)—O—, —SO—N(—$R^9$)—S—, —SO—N(—$R^9$)—SO—, —SO—O—C($R^7$)($R^8$), —SO—O—C(=O)—, —SO—S—C($R^7$)($R^8$)—, —SO—S—C(=O)—, —SO—S—N(—$R^9$)—, —$SO_2$—N(—$R^9$)—C($R^7$)($R^8$)—, —$SO_2$—

N(—$R^9$)—C(=O)—, —$SO_2$—N(—$R^9$)—N(—$R^9$)—, —$SO_2$—N(—$R^9$)—O—, —$SO_2$—N(—$R^9$)—S—, —$SO_2$—N(—$R^9$)—$SO_2$—, —$SO_2$—O—C($R^7$)($R^8$)— and —$SO_2$—O—C(=O)—.

Preferably the grouping —$Y^2$—$Y^3$—$Y^4$— is selected from —C($R^7$)($R^8$)—N(—$R^9$)—N(—$R^9$)—, —C($R^7$)($R^8$)—N(—$R^9$)—O—, —C($R^7$)($R^8$)—N(—$R^9$)—S—, —C($R^7$)($R^8$)—N(—$R^9$)—$SO_2$—, —C($R^7$)($R^8$)—O—N(—$R^9$)—, —C($R^7$)($R^8$)—O—SO—, —C($R^7$)($R^8$)—O—$SO_2$—, —C($R^7$)($R^8$)—S—N(—$R^9$)—, —C($R^7$)($R^8$)—S—S—, —C($R^7$)($R^8$)—SO—O—, —C($R^7$)($R^8$)—$SO_2$—N(—$R^9$)—, —C($R^7$)($R^8$)—$SO_2$—O—, —C(=O)—N(—$R^9$)—N(—$R^9$)—, —C(=O)—N(—$R^9$)—O—, —C(=O)—N(—$R^9$)—S—, —C(=O)—O—N(—$R^9$)—, —C(=O)—S—N(—$R^9$)—, —N(—$R^9$)—N(—$R^9$)—C($R^7$)($R^8$)—, —N(—$R^9$)—N(—$R^9$)—C(=O)—, —N(—$R^9$)—O—C($R^7$)($R^8$)—, —N(—$R^9$)—O—C(=O)—, —N(—$R^9$)—S—C($R^7$)($R^8$)—, —N(—$R^9$)—SO—N(—$R^9$)—, —N(—$R^9$)—$SO_2$—C($R^7$)($R^8$)—, —N(—$R^9$)—$SO_2$—N(—$R^9$)—, —N(—$R^9$)—$SO_2$—O—, —O—N(—$R^9$)—C($R^7$)($R^8$)—, —O—N(—$R^9$)—C(=O)—, —O—N(—$R^9$)—SO—, —O—N(—$R^9$)—$SO_2$—, —N(—$R^9$)—S—C($R^7$)($R^8$)—, —N(—$R^9$)—SO—C($R^7$)($R^8$)—, —N(—$R^9$)—SO—N(—$R^9$)—, —N(—$R^9$)—SO—O—, —N(—$R^9$)—$SO_2$—C($R^7$)($R^8$)—, —N(—$R^9$)—$SO_2$—N(—$R^9$)—, —N(—$R^9$)—$SO_2$—O—, —S—N(—$R^9$)—$SO_2$—O—, —S—N(—$R^9$)—C($R^7$)($R^8$), —S—N(—$R^9$)—C(=O)—, —S—S—C($R^7$)($R^8$)—, —SO—N(—$R^9$)—N(—$R^9$)—, —SO—O—C($R^7$)($R^8$)—, —$SO_2$—N(—$R^9$)—C($R^7$)($R^8$)—, —$SO_2$—N(—$R^9$)—N(—$R^9$)—, —$SO_2$—N(—$R^9$)—O— and —$SO_2$—O—C($R^7$)($R^8$)—. More preferably the grouping —$Y^2$—$Y^3$—$Y^4$— is selected from —O—N(—$R^9$)—C(=O)—, —S—S—C($R^7$)($R^8$)—, —S—SO—C($R^7$)($R^8$)—, —O—N(—$R^9$)—($R^7$)($R^8$)—, —N(—$R^9$)—N(—$R^9$)—C(=O)—, —$SO_2$—N(—$R^9$)—C($R^7$)($R^8$)—, —C($R^7$)($R^8$)—N(—$R^9$)—O—, —C($R^7$)($R^8$)—N(—$R^9$)—O—, —C(=O)—N(—$R^9$)—O—, —C(=O)—N($R^9$)—O—, —O—SO—O—, —C($R^7$)($R^8$)—N(—$R^9$)—$SO_2$, —N(—$R^9$)—$SO_2$—O—, —SO—O—C($R^7$)($R^8$)— and —N(—$R^9$)—SO—O—, even more preferably from —O—N(—$R^9$)—C(=O)—, —S—S—C($R^7$)($R^8$)—, —$SO_2$—N(—$R^9$)—C($R^7$)($R^8$)—, —C($R^7$)($R^8$)—N(—$R^9$)—O—, —C(=O)—N(—$R^9$)—O—, —SO—O—C($R^7$)($R^8$)— and —C(=O)—N(—$R^9$)—O—, even more preferably —O—N(—$R^9$)—C(=O)— and —SO—O—C($R^7$)($R^8$)—.

In one embodiment $Y^2$ or $Y^4$ is $CR^7R^8$ or C=O. According to this embodiment the grouping —$Y^2$—$Y^3$—$Y^4$— is preferably selected from —C($R^7$)($R^8$)—N(—$R^9$)—N(—$R^9$)—, —C($R^7$)($R^8$)—N(—$R^9$)—O—, —C($R^7$)($R^8$)—N(—$R^9$)—S—, —C($R^7$)($R^8$)—N(—$R^9$)—$SO_2$—, —C($R^7$)($R^8$)—O—N(—$R^9$)—, —C($R^7$)($R^8$)—O—SO—, —C(R)($R^8$)—O—$SO_2$—, —C($R^7$)($R^8$)—S—N(—$R^9$)—, —C($R^7$)($R^8$)—S—S—, —C($R^7$)($R^8$)—SO—O—, —C($R^7$)($R^8$)—$SO_2$—N(—$R^9$)—, —C($R^7$)($R^8$)—$SO_2$—O—, —C(=O)—N(—$R^9$)—N(—$R^9$)—, —C(=O)—N(—$R^9$)—O—, —C(=O)—N(—$R^9$)—S—, —C(=O)—O—N(—$R^9$)—, —C(=O)—S—N(—$R^9$)—, —N(—$R^9$)—N(—$R^9$)—C($R^7$)($R^8$)—, —N(—$R^9$)—N(—$R^9$)—C(=O)—, —N(—$R^9$)—O—C($R^7$)($R^8$)—, —N(—$R^9$)—O—C(=O)—, —N(—$R^9$)—S—C($R^7$)($R^8$)—, —N(—$R^9$)—$SO_2$—C($R^7$)($R^8$)—, —O—N(—$R^9$)—C($R^7$)($R^8$)—, —O—N(—$R^9$)—C(=O)—, —N(—$R^9$)—S—C($R^7$)($R^8$)—, —N(—$R^9$)—SO—C($R^7$)($R^8$)—, —N(—$R^9$)—$SO_2$—C($R^7$)($R^8$)—, —S—N(—$R^9$)—C($R^7$)($R^8$), —S—N(—$R^9$)—C(=O), —S—S—C($R^7$)($R^8$)—, —SO—O—C($R^7$)($R^8$)—, —$SO_2$—N(—$R^9$)—C($R^7$)($R^8$)—, and —$SO_2$—O—C($R^7$)($R^8$)—. More preferably the grouping —$Y^2$—$Y^3$—$Y^4$— is selected from —S—S—C($R^7$)($R^8$)—, —O—N(—$R^9$)—C(=O)—, —C(=O)—N(—$R^9$)—O—, —C(R^7$)($R^8$)—N(—$R^9$)—O—, —SO—O—C($R^7$)($R^8$)—, and —C($R^7$)($R^8$)—N(—$R^9$)—O—.

($R^8$)—N(—$R^9$)—O—, —C($R^7$)($R^8$)—S—S—, —O—N(—$R^9$)—C($R^7$)($R^8$)—, —N(—$R^9$)—O—C($R^7$)($R^8$)—, —SO—O—C($R^7$)($R^8$)— and —C($R^7$)($R^8$)—N(—$R^9$)—O—. More preferably the grouping —$Y^2$—$Y^3$—$Y^4$— is selected from —S—S—C($R^7$)($R^8$)—, —O—N(—$R^9$)—C(=O)—, —C(=O)—N(—$R^9$)—O—, —SO—O—C($R^7$)($R^8$)— and —C($R^7$)($R^8$)—N(—$R^9$)—O—. More preferably the grouping —$Y^2$—$Y^3$—$Y^4$— is —O—N(—$R^9$)—C(=O)— or —SO—O—C($R^7$)($R^8$)—.

In one embodiment $Y^2$ or $Y^4$ is C=O. According to this embodiment the grouping —$Y^2$—$Y^3$—$Y^4$— is preferably selected from —C(=O)—N(—$R^9$)—N(—$R^9$)—, —C(=O)—N(—$R^9$)—O—, —C(=O)—N(—$R^9$)—S—, —C(=O)—O—N(—$R^9$)—, —C(=O)—S—N(—$R^9$)—, —N(—$R^9$)—N(—$R^9$)—C(=O)—, —N(—$R^9$)—O—C(=O)—, —O—N(—$R^9$)—C(=O)— and —S—N(—$R^9$)—C(=O). More preferably the grouping —$Y^2$—$Y^3$—$Y^4$— is selected from —O—N(—$R^9$)—C(=O)— and —C(=O)—N(—$R^9$)—O—.

In one embodiment $Y^2$ or $Y^4$ is $CR^7R^8$. According to this embodiment the grouping —$Y^2$—$Y^3$—$Y^4$— is preferably selected from —C($R^7$)($R^8$)—N(—$R^9$)—N(—$R^9$)—, —C($R^7$)($R^8$)—N(—$R^9$)—O—, —C($R^7$)($R^8$)—N(—$R^9$)—S—, —C($R^7$)($R^8$)—N(—$R^9$)—$SO_2$—, —C($R^7$)($R^8$)—O—N(—$R^9$)—, —C($R^7$)($R^8$)—O—SO—, —C($R^7$)($R^8$)—O—$SO_2$—, —C($R^7$)($R^8$)—S—N(—$R^9$)—, —C($R^7$)($R^8$)—S—S—, —C($R^7$)($R^8$)—SO—O—, —C($R^7$)($R^8$)—$SO_2$—N(—$R^9$)—, —C($R^7$)($R^8$)—$SO_2$—O—, —N(—$R^9$)—N(—$R^9$)—C($R^7$)($R^8$)—, —N(—$R^9$)—O—C($R^7$)($R^8$)—, —N(—$R^9$)—S—C($R^7$)($R^8$)—, —N(—$R^9$)—$SO_2$—C($R^7$)($R^8$)—, —O—N(—$R^9$)—C($R^7$)($R^8$)—, —N(—$R^9$)—S—C($R^7$) ($R^8$)—, —N(—$R^9$)—SO—C($R^7$)($R^8$)—, —N(—$R^9$)—$SO_2$—C($R^7$)($R^8$)—, —S—N(—$R^9$)—C($R^7$)($R^8$), —S—S—C($R^7$)($R^8$)—, —SO—O—C($R^7$)($R^8$)—, —$SO_2$—N(—$R^9$)—C($R^7$)($R^8$)— and —$SO_2$—O—C($R^7$)($R^8$)—. More preferably the grouping —$Y^2$—$Y^3$—$Y^4$— is selected from —S—S—C($R^7$)($R^8$)—, —C($R^7$)($R^8$)—N(—$R^9$)—O—, —C($R^7$)($R^8$)—S—S—, —O—N(—$R^9$)—C($R^7$)($R^8$)—, —N(—$R^9$)—O—C($R^7$)($R^8$)—, —SO—O—C($R^7$)($R^8$)— and —C($R^7$)($R^8$)—N(—$R^9$)—O—. More preferably the grouping $Y^2$—$Y^3$—$Y^4$— is selected from —S—S—C($R^7$)($R^8$)—, —SO—O—C($R^7$)($R^8$)— and —C($R^7$)($R^8$)—N(—$R^9$)—.

In one embodiment $Y^2$ and $Y^4$ are independently N—$R^9$, O, S, SO or $SO_2$. According to this embodiment the grouping —$Y^2$—$Y^3$—$Y^4$— is preferably selected from —N(—$R^9$)—SO—N(—$R^9$)—, —N(—$R^9$)—$SO_2$—N(—$R^9$)—, —N(—$R^9$)—$SO_2$—O—, —O—N(—$R^9$)—SO—, —O—N(—$R^9$)—$SO_2$—, —N(—$R^9$)—SO—N(—$R^9$)—, —N(—$R^9$)—SO—O—, —N(—$R^9$)—$SO_2$—N(—$R^9$)—, —N(—$R^9$)—$SO_2$—O—, —SO—N(—$R^9$)—N(—$R^9$)—, —$SO_2$—N(—$R^9$)—N(—$R^9$)— and —$SO_2$—N(—$R^9$)—O—. More preferably the grouping $Y^2$—$Y^3$—$Y^4$— is selected from —N(—$R^9$)—$SO_2$—O—, —O—$SO_2$—O—, —N(—$R^9$)—$SO_2$—N(—$R^9$)—, —O—$SO_2$—N(—$R^9$)— and —N(—$R^9$)—$SO_2$—O—. More preferably the grouping —$Y^2$—$Y^3$—$Y^4$— is selected from —N(—$R^9$)—$SO_2$—O—, —O—$SO_2$—O—, —N(—$R^9$)—$SO_2$—N(—$R^9$)—, and —O—$SO_2$—N(—$R^9$)—.

In one embodiment $Y^1$ is $CR^7R^8$ or C=O; $Y^2$ and $Y^3$ are independently $CR^7R^8$, C=O, N—$R^9$, O, S, SO or $SO_2$; $Y^4$ is $CR^7R^8$, C=O, SO or $SO_2$. Preferably $Y^2$ and $Y^3$ are independently N—$R^9$, O, S, SO, $SO_2$. Preferably $Y^2$ and $Y^3$ are independently N—$R^9$, O or S. Preferably $Y^2$ is O or S. More preferably $Y^2$ is O. Preferably $Y^3$ is N—$R^9$. Preferably $Y^4$ is C=O. Preferably $Y^3$ is N—$R^9$ and $Y^4$ is C=O. Preferably $Y^2$ is O, $Y^3$ is N—$R^9$ and $Y^4$ is C=O. Preferably $Y^1$ is $CR^7R^8$, $Y^2$ is O, $Y^3$ is N—$R^9$ and $Y^4$ is C=O.

In one embodiment $Y^1$ is $CR^7R^8$, $Y^2$ and $Y^3$ are independently N—$R^9$, O, S, SO or $SO_2$ and $Y^4$ is $CR^7R^8$, C=O, SO or $SO_2$.

In one embodiment $Y^1$ is $CR^7R^8$, $Y^2$ is N—$R^9$, O, S, SO or $SO_2$, $Y^3$ is N—$R^9$, and $Y^4$ is $CR^7R^8$, C=O, SO or $SO_2$, preferably $Y^1$ is $CR^7R^8$, $Y^2$ is O or S, $Y^3$ is N—$R^9$, and $Y^4$ is C=O, preferably $Y^1$ is $CR^7R^8$, $Y^2$ is O, $Y^3$ is N—$R^9$, and $Y^4$ is C=O.

In one embodiment $Y^1$ is $CR^7R^8$, $Y^2$ is N—$R^9$, O, S, SO or $SO_2$, $Y^3$ is O or S, $Y^4$ is C=O, SO, or $SO_2$.

In one embodiment $Y^1$ is C=O, $Y^2$ is N—$R^9$ or O, $Y^3$ is N—$R^9$, $Y^4$ is C=O, SO, or $SO_2$.

In one embodiment $Y^1$ is $CR^7R^8$, C=O, $Y^2$ is $CR^7R^8$, C=O, $Y^3$ is N—$R^9$, O or S, and $Y^4$ is SO, or $SO_2$.

Preferably $Y^4$ is $CR^7R^8$ or C=O when L is a bond, e.g. the grouping —$Y^2$—$Y^3$—$Y^4$— is —S—C($R^7$)($R^8$)—, —SO—O—C($R^7$)($R^8$)— or —O—N(—$R^9$)—C(=O)—, more preferably —SO—O—C($R^7$)($R^8$)— or —O—N(—$R^9$)—C(=O)—.

Preferably when $Y^4$ is a heteroatom, L is $C_1$-$C_4$alkylene.

Preferably when $Y^4$ is $NR^9$, L is $C_1$-$C_4$alkylene, in which case $Y^3$ is preferably $NR^9$, O, S, SO or $SO_2$.

Preferably when $Y^4$ is O, L is $C_1$-$C_4$alkylene, in which case $Y^3$ is preferably $NR^9$.

In all embodiments at least two adjacent ring atoms in the ring formed by $Y^1$, $Y^2$, $Y^3$ and $Y^4$ are heteroatoms. Preferably the ring formed by $Y^1$, $Y^2$, $Y^3$ and $Y^4$ does not contain two adjacent oxygen atoms. In some cases there may be no more than one oxygen ring atom in the ring formed by $Y^1$, $Y^2$, $Y^3$ and $Y^4$. Embodiments providing $Y^1$, $Y^2$, $Y^3$, $Y^4$ values may be combined with any of the values, including preferred values, of $A^1$, $A^2$, $A^3$, $A^4$, $G^1$, L, $R^1$, $R^2$, $R^3$, $R^4$, $R^5$, $R^6$, $R^7$, $R^8$, $R^9$ and $R^{10}$.

Preferably each $R^7$ is independently hydrogen, or $C_1$-$C_8$alkyl, most preferably hydrogen.

Preferably each $R^8$ is independently hydrogen, or $C_1$-$C_8$alkyl, most preferably hydrogen.

Preferably $R^7$ and $R^8$ are both hydrogen.

Preferably each $R^9$ is independently hydrogen, cyano-$C_1$-$C_8$alkyl, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_1$-$C_8$haloalkyl, $C_1$-$C_8$hydroxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^{10}$, 5-6 membered heteoaryl-$C_1$-$C_4$alkyl or 5-6 membered heteroaryl-$C_1$-$C_4$alkyl wherein the heteroaryl moiety is substituted by one to three $R^{10}$; more preferably each $R^9$ is independently hydrogen, cyano-$C_1$-$C_8$alkyl-, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_1$-$C_8$haloalkyl, $C_1$-$C_8$ hydroxyalkyl, $C_2$-$C_8$ alkenyl, $C_2$-$C_8$ alkynyl, phenyl-$C_1$-$C_4$ alkyl or phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$; even more preferably each $R^9$ is independently hydrogen, cyano-$C_1$-$C_6$ alkyl, $C_1$-$C_6$alkyl, $C_3$-$C_6$ cycloalkyl, $C_3$-$C_6$cycloalkyl where one carbon atom in the cycloalkyl group is replaced by O, S, S(O) or $SO_2$, or $C_1$-$C_6$halo alkyl, $C_1$-$C_6$hydroxyalkyl, $C_1$-$C_6$ alkoxy-$C_1$-$C_6$ alkyl, $C_2$-$C_6$alkenyl, $C_2$-$C_6$ alkynyl, phenyl-$CH_2$-alkyl or phenyl-$CH_2$— wherein the phenyl moiety is substituted by one to three $R^{10}$, furanyl or furanyl substituted by one to three $R^{10}$, triazolyl or triazolyl optionally substituted by one to three $R^{10}$; yet even more preferably each $R^9$ is independently hydrogen, $C_1$-$C_4$ alkyl, $C_3$-$C_6$ cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^{10}$, furanyl or furanyl substituted by one to three $R^{10}$, thietanyl, oxetanyl, oxo-thietanyl, or dioxo-thietanyl; yet even more preferably each $R^9$ is independently methyl, ethyl, cyclopropyl, cyclobutyl, oxetanyl, thietanyl, trifluoroethyl, difluoroethyl, allyl, propargyl, cyanomethyl, benzyl, benzyl substituted by one to three $R^{10}$, or pyridine-methyl- or pyridine-methyl-substituted by one to three $R^{10}$. Ethyl and trifluoroethyl are particularly preferred. Heteroaryl preferably refers to pyridyl, pyridazinyl, pyrimidinyl, pyrazinyl, pyrazolyl, furanyl, thiophenyl, oxazolyl, isoxazolyl or thiazolyl, more preferably pyridyl, pyrazolyl, furanyl, thiophenyl or thiazolyl, most preferably pyridyl.

Preferably each $R^{10}$ is independently halogen, cyano, $C_1$-$C_8$haloalkyl, $C_1$-$C_8$alkoxy or $C_1$-$C_8$haloalkoxy, most preferably, fluoro, chloro, bromo, trifluoromethyl, trifluoromethoxy, cyano or methoxy.

In one embodiment of compounds of formula (I) $A^1$, $A^2$, $A^3$ and $A^4$ are independently of one another C—H, C—$R^5$, or nitrogen;

$G^1$ is oxygen or sulfur;

L is a single bond or $C_1$-$C_8$alkylene;

$R^1$ is hydrogen, $C_1$-$C_8$alkyl, $C_1$-$C_8$alkylcarbonyl-, or $C_1$-$C_8$alkoxycarbonyl-;

$R^2$ is hydrogen, or $C_1$-$C_8$alkyl;

$R^3$ is $C_1$-$C_8$haloalkyl;

$R^4$ is aryl, aryl substituted by one to three $R^6$, or $R^4$ is heterocyclyl, or heterocyclyl substituted by one to three $R^6$;

each $R^5$ is independently halogen, cyano, nitro, $C_1$-$C_8$ alkyl, $C_3$-$C_8$ cycloalkyl, $C_1$-$C_8$ haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH=CH—CH=CH— bridge;

each $R^6$ is independently halogen, cyano, nitro, $C_1$-$C_8$alkyl, $C_1$-$C_8$haloalkyl, $C_1$-$C_8$alkoxy, or $C_1$-$C_8$ haloalkoxy;

$Y^1$ is $CR^7R^8$ or C=O;

$Y^2$ and $Y^3$ are independently $CR^7R^8$, C=O, N—$R^9$, O, S, SO or $SO_2$;

$Y^4$ is $CR^7R^8$, C=O, SO or $SO_2$;

wherein at least two adjacent ring atoms in the ring formed by $Y^1$, $Y^2$, $Y^3$ and $Y^4$ are heteroatoms;

each $R^7$ and $R^8$ is independently hydrogen, halogen, $C_1$-$C_8$alkyl, or $C_1$-$C_8$haloalkyl;

each $R^9$ is independently hydrogen, cyano, cyano-$C_1$-$C_8$alkyl, $C_1$-$C_8$ alkyl, $C_1$-$C_8$ haloalkyl, $C_3$-$C_8$cycloalkyl, $C_3$-$C_8$cycloalkyl where one carbon atom is replaced by O, S, S(O) or $SO_2$, $C_3$-$C_8$ cycloalkyl-$C_1$-$C_8$ alkyl, $C_3$-$C_8$ cycloalkyl-$C_1$-$C_8$ alkyl where one carbon atom in the cycloalkyl group is replaced by O, S, S(O) or $SO_2$, $C_3$-$C_8$cycloalkyl-$C_1$-$C_8$haloalkyl, $C_1$-$C_8$ hydroxyalkyl, $C_1$-$C_8$ alkoxy-$C_1$-$C_8$alkyl, $C_2$-$C_8$ alkenyl, $C_2$-$C_8$ haloalkenyl, $C_2$-$C_8$ alkynyl, $C_2$-$C_8$haloalkynyl, phenyl-$C_1$-$C_4$alkyl, phenyl-$C_1$-$C_4$alkyl wherein the phenyl moiety is substituted by one to three $R^{10}$, or each $R^9$ is independently 5-6 membered heteroaryl-$C_1$-$C_4$alkyl or 5-6 membered heteroaryl-$C_1$-$C_4$alkyl wherein the heteroaryl moiety is substituted by one to three $R^{10}$;

each $R^{10}$ is independently halogen, cyano, nitro, $C_1$-$C_8$alkyl, $C_1$-$C_8$haloalkyl, $C_1$-$C_8$alkoxy, or $C_1$-$C_8$haloalkoxy, or a salt of N-oxide thereof.

In this embodiment each $R^9$ is preferably independently hydrogen, cyano-$C_1$-$C_8$ cycloalkyl, $C_3$-$C_8$ cycloalkyl-$C_1$-$C_8$alkyl, $C_1$-$C_8$ haloalkyl, $C_1$-$C_8$ hydroxyalkyl, $C_1$-$C_8$ alkoxyalkyl, $C_2$-$C_8$ alkenyl, $C_2$-$C_8$ alkynyl, phenyl-$C_1$-$C_4$alkyl or phenyl-$C_1$-$C_4$alkyl wherein the phenyl moiety is substituted by one to three $R^{10}$, or each $R^9$ is independently heteoaryl-$C_1$-$C_4$alkyl or heteroaryl-$C_1$-$C_4$alkyl wherein the heteroaryl moiety is substituted by one to three $R^{10}$, even more preferably each $R^9$ is independently hydrogen, cyano-$C_1$-$C_8$alkyl, $C_1$-$C_8$alkyl, $C_3$-$C_8$cycloalkyl, $C_1$-$C_8$haloalkyl, $C_1$-$C_8$alkoxyalkyl, $C_2$-$C_8$alkenyl, $C_2$-$C_8$alkynyl, phenyl-$C_1$-$C_4$alkyl- or phenyl-$C_1$-$C_4$alkyl wherein the phenyl moiety is substituted by one to three $R^{10}$, or each $R^9$ is independently heteroaryl-$C_1$-$C_4$alkyl or heteroaryl-$C_1$-$C_4$alkyl wherein the heteroaryl moiety is substituted by one to three $R^{10}$, yet even more preferably each $R^9$ is independently hydrogen, methyl, ethyl, cyclopropyl, cyclobutyl, oxetanyl, thietanyl, trifluoroethyl, difluoroethyl, allyl, propargyl, cyanomethyl, benzyl, benzyl substituted by one to three $R^{10}$, or each $R^9$ is independently pyridine-methyl- or pyridine-methyl-substituted by one to three $R^{10}$. In this embodiment, the preferred values of $Y^1, Y^2, Y^3, Y^4, G^1, R^1, R^2, R^3, R^4, R^5, R^6, R^7, R^8$ and $R^{10}$ are as defined above.

A preferred embodiment provides compounds of formula (Ia.A) wherein $A^1$ is C—$R^5$, $A^2$, $A^3$, and $A^4$ are C—H, $R^4$ is 3,5-dichloro-phenyl, L is a bond, and $G^1, R^1, R^2, R^3, R^5, Y^1, Y^2, Y^3$ and $Y^4$ are as defined for a compound of formula (I); or a salt or N-oxide thereof.

A preferred embodiment provides compounds of formula (Ia.B) wherein $A^1$ is C-Me, $A^2$, $A^3$, and $A^4$ are C—H, $R^4$ is 3,5-dichloro-phenyl, L is a bond, and $G^1, R^1, R^2, R^3, Y^1, Y^2, Y^3$ and $Y^4$ are as defined for a compound of formula (I); or a salt or N-oxide thereof.

A preferred embodiment provides compounds of formula (Ia.C)

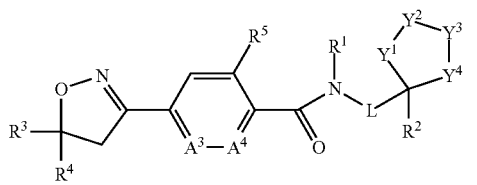

(Ia.C)

wherein $R^2$ is hydrogen or $C_1$-$C_4$ alkyl;

$R^3$ is $C_1$-$C_4$ haloalkyl;

$R^4$ is phenyl, or phenyl substituted by one to three $R^6$;

$R^5$ is halogen, nitro, $C_1$-$C_4$alkyl, $C_3$-$C_4$cycloalkyl, $C_2$-$C_4$alkenyl or $C_1$-$C_4$haloalkyl;

$A^3$ and $A^4$ are independently C—H or N;

L is a bond or methylene;

$R^1, R^6, Y^1, Y^2, Y^3$, and $Y^4$ are as defined for formula (I);

wherein at least two adjacent ring atoms in the ring formed by $Y^1, Y^2, Y^3$ and $Y^4$ are heteroatoms; or a salt or N-oxide thereof. Preferred values of $Y^1, Y^2, Y^3, Y^4, A^3, A^4, R^1, R^2, R^3, R^4, R^5$ and $R^6$ are as defined for formula I.

A preferred embodiment provides compounds of formula (Ia.D)

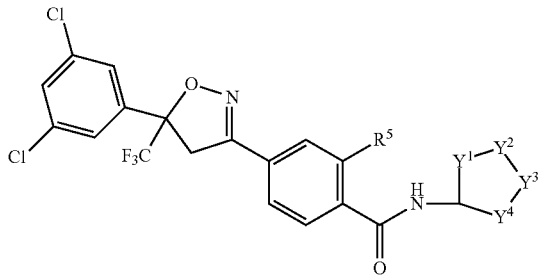

(Ia.D)

wherein $R^5, Y^1, Y^2, Y^3, Y^4$ and their preferred values are as defined for formula (I);

wherein at least two adjacent ring atoms in the ring formed by $Y^1, Y^2, Y^3$ and $Y^4$ are heteroatoms; or a salt or N-oxide thereof.

A further preferred embodiment provides compounds of formula (Ia.E)

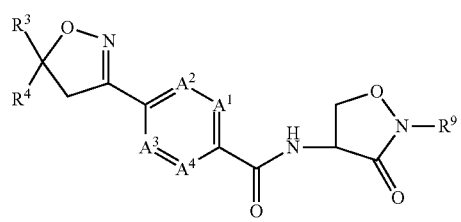

(Ia.E)

wherein $A^1, A^2, A^3, A^4, R^3, R^4$ and $R^9$ and their preferred values are as defined for a compound of formula (I); or a salt or N-oxide thereof. Certain intermediates are novel and as such form a further aspect of the invention.

A further preferred embodiment provides compounds of formula (Ia.F)

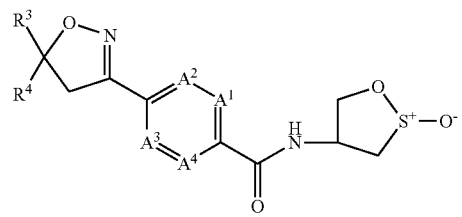

(Ia.F)

wherein $A^1, A^2, A^3, A^4, R^3$ and $R^4$ and their preferred values are as defined for a compound of formula (I); or a salt or N-oxide thereof.

Certain intermediates are novel and as such form a further aspect of the invention. One group of novel intermediates are compounds of formula (Int-I)

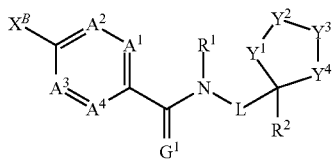

(Int-I)

wherein $A^1, A^2, A^3, A^4, G^1, L, R^1, R^2, Y^1, Y^2, Y^3$ and $Y^4$ are as defined for a compound of formula (I) and $X^B$ is a leaving group, for example a halogen, such as bromo, or $X^B$ is cyano, formyl, CH=N—OH or acetyl; or a salt or N-oxide thereof. The preferences for $A^1, A^2, A^3, A^4, G^1, L, R^1, R^2, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, Y^1, Y^2, Y^3$ and $Y^4$ may be the same as for formula (Ia.A), (Ia.B), (Ia.C), (Ia.D), (Ia.E) or (Ia.F).

Another group of novel intermediates are compounds of formula (Int-II)

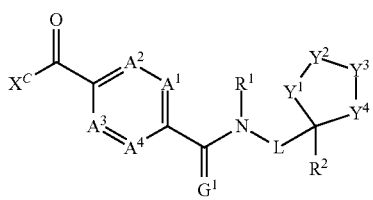

(Int-II)

wherein $A^1, A^2, A^3, A^4, G^1, L, R^1, R^2, Y^1, Y^2, Y^3$ and $Y^4$ are as defined for a compound of formula (I); $X^C$ is CH$_2$-halogen, wherein halogen is e.g. bromo or chloro, CH=C(R$^3$)R$^4$ or CH$_2$C(OH)(R$^3$)R$^4$ wherein R$^3$ and R$^4$ are as defined for a compound of formula (I); or a salt or N-oxide thereof. The preferences for $A^1, A^2, A^3, A^4, G^1, L, R^1, R^2, Y^1, Y^2, Y^3$ and $Y^4$ are the same as the preferences set out for the corresponding substituents of a compound of formula (I). For example, the preferences for $A^1, A^2, A^3, A^4, G^1, L, R^1, R^2, Y^1, Y^2, Y^3$ and $Y^4$ may be the same as for formula (Ia.A), (Ia.B), (Ia.C), (Ia.D), (Ia.E) or (Ia.F).

The compounds in Table 1 to Table 2 below illustrate the compounds of the invention.

TABLE 1

Table 1 provides compounds of formula (Ia) wherein R$^2$ is hydrogen, R$^5$ is methyl, Y$^1$ and Y$^4$ are CH$_2$, and R$^2$, Y$^2$ and Y$^3$ have the values listed in the table below.

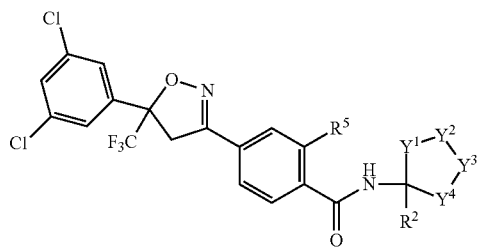

(Ia)

| Compound numbers | R$^2$ | Y$^2$ | Y$^3$ |
| --- | --- | --- | --- |
| 1.01 | H | S | S |
| 1.02 | H | S(O) | S |

TABLE 2

Table 2 provides compounds of formula (Ib) wherein G$^1$ is oxygen, and R$^5$ and R$^9$ have the values listed in the table below.

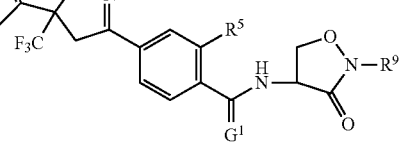

(Ib)

| Compound numbers | R$^5$ | R$^9$ |
| --- | --- | --- |
| 2.01 | methyl | ethyl- |
| 2.02 | methyl | butyl- |
| 2.03 | methyl | but-2-yl- |
| 2.04 | methyl | 3-bromo-propyl- |
| 2.05 | methyl | 2,2,2-trifluoro-ethyl- |
| 2.06 | methyl | 3,3,3-trifluoro-propyl- |
| 2.07 | methyl | 2-methoxy-ethyl- |
| 2.08 | methyl | 1-methoxy-prop-2-yl- |
| 2.09 | methyl | cyclobutyl- |
| 2.10 | methyl | 2-methyl-cyclohex-1-yl- |
| 2.11 | methyl | phenyl-methyl- |
| 2.12 | methyl | 1-phenyl-eth-1-yl- |
| 2.13 | methyl | 2-phenyl-eth-1-yl- |
| 2.14 | methyl | (3-chloro-phenyl)-methyl- |
| 2.15 | methyl | (2-fluoro-phenyl)-methyl- |
| 2.16 | methyl | (4-methoxy-phenyl)-methyl- |
| 2.17 | methyl | (2-trifluoromethyl-phenyl)-methyl- |
| 2.18 | methyl | (2-trifluoromethoxy-phenyl)-methyl- |
| 2.19 | methyl | (pyrid-2-yl)-methyl- |
| 2.20 | methyl | (pyrid-3-yl)-methyl- |
| 2.21 | methyl | (2-chloro-pyrid-5-yl)-methyl- |
| 2.22 | methyl | (1-methyl-1H-imidazol-4-yl)-methyl- |
| 2.23 | methyl | (furan-2-yl)-methyl- |
| 2.24 | methyl | 2-(thiophen-2'-yl)-eth-1-yl- |
| 2.25 | methyl | 2-(indol-3'-yl)- |
| 2.26 | methyl | (1H-benzimidazol-2-yl)-methyl- |
| 2.27 | methyl | (oxetan-2-yl)-methyl- |
| 2.28 | methyl | (tetrahydrofuran-2-yl)-methyl- |
| 2.29 | methyl | 2-([1',3']dioxolan-2'-yl)-eth-1-yl- |
| 2.30 | methyl | 2-(morpholin-4'-yl)-eth-1-yl- |
| 2.31 | methyl | 2-(benzo[1',3'dioxo1-5'-yl)-eth-1-yl- |
| 2.32 | methyl | (2,3-dihydro-benzo[1,4]dioxin-6-yl)-methyl- |
| 2.33 | methyl | 2-chloro-phenyl- |
| 2.34 | methyl | 3-fluoro-phenyl- |
| 2.35 | methyl | 2-methyl-phenyl- |
| 2.36 | methyl | 2-chloro-6-methyl-phenyl- |
| 2.37 | methyl | 2-trifluoromethyl-phenyl- |
| 2.38 | methyl | 2,4-dimethoxy-phenyl- |
| 2.39 | methyl | 3-methyl-pyrid-2-yl- |
| 2.40 | methyl | 1,3-dimethyl-1H-pyrazol-5-yl- |
| 2.41 | methyl | 4-methyl-thiazol-2-yl- |
| 2.42 | methyl | 5-methyl-thiadiazol-2-yl- |
| 2.43 | methyl | quinolin-2-yl- |
| 2.44 | methyl | quinolin-5-yl- |
| 2.45 | methyl | benzothiazol-6-yl- |
| 2.46 | methyl | 4-methyl-benzothiazol-2-yl- |
| 2.47 | methyl | thietan-3-yl- |
| 2.48 | methyl | 1-oxo-thietan-3-yl- |
| 2.49 | methyl | 1,1-dioxo-thietan-3-yl- |
| 2.50 | methyl | 3-methyl-thietan-3-yl- |
| 2.51 | methyl | oxetan-3yl |
| 2.52 | methyl | tetrahydropyran-4-yl |
| 2.53 | methyl | hydrogen |
| 2.54 | methyl | methyl |
| 2.55 | methyl | propyl |
| 2.56 | methyl | 2,2-difluoro-ethyl- |
| 2.57 | methyl | 2-fluoro-ethyl- |

Compounds of formula I include at least one chiral centre and may exist as compounds of formula I* or compounds of formula I**. Compounds I* and I** are enantiomers if there is no other chiral center or epimers otherwise.

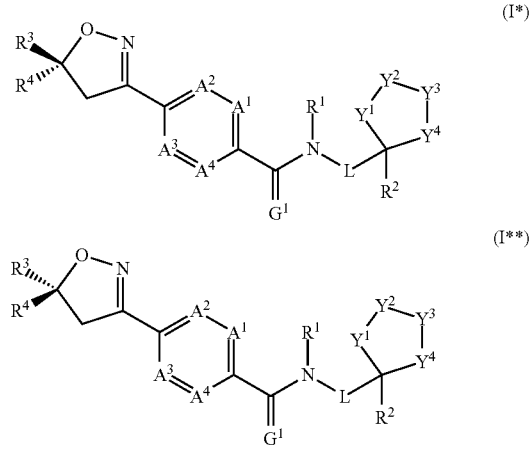

Generally compounds of formula I** are more biologically active than compounds of formula I*. The invention includes mixtures of compounds I* and I in any ratio e.g. in a molar ratio of 1:99 to 99:1, e.g. 10:1 to 1:10, e.g. a substantially 50:50 molar ratio. In an enantiomerically (or epimerically) enriched mixture of formula I, the molar proportion of compound I** compared to the total amount of both enantiomers is for example greater than 50%, e.g. at least 55, 60, 65, 70, 75, 80, 85, 90, 95, 96, 97, 98, or at least 99%. Likewise, in enantiomerically (or epimerically) enriched mixture of formula I*, the molar proportion of the compound of formula I* compared to the total amount of both enantiomers (or epimerically) is for example greater than 50%, e.g. at least 55, 60, 65, 70, 75, 80, 85, 90, 95, 96, 97, 98, or at least 99%. Enantiomerically (or epimerically) enriched mixtures of formula I** are preferred.

The compounds of the invention may be made by a variety of methods as shown in Schemes 1 and 2.

coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art. Some of these methods are described in the preparation Examples.

2) Acid halides of formula (II), wherein $G^1$ is oxygen and R is Cl, F or Br, may be made from carboxylic acids of formula (II), wherein $G^1$ is oxygen and R is OH, under standard conditions, as described for example in WO09080250.

3) Carboxylic acids of formula (II), wherein $G^1$ is oxygen and R is OH, may be formed from esters of formula (II), wherein $G^1$ is oxygen and R is $C_1$-$C_6$alkoxy as described for example in WO09080250.

4) Compounds of formula (I) wherein $G^1$ is oxygen, can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triph-

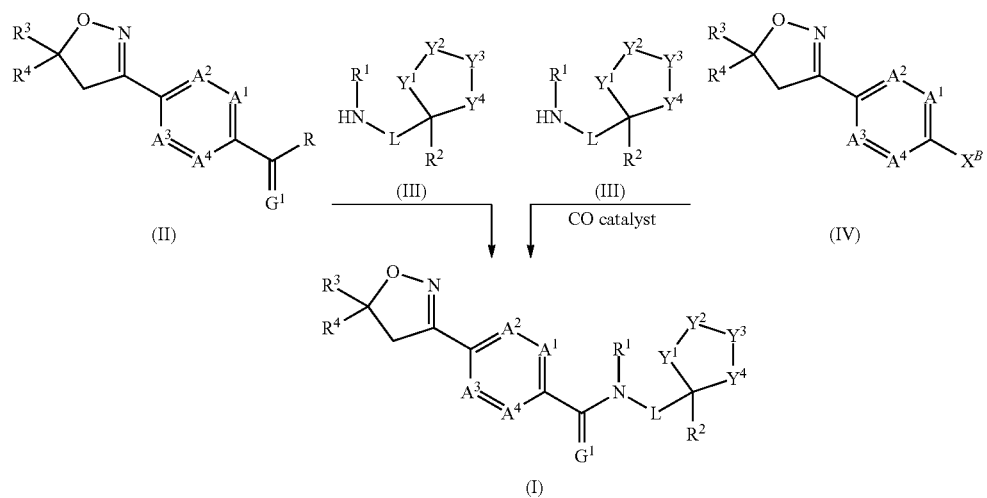

1) Compounds of formula (I) wherein $G^1$ is oxygen, can be prepared by reacting a compound of formula (II) wherein $G^1$ is oxygen and R is OH, $C_1$-$C_6$alkoxy or Cl, F or Br, with an amine of formula (III) as shown in Scheme 1. When R is OH such reactions are usually carried out in the presence of a enylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropyl-ethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO09080250.

6) Compounds of formula (I), wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

Scheme 2

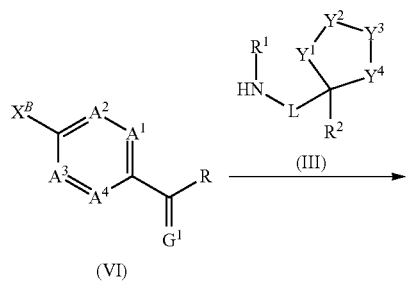

(VI)

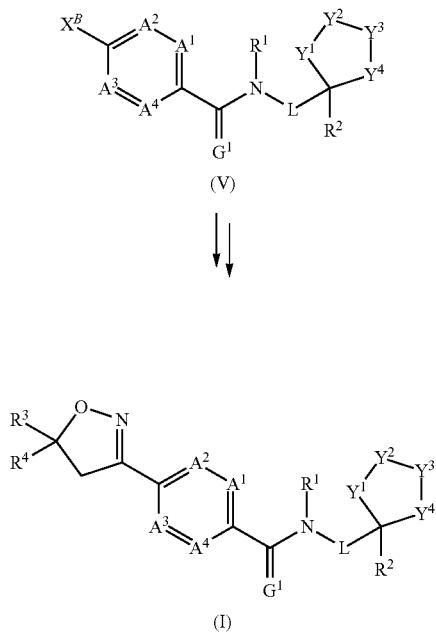

(I)

7) Alternatively, compounds of formula (I) wherein $G^1$ is oxygen, can be prepared by various methods from an intermediate of formula (V) as shown in Scheme 2 wherein $G^1$ is oxygen and $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

Scheme 3

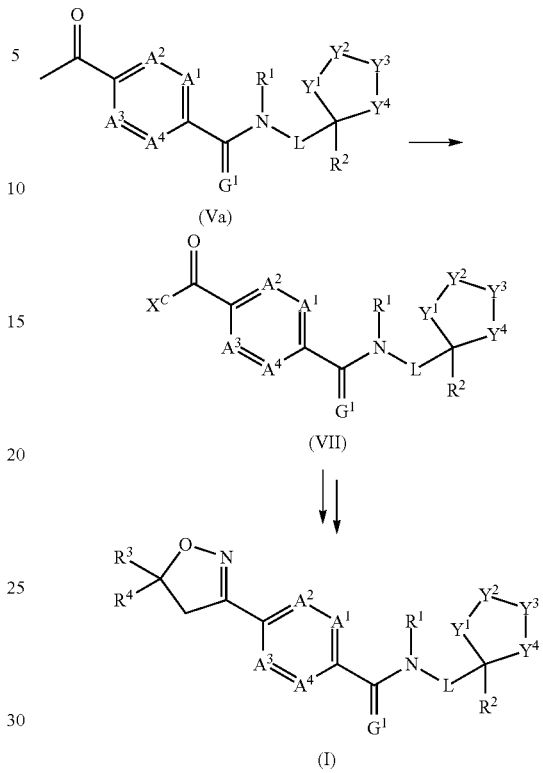

8) Alternatively, compounds of formula (I) wherein $G^1$ is oxygen, can be prepared by various methods from an intermediate of formula (VII) as shown in Scheme 3 wherein $G^1$ is oxygen and $X^C$ is CH=C($R^3$)$R^4$, or CH$_2$C(OH)($R^3$)$R^4$ wherein $R^3$ and $R^4$ are as defined for a compound of formula (I) according to similar methods to those described in WO09080250.

9) Compounds of formula (VII) wherein $G^1$ is oxygen and $X^C$ is CH=C($R^3$)$R^4$, or CH$_2$C(OH)($R^3$)$R^4$ can be prepared from a compound of formula (Va) wherein $G^1$ is oxygen or from a compound of formula (VII) wherein $G^1$ is oxygen and $X^C$ is CH$_2$-halogen using similar methods to those described in WO09080250.

10) Compounds of formula (VII) wherein $G^1$ is oxygen and $X^C$ is CH$_2$-halogen, such as bromo or chloro, can be prepared by reacting a methyl ketone of formula (Va) wherein $G^1$ is oxygen, with a halogenating agent, such as bromine or chlorine, in a solvent, such as acetic acid, at a temperature of from 0° C. to 50° C., preferably from ambient temperature to 40° C.

11) Compounds of formula (III) are either known compounds or can be prepared by known methods to the person skilled in the art. Examples of such methods can be found in the Examples below.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes* sulfureus), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin and gamma cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl) cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron, lufeneron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole (Rynaxypyr®) or cyantraniliprole;

t) Sulfoxaflor; or u) Metaflumizone;

v) Fipronil and Ethiprole;

w) Pyrifluqinazon;

x) buprofezin; or y) 4-[(6-Chloro-pyridin-3-ylmethyl)-(2,2-difluoro-ethyl)-amino]-5H-furan-2-one (DE 102006015467) In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)—N-methyl-2-[2-(2,5-dimethylphenoxymethyl)phenyl]-2-methoxy-iminoacetamide (SSF-129), 4-bromo-2-cyano-N,N-dimethyl-6-trifluoromethyl-benzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5-dimethyl-2-trimethylsilylthiophene-3-carboxamide (MON65500), N-(1-cyano-1,2-dimethylpropyl)-2-(2,4-dichlorophenoxy)-propionamide (AC382042), N-(2-methoxy-5-pyridyl)-cyclopropane carboxamide, acibenzolar (CGA245704) (e.g. acibenzolar-S-methyl), alanycarb, aldimorph, anilazine, azaconazole, azoxystrobin, benalaxyl, benomyl, benthiavalicarb, biloxazol, bitertanol, bixafen, blasticidin S, boscalid, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cyclufenamid, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)—N-benzyl-N-([methyl(methyl-thioethylideneaminooxy carbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluopyram, fluoxastrobin, fluoroimide, fluquinconazole, flusilazole, flutolanil, flutriafol, fluxapyroxad, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, isopyrazam, kasugamycin, kresoxim-methyl, LY186054, LY211795, LY248908, mancozeb, mandipropamid, maneb, mefenoxam, metalaxyl, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, penflufen, penthiopyrad, phenazin oxide, phosetyl-Al, phosphorus acids, phthalide, picoxystrobin (ZA1963), polyoxinD, polyram, probenazole, prochloraz, procymidone, propamocarb, propiconazole, propineb, propionic acid, prothioconazole, pyrazophos, pyrifenox, pyrimethanil, pyraclostrobin, pyroquilon, pyroxyfur, pyrolnitrin, quaternary ammonium compounds, quinomethionate, quinoxyfen, quintozene, sedaxane, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram, 1,3-Dimethyl-1H-pyrazole-4-carboxylic acid (4'-methylsulfanyl-biphenyl-2-yl)-amide, 1,3-Dimethyl-1H-pyrazole-4-carboxylic acid (2-dichloromethylene-3-ethyl-1-methyl-indan-4-yl)-amide, and 1,3-Dimethyl-4H-pyrazole-4-carboxylic acid [2-(2,4-dichloro-phenyl)-2-methoxy-1-methyl-ethyl]-amide.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is a compound of the invention and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. No. 5,478,855, U.S. Pat. No. 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl(E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide; more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone; even more preferably, enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms. Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals. Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria.*

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma.*

Cestodes that are contemplated to be treated by the invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella.*

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, ($6^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the Gastrophilus of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi.*

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia (Lyperosia) irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally adminstered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection. The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly administration intervals (i.e. administering the compounds to the animal once every month).

The following Examples illustrate, but do not limit, the invention.

The following abbreviations were used in this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, $[M+H]^+$=olecular mass of the molecular cation, $[M-H]^-$=molecular mass of the molecular anion.

The following LC-MS methods were used to characterize the compounds:

Method A

| | |
|---|---|
| MS | ZQ Mass Spectrometer from Waters (single quadrupole mass spectrometer), ionization method: electrospray, polarity: positive ionization, capillary (kV) 3.00, cone (V) 30.00, source temperature (° C.) 100, desolvation temperature (° C.) 250, cone gas flow (L/Hr) 50, desolvation gas flow (L/Hr) 400, mass range: 150 to 1000 Da. |
| LC | HP 1100 HPLC from Agilent: solvent degasser, quaternary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |

Method B

| | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 5.0 | 0.0 | 100 | 1.7 |
| 5.6 | 0.0 | 100 | 1.7 |
| 6.0 | 80 | 20 | 1.7 |

Method C

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |
| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 90 | 10 | 1.7 |
| 5.5 | 0.0 | 100 | 1.7 |
| 5.8 | 0.0 | 100 | 1.7 |
| 5.9 | 90 | 10 | 1.7 |

Method D

| | |
|---|---|
| MS | ZMD Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 150, desolvation temperature (° C.) 320, cone gas flow (L/Hr) 50, desolvation gas flow (L/Hr) 400, mass range: 150 to 800 Da. |
| LC | Alliance 2795 LC HPLC from Waters: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method E

| | |
|---|---|
| MS | ZQ Mass Spectrometer from Waters (single quadrupole mass spectrometer), ionization method: electrospray, polarity: positive ionization, capillary (kV) 3.00, cone (V) 30.00, extractor (V) 3.00, source temperature (° C.) 100, desolvation temperature (° C.) 200, cone gas flow (L/Hr) 200, desolvation gas flow (L/Hr) 250, mass range: 150 to 800 Da. |

| LC | 1100er Series HPLC from Agilent: quaternary pump, heated column compartment and diode-array detector. Column: Waters Atlantis dc18, length (mm) 20, internal diameter (mm) 3, particle size (μm) 3, temperature (° C.) 40, DAD wavelength range (nm): 200 to 500, solvent gradient: A = 0.1% v/v formic acid in water and B = 0.1% v/v formic acid in acetonitrile. |
|---|---|

| Time (min) | A % | B % | Flow (ml/min) |
|---|---|---|---|
| 0.0 | 80 | 20 | 1.7 |
| 2.5 | 0.0 | 100 | 1.7 |
| 2.8 | 0.0 | 100 | 1.7 |
| 2.9 | 80 | 20 | 1.7 |

Method F

| MS | ZQ Mass Spectrometer from Waters (single quadrupole mass spectrometer), ionization method: electrospray, polarity: negative ionization, capillary (kV) 3.00, cone (V) 45.00, source temperature (° C.) 100, desolvation temperature (° C.) 250, cone gas flow (L/Hr) 50, desolvation gas flow (L/Hr) 400, mass range: 150 to 1000 Da. |
|---|---|
| LC | HP 1100 HPLC from Agilent: solvent degasser, binary pump, heated column compartment and diode-array detector. Column: Phenomenex Gemini C18, length (mm) 30, internal diameter (mm) 3, particle size (μm) 3, temperature (° C.) 60, DAD wavelength range (nm): 200 to 500, solvent gradient: A = 0.05% v/v formic acid in water and B = 0.04% v/v formic acid in acetonitrile/methanol (4:1). |

| Time (min) | A % | B % | Flow (ml/min) |
|---|---|---|---|
| 0.0 | 95 | 5.0 | 1.7 |
| 2.0 | 0.0 | 100 | 1.7 |
| 2.8 | 0.0 | 100 | 1.7 |
| 2.9 | 95 | 5.0 | 1.7 |
| 3.1 | 95 | 5 | 1.7 |

Method G

| MS | Thermo Finnigan Surveyor MSQ PLUS (single quadrupole mass spectrometer), ionization method: Chemical Ionization, polarity: positive and negative simultaneous ionization, capillary (kV) 4.00, cone (V) 50.00, source temperature (° C.) 350, mass range: 110 to 800 Da. |
|---|---|
| LC | Thermo Finnigan Surveyor LC: solvent degasser, quaternary pump, heated column compartment and diode-array detector. Column: XTerra RP18, length (mm) 50, internal diameter (mm) 4.6, particle size (μm) 3.5, temperature (° C.) 30, DAD wavelength range (nm): 200 to 400, solvent gradient: A = 0.05% v/v formic acid in water and B = 0.05% v/v formic acid in acetonitrile |

| Time (min) | A % | B % | Flow (ml/min) |
|---|---|---|---|
| 0.0 | 90.0 | 10.0 | 1.7 |
| 3.2 | 10.0 | 90.0 | 1.7 |
| 5.0 | 10.0 | 90.0 | 1.7 |
| 5.2 | 90.0 | 10.0 | 1.7 |
| 6.0 | 90.0 | 10.0 | 1.7 |

Method H

| CHIRAL HPLC | Alliance 2695 HPLC from Waters: solvent degasser, binary pump, heated column compartment and diode-array detector Column: Chiralpak IC, length (mm) 250, internal diameter (mm) 4.6, particle size (μ) 5, wavelength (nm): 220 nm, temperature (° C.) 30, solvent: Isocratic isopropyl alcohol:heptane 20:80, injection volume 50 uL, flow (ml/min) 1. |
|---|---|

Method J

| | |
|---|---|
| MS | Waters ACQUITY SQD Mass Spectrometer from Waters (Single quadrupole mass spectrometer) |
| | Ionisation method: Electrospray |
| | Polarity: positive ions |
| | Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700 |
| | Mass range: 100 to 800 Da |
| | DAD Wavelength range (nm): 210 to 400 |
| LC | Waters ACQUITY UPLC with the following HPLC gradient conditions (Solvent A: Water/Methanol 9:1, 0.1% formic acid and Solvent B: Acetonitrile, 0.1% formic acid) |

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Method K

| | |
|---|---|
| CHIRAL HPLC | Alliance 2695 HPLC from Waters: solvent degasser, binary pump, heated column compartment and diode-array detector |
| | Column: Chiralpak IB, length (mm) 250, internal diameter (mm) 4.6, particle size (µ) 5, wavelength (nm): 270 nm, temperature (° C.) 30, solvent: Isocratic isopropyl alcohol:heptanes:diethylamine 30:70:0.1, injection volume 50 uL, flow (ml/min) 1. |

EXAMPLE 1

4-[5-(3,5-Dichloro-phenyl)-5-trifluoromethyl-4,5-dihydro-isoxazol-3-yl]-N-[1,2]dithiolan-4-yl-2-methyl-benzamide (compound A1)

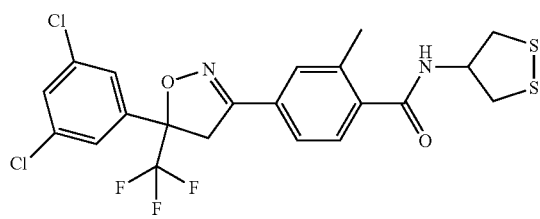 [SMILES: Cc1cc(C2=NOC(c3cc(Cl)cc(Cl)c3)(C(F)(F)F)C2)ccc1C(=O)NC1CSSC1]

Step A: Thioacetic acid S-(3-acetylsulfanyl-2-tert-butoxycarbonylamino-propyl) ester

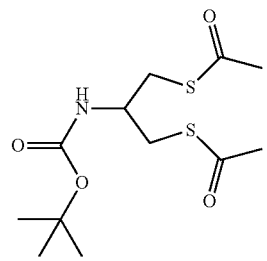 [SMILES: CC(=O)SCC(CSC(C)=O)NC(=O)OC(C)(C)C]

Methanesulfonic acid 2-tert-butoxycarbonylamino-3-methanesulfonyloxy-propyl ester (Synthesis (1998), (8), 1113-1118) in dimethylformamide (5 ml) and potassium thioacetate (685 mg) in dimethylformamide (5 ml) were added dropwise. The reaction was stirred overnight at room temperature then poured into water. A yellow-brown solid precipitated which was filtered and washed with water to give 220 mg of the title product. The aqueous phase was extracted with diethyl ether, the organic phase was dried over sodium sulfate, filtered and evaporated in vacuo to give another 110 mg of the title product. $^1$H-NMR (CDCl$_3$, 400 MHz): 4.80 (m, 1H), 3.90 (m, 1H), 3.10 (m, 4H), 2.40 (s, 6H), 1.40 (s, 9H).

Step B: [1,2]-Dithiolan-4-yl-carbamic acid tert-butyl ester

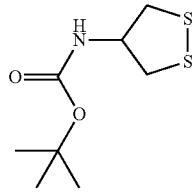

A solution of thioacetic acid S-(3-acetylsulfanyl-2-tert-butoxycarbonylamino-propyl) ester (330 mg) in ethanol (5 ml) was treated with 2.5 ml of 1N sodium hydroxide for 1 hour at room temperature. The yellow solid turned green-brown. The reaction mixture was diluted with dichloromethane (25 ml) and then an aqueous solution of 0.1M iodine (10 ml) was added dropwise. The reaction mixture was stirred at room temperature for 1 hour and quenched by addition of 1M sodium bisulfite solution. The organic layer was separated, washed with water, dried over sodium sulfate and the solvent evaporated in vacuo to afford the title product (170 mg). $^1$H-NMR (CDCl$_3$, 400 MHz): 5.00 (br s, 1H), 4.90 (m, 1H), 3.15 (d, 2H), 3.05 (d, 2H), 1.40 (s, 9H).

Step C: [1,2]-Dithiolan-4-ylamine

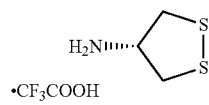

The BOC protecting group was removed as described in Example 3, Step B to afford the title compound (trifluoroacetic acid salt), which was used directly in the next step.

Step D: 4-[5-(3,5-Dichloro-phenyl)-5-trifluoromethyl-4,5-dihydro-isoxazol-3-yl]-N-[1,2]dithiolan-4-yl-2-methyl-benzamide

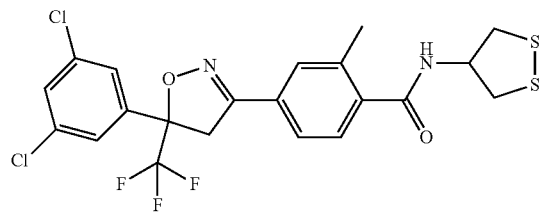 [SMILES: Cc1cc(C2=NOC(c3cc(Cl)cc(Cl)c3)(C(F)(F)F)C2)ccc1C(=O)NC1CSSC1]

Amide coupling was performed as described in Example 3, Step C to afford the title compound as a solid (40 mg). M.p. 73° C.; LCMS (Method F) 2.20 min, M−H 519/521. $^1$H-NMR (CDCl$_3$, 400 MHz): 7.50-7.30 (m, 6H), 6.20 (m, 1H), 5.35 (m, 1H), 4.00 (d, 1H), 3.60 (d, 1H), 3.30 (m, 2H), 3.20 (m, 2H), 2.40 (s, 3H).

EXAMPLE 2

4-[5-(3,5-Dichloro-phenyl)-5-trifluoromethyl-4,5-dihydro-isoxazol-3-yl]-2-methyl-N-((R)-3-oxo-isoxazolidin-4-yl)-benzamide (compound B1)

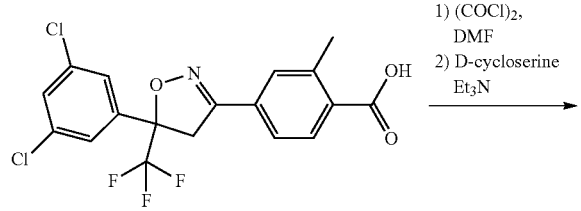

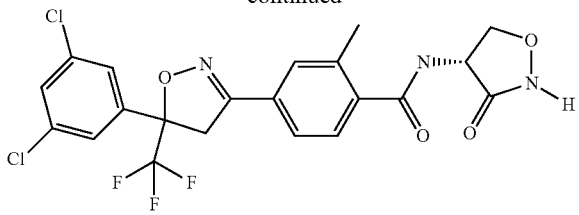

Oxalyl chloride (0.122 ml) was added to a solution of 4-[5-(3,5-dichloro-phenyl)-5-trifluoromethyl-4,5-dihydro-isoxazol-3-yl]-2-methyl-benzoic acid (0.5 g) (prepared according to WO 2009/080250) in dichloromethane (3 ml). After addition of two drops of N,N-dimethylformamide ("DMF") the reaction mixture was stirred at ambient temperature for 18 hours. The reaction mixture was concentrated to give the acid chloride as a yellow solid, which was used in the next step without further purification.

D-cycloserine (21 mg) was added to a solution of the acid chloride (45 mg) and triethylamine (0.1 ml) in toluene (2 ml). The reaction mixture was stirred at 50° C. for 16 hours. The reaction mixture was diluted with water and ethyl acetate and the phases were separated. The organic phase was washed twice with water, dried over sodium sulfate and concentrated. The residue was purified by chromatography on silica gel (eluent: dichloromethane/methanol 5%) to give the title compound (28 mg) as a colorless solid. $^1$H-NMR (CDCl$_3$, 400 MHz): 8.60 (s, br., 1H), 7.60-7.45 (m, 6H), 6.40 (s, 1H), 5.05 (m, 1H), 4.85 (m, 1H), 4.20 (t, 1H), 4.05 (d, 1H), 3.70 (d, 1H), 2.50 (s, 3H) ppm.

EXAMPLE 3

4-[5-(3,5-Dichloro-phenyl)-5-trifluoromethyl-4,5-dihydro-isoxazol-3-yl]-2-methyl-N-((R)-2-methyl-3-oxo-isoxazolidin-4-yl)-benzamide (compound B2)

Step A: ((R)-2-Methyl-3-oxo-isoxazolidin-4-yl)-carbamic acid tert-butyl ester

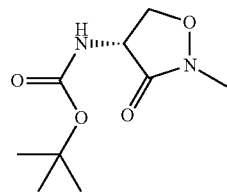

(3-Oxo-isoxazolidin-4-yl)-carbamic acid tert-butyl ester (1.01 g, prepared from (D)-cycloserine as described in Chem. Pharm. Bull. 2002, 50(4) 554-557) was dissolved in dimethylformamide (5 ml), the solution was cooled to 0° C. and 616 mg of potassium t-butoxide was added portionwise. The reaction mixture was stirred at 0° C. for 1 hour then 710 mg methylene iodide was added and the reaction mixture was stirred for 3 hours at room temperature. The reaction mixture was poured into water and extracted with diethyl ether. The organic phase was then washed several times with water, dried over sodium sulphate and the solvent removed in vacuo. Crude ((R)-2-methyl-3-oxo-isoxazolidin-4-yl)-carbamic acid tert-butyl ester (140 mg) was obtained as a white solid. LCMS (method A) 1.11 min, MH$^+$ 217; $^1$H-NMR (CDCl$_3$, 400 MHz): 5.20 (m, 1H), 4.70 (m, 1H), 4.55 (m, 1H), 4.00 (dd, 1H), 3.20 (s, 3H), 1.40 (s, 9H).

Step B: (R)-4-Amino-2-methyl-isoxazolidin-3-one

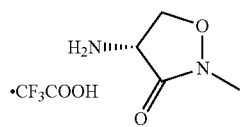

((R)-2-methyl-3-oxo-isoxazolidin-4-yl)-carbamic acid tert-butyl ester of Step A (108 mg) was dissolved in dichloromethane (5 ml) and treated with trifluoroacetic acid (0.2 ml). The reaction mixture was stirred at room temperature for 1 hour and the solvent removed in vacuo to afford (R)-4-Amino-2-methyl-isoxazolidin-3-one (trifluoroacetic acid salt), which was used directly in the next step.

Step C: 4-[5-(3,5-Dichloro-phenyl)-5-trifluoromethyl-4,5-dihydro-isoxazol-3-yl]-2-methyl-N-((R)-2-methyl-3-oxo-isoxazolidin-4-yl)-benzamide

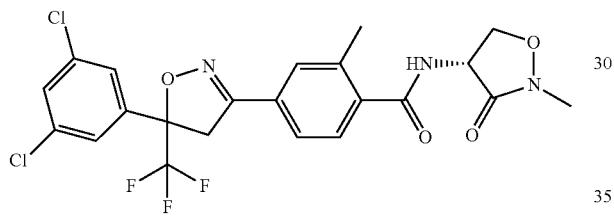

To a suspension of 4-[5-(3,5-dichloro-phenyl)-5-trifluoromethyl-4,5-dihydro-isoxazol-3-yl]-benzoic acid (175 mg, prepared as described in WO2009/080250) in dichloromethane (5 ml) was added oxalyl chloride (0.05 ml) and then one drop of dimethylformamide. The reaction mixture stirred at room temperature for 2 hours 30 minutes, and the solvent was evaporated in vacuo to give a pink solid (acid chloride, 170 mg). The acid chloride thus obtained was dissolved in dichloromethane (2 ml) and the resulting solution was added dropwise to a solution of triethylamine (0.35 ml) and (R)-4-Amino-2-methyl-isoxazolidin-3-one (obtained in Step B) in dichloromethane (3 ml) at room temperature, under argon. The reaction was stirred overnight at room temperature, diluted with water, and extracted with ethyl acetate. The organic phase was washed two times with water, dried over anhydrous sodium sulfate, filtered and concentrated in vacuo. Purification by column chromatography (eluent cyclohexane/ethyl acetate) afforded the title compound as a solid (70 mg). M.p. 87° C.; LCMS (Method A) 1.99 min, MH+ 516/518. $^1$H-NMR (CDCl$_3$, 400 MHz): 7.60-7.40 (m, 6H), 6.45 (m, 1H), 5.00 (t, 1H), 4.87 (m, 1H), 4.10 (m, 2H), 3.70 (d, 1H), 3.25 (s, 3H), 2.50 (s, 3H).

The following compounds were prepared following a similar method to that described in Example 3: 4-[5-(3,5-Dichloro-phenyl)-5-trifluoromethyl-4,5-dihydro-isoxazol-3-yl]-2-methyl-N-((R)-2-propargyl-3-oxo-isoxazolidin-4-yl)-benzamide (compound B3) (using propargyl bromide as an alkylating agent in Step A); 4-[5-(3,5-Dichloro-phenyl)-5-trifluoromethyl-4,5-dihydro-isoxazol-3-yl]-2-methyl-N-((R)-2-benzyl-3-oxo-isoxazolidin-4-yl)-benzamide (compound B4) (using benzyl bromide as an alkylating agent in Step A); 4-[5-(3,5-Dichloro-phenyl)-5-trifluoromethyl-4,5-dihydro-isoxazol-3-yl]-2-methyl-N-((R)-2-(2,2,2-trifluoro-ethyl-3-oxo-isoxazolidin-4-yl)-benzamide (compound B5) (using 2,2,2-trifluoroethyl trifluoromethanesulfonate as alkylating agent in Step A); 4-[5-(3,5-Dichloro-phenyl)-5-trifluoromethyl-4,5-dihydro-isoxazol-3-yl]-2-methyl-N-((S)-2-methyl-3-oxo-isoxazolidin-4-yl)-benzamide (Compound E1) (starting from (S)-cycloserine)

EXAMPLE 4

4-[5-(3,5-Dichloro-phenyl)-5-trifluoromethyl-4,5-dihydro-isoxazol-3-yl]-2-methyl-N-((R)-2-ethyl-3-oxo-isoxazolidin-4-yl)-benzamide (compound B6)

Step A: ((R)-2-ethyl-3-oxo-isoxazolidin-4-yl)-carbamic acid tert-butyl ester

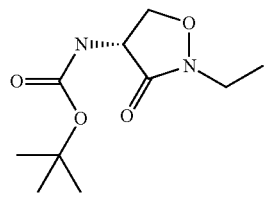 [SMILES: CCN1OC[C@@H](NC(=O)OC(C)(C)C)C1=O]

(3-Oxo-isoxazolidin-4-yl)-carbamic acid tert-butyl ester (0.2 g, prepared from (D)-cycloserine as described in Chem. Pharm. Bull. 2002, 50(4) 554-557) was dissolved in acetonitrile (20 ml) then potassium carbonate (0.69 g), potassium iodide (0.175 g) and bromoethane (0.13 g) were added. The reaction was heated under microwave irradiation for 1 hour at 140° C. The reaction mixture was partitioned between ethyl acetate and water. The organic layer was washed with water, brine and then dried over sodium sulphate. The solvent was removed in vacuo and the crude product was purified by column chromatography (eluent cyclohexane/ethyl acetate) to afford ((R)-2-ethyl-3-oxo-isoxazolidin-4-yl)-carbamic acid tert-butyl ester as a yellow solid. LCMS (method A) 1.29 min, MH+(-BOC) 131; $^1$H-NMR (CDCl$_3$, 400 MHz): 5.10 (m, 1H), 4.75 (m, 1H), 4.55 (m, 1H), 3.95 (m, 1H), 3.60 (m, 2H), 1.50 (s, 9H), 1.20 (m, 3H).

Step B: (R)-4-Amino-2-ethyl-isoxazolidin-3-one

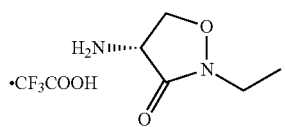

The BOC protecting group was removed as described in Example 3, Step B to afford (R)-4-amino-2-ethyl-isoxazolidin-3-one (trifluoroacetic acid salt), which was used directly in the next step.

Step C: 4-[5-(3,5-Dichloro-phenyl)-5-trifluoromethyl-4,5-dihydro-isoxazol-3-yl]-2-methyl-N-((R)-2-ethyl-3-oxo-isoxazolidin-4-yl)-benzamide

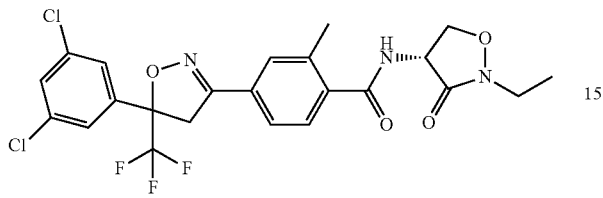

Amide coupling was performed as described in Example 3, Step C to afford the title compound as a solid (160 mg). M.p. 140° C.; LCMS (Method A) 2.05 min, M–H 528/530. $^1$H-NMR (CDCl$_3$, 400 MHz): 7.60-7.40 (m, 6H), 6.45 (br s, 1H), 5.00 (t, 1H), 4.85 (dt, 1H), 4.10 (d, 1H), 4.00 (dd, 1H), 3.70 (d, 1H), 3.60 (m, 2H), 2.50 (s, 3H), 1.25 (m, 3H).

The following compounds were prepared following a similar method to that described in Example 1: 4-[5-(3,5-Dichloro-phenyl)-5-trifluoromethyl-4,5-dihydro-isoxazol-3-yl]-2-methyl-N-((R)-2-(2-methoxyethyl)-3-oxo-isoxazolidin-4-yl)-benzamide (compound B7) (using 2-bromo-1-methoxy-ethane as alkylating agent in Step A); 4-[5-(3,5-Dichloro-phenyl)-5-trifluoromethyl-4,5-dihydro-isoxazol-3-yl]-2-methyl-N-((R)-2-butyl-3-oxo-isoxazolidin-4-yl)-benzamide (compound B8) (using butyl bromide as alkylating agent in Step A); 4-[5-(3,4,5-Trichloro-phenyl)-5-trifluoromethyl-4,5-dihydro-isoxazol-3-yl]-2-methyl-N-((R)-2-ethyl-3-oxo-isoxazolidin-4-yl)-benzamide (compound C1), 4-[5-(3,5-Dichloro-4-bromo-phenyl)-5-trifluoromethyl-4,5-dihydro-isoxazol-3-yl]-2-methyl-N-((R)-2-ethyl-3-oxo-isoxazolidin-4-yl)-benzamide (compound C2); 4-[5-(3,5-Dichloro-4-fluoro-phenyl)-5-trifluoromethyl-4,5-dihydro-isoxazol-3-yl]-2-methyl-N-((R)-2-ethyl-3-oxo-isoxazolidin-4-yl)-benzamide (compound C3); 4-[5-(3,5-trifluoromethyl-4-chloro-phenyl)-5-trifluoromethyl-4,5-dihydro-isoxazol-3-yl]-2-methyl-N-((R)-2-ethyl-3-oxo-isoxazolidin-4-yl)-benzamide (compound C4); 4-[5-(3-chloro-5-fluoro-phenyl)-5-trifluoromethyl-4,5-dihydro-isoxazol-3-yl]-2-methyl-N-((R)-2-ethyl-3-oxo-isoxazolidin-4-yl)-benzamide (compound C5); 4-[5-(3,5-Dichloro-phenyl)-5-trifluoromethyl-4,5-dihydro-isoxazol-3-yl]-2-methyl-N-((S)-2-ethyl-3-oxo-isoxazolidin-4-yl)-benzamide (Compound E2) (starting from (S)-cycloserine).

When this reaction was carried out to obtain 4-[5-(3,4,5-Trichloro-phenyl)-5-trifluoromethyl-4,5-dihydro-isoxazol-3-yl]-2-methyl-N-((R)-2-ethyl-3-oxo-isoxazolidin-4-yl)-benzamide (compound C1), it was possible to separate the two diastereoisomers by precipitation after the work up. The crude mixture was stirred with diethyl ether and a solid precipitated out of the solution. The solid (enriched in 1 diastereomer) was analysed by chiral HPLC (method K): 9.72 min (93.8%), 16.6 min (06.17%). The filtrate (enriched in the other diastereomer) was also analysed by chiral HPLC (method K): 9.99 min (11.53%), 16.6 min (85.16%).

Similarly when this reaction was carried out to obtain 4-[5-(3,5-Dichloro-4-fluoro-phenyl)-5-trifluoromethyl-4,5-dihydro-isoxazol-3-yl]-2-methyl-N-((R)-2-ethyl-3-oxo-isoxazolidin-4-yl)-benzamide (compound C3), it was possible to separate the two diastereoisomers by precipitation after the work up. The crude mixture was stirred with diethyl ether and a solid precipitated out of the solution. The solid (enriched in 1 diastereomer) was analysed by chiral HPLC (method K): 8.88 min (88.87%), 15.98 min (05.95%). The filtrate (enriched in the other diastereomer) was also analysed by chiral HPLC (method K): 8.61 min (24.10%), 12.25 min (74.49%).

EXAMPLE 5

4-[5-(3,5-Dichloro-phenyl)-5-trifluoromethyl-4,5-dihydro-isoxazol-3-yl]-2-methyl-N-((R)-2-(2-hydroxy-ethyl)-3-oxo-isoxazolidin-4-yl)-benzamide (compound B9)

Step A: ((R)-2-(hydroxy-ethyl)-3-oxo-isoxazolidin-4-yl)-carbamic acid tert-butyl ester

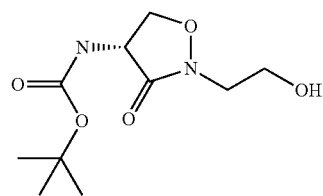 [SMILES: CC(C)(C)OC(=O)N[C@@H]1CON(CCO)C1=O]

(3-Oxo-isoxazolidin-4-yl)-carbamic acid tert-butyl ester (0.2 g, prepared from (D)-cycloserine as described in Chem. Pharm. Bull. 2002, 50(4) 554-557) was dissolved in acetonitrile (20 ml), then potassium carbonate (0.69 g), potassium iodide (0.175 g) and 2-bromoethanol (0.137 g) were added. The reaction was stirred at room temperature for 1 hour. The reaction mixture was partitioned between ethyl acetate and water. The organic layer was washed with water, brine and then dried over sodium sulphate. The solvent was removed in vacuo and the crude product was purified by column chromatography (eluent cyclohexane/ethyl acetate) to afford ((R)-2-(2-hydroxyethyl)-3-oxo-isoxazolidin-4-yl)-carbamic acid tert-butyl ester as a yellow solid. LCMS (method A) 1.05 min, MH$^+$ 259; $^1$H-NMR (CDCl$_3$, 400 MHz): 5.55 (br s, 1H), 4.65 (m, 2H), 4.10 (t, 1H), 3.80 (m, 1H), 3.20 (br s, 1H), 1.50 (s, 9H), 1.20 (m, 3H).

Step B: (R)-4-Amino-2-(2-hydroxyethyl)-isoxazolidin-3-one

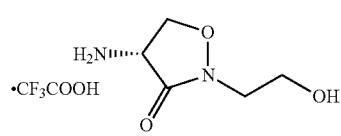

The BOC protecting group was removed as described in Example 3, Step B to afford (R)-4-amino-2-(2-hydroxyethyl)-isoxazolidin-3-one (trifluoroacetic acid salt), which was used directly in the next step.

Step C: 4-[5-(3,5-Dichloro-phenyl)-5-trifluoromethyl-4,5-dihydro-isoxazol-3-yl]-2-methyl-N4R)-2-(2-hydroxyethyl)-3-oxo-isoxazolidin-4-yl)-benzamide

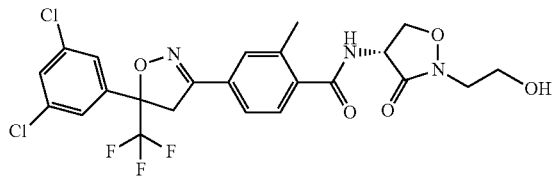 [SMILES: Cc1cc(C2=NOC(c3cc(Cl)cc(Cl)c3)(C(F)(F)F)C2)ccc1C(=O)N[C@@H]1CON(CCO)C1=O]

Amide coupling was performed as described in Example 3, Step C to afford the title compound as a solid (24 mg). M.p. 78° C.; LCMS (Method A) 1.94 min, M–H 544/550.

EXAMPLE 6

4-[5-(3,5-Dichloro-phenyl)-5-trifluoromethyl-4,5-dihydro-isoxazol-3-yl]-2-methyl-N-((R)-2-(thietan-3-yl)-3-oxo-isoxazolidin-4-yl)-benzamide (compound B10)

Step A: ((R)-2-(thietan-3-yl)-3-oxo-isoxazolidin-4-yl)-carbamic acid tert-butyl ester

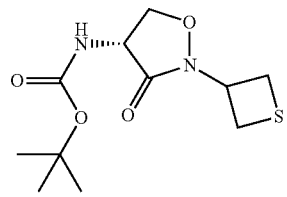 [SMILES: CC(C)(C)OC(=O)N[C@@H]1CON(C2CSC2)C1=O]

A solution of triphenylphosphine (0.79 g) in THF (22 ml) was cooled under argon to −10° C. Diethylazodicarboxylate (DEAD, 1.57 g) was added dropwise then thietan-3-ol (0.4 g) and (3-oxo-isoxazolidin-4-yl)-carbamic acid tert-butyl ester (0.27 g, prepared from (D)-cycloserine as described in Chem. Pharm. Bull. 2002, 50(4) 554-557). The reaction mixture was stirred at room temperature for 24 hours then the solvent was removed in vacuo. The crude product was purified by column chromatography (eluent cyclohexane/ethyl acetate) to afford the title product as a white solid (51 mg). $^1$H-NMR (CDCl$_3$, 400 MHz): 5.45 (q, 1H), 5.05 (m, 1H), 4.90 (m, 1H), 4.50 (t, 1H), 4.10 (dd, 1H), 3.55 (m, 2H), 3.40 (m, 2H), 1.50 (s, 9H).

Step B: (R)-4-Amino-2-(thietan-3-yl)-isoxazolidin-3-one

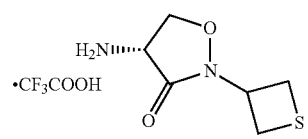 [SMILES: "·CF3COOH" ; N[C@@H]1CON(C2CSC2)C1=O]

Using the product obtained in Step A (43 mg), the BOC protecting group was removed as described in Example 3, Step B to afford the title product, which was used directly in the next step. LCMS (Method A) 0.17 min, M–H 175.

Step C: 4-[5-(3,5-Dichloro-phenyl)-5-trifluoromethyl-4,5-dihydro-isoxazol-3-yl]-2-methyl-N-((R)-2-(thietan-3-yl)-3-oxo-isoxazolidin-4-yl)-benzamide

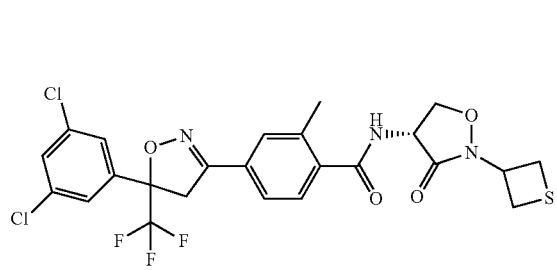 [SMILES: Cc1cc(C2=NOC(c3cc(Cl)cc(Cl)c3)(C(F)(F)F)C2)ccc1C(=O)N[C@@H]1CON(C2CSC2)C1=O]

Amide coupling was performed as described in Example 3, Step C to afford the title compound as a yellow resin (10 mg); LCMS (Method A) 2.13 min, M–H 573/574.

The following compounds were prepared following a similar method to that described in Example 6: 4-[5-(3,5-Dichloro-phenyl)-5-trifluoromethyl-4,5-dihydro-isoxazol-3-yl]-2-methyl-N-((R)-2-(cyclobutyl)-3-oxo-isoxazolidin-4-yl)-benzamide (compound B11); 4-[5-(3,5-Dichloro-phenyl)-5-trifluoromethyl-4,5-dihydro-isoxazol-3-yl]-2-methyl-N-((R)-2-(oxetan-3-yl)-3-oxo-isoxazolidin-4-yl)-benzamide (compound B12)

EXAMPLE 7

General Method for Preparing the Compounds of the Invention in Parallel

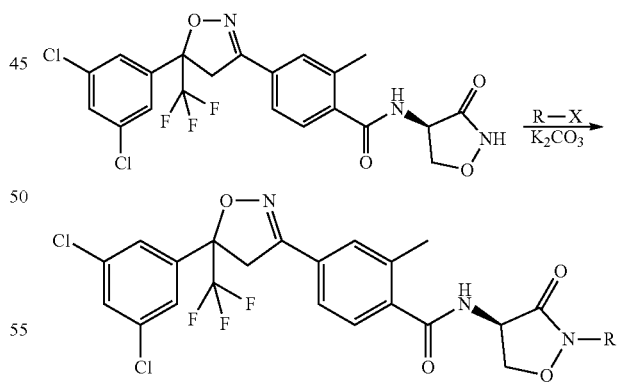

To a solution of 4-[5-(3,5-Dichloro-phenyl)-5-trifluoromethyl-4,5-dihydro-isoxazol-3-yl]-2-methyl-N-((R)-3-oxo-isoxazolidin-4-yl)-benzamide (30 μmol) in N,N-dimethylformamide ("DMF") (0.5 ml) was added a solution of an alkylhalogenide of formula R—X (32 μmmol) in N,N-dimethylformamide ("DMF") (0.3 ml) followed by addition of potassium carbonate (80 μmol). The reaction mixture was stirred at ambient temperature for 16 hours. Then the reaction mixture was separated by HPLC. This method was used to prepare a number of compounds (Compound Nos. B13 to B29 of Table B) in parallel.

EXAMPLE 8

4-[5-(3,5-Dichloro-phenyl)-5-trifluoromethyl-4,5-dihydro-isoxazol-3-yl]-2-methyl-N-(2-oxo-2lambda*4*-[1,2]oxathiolan-4-yl)-benzamide (compound A2)

Step A:
(R)-2-Oxo-2lambda*4*-[1,2]oxathiolan-4-ylamine trifluoroacetic acid salt

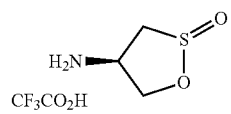

(2-Oxo-2lambda*4*-[1,2]oxathiolan-4-yl)-carbamic acid tert-butyl ester (prepared in 3 steps from L-cystine according to *J. Org. Chem.* 1981, 46, 5408-5413) (345 mg) was dissolved in dichloromethane (7.8 ml) and treated with trifluoroacetic acid (0.36 ml). The reaction mixture was stirred at room temperature overnight and the solvent removed in vacuo to afford (R)-2-Oxo-2lambda*4*-[1,2]oxathiolan-4-ylamine (trifluoroacetic acid salt), which was used directly in the next step. LCMS (Method E) 0.20 min, M+H 122.

Step B: 4-[5-(3,5-Dichloro-phenyl)-5-trifluoromethyl-4,5-dihydro-isoxazol-3-yl]-2-methyl-N-(2-oxo-2lambda*4*-[1,2]oxathiolan-4-yl)-benzamide

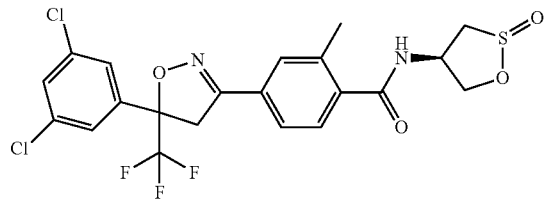 [SMILES: Cc1cc(C2=NOC(c3cc(Cl)cc(Cl)c3)(C(F)(F)F)C2)ccc1C(=O)N[C@@H]1COS(=O)C1]

Oxalyl chloride (0.027 ml) was added to a solution of 4-[5-(3,5-dichloro-phenyl)-5-trifluoromethyl-4,5-dihydro-isoxazol-3-yl]-2-methyl-benzoic acid (100 mg) (prepared according to WO 2009/080250) in dichloromethane (1.2 ml). After addition of two drops of N,N-dimethylformamide ("DMF") the reaction mixture was stirred at ambient temperature for 18 hours. The reaction mixture was concentrated to give the acid chloride as a yellow solid, which was used in the next step without further purification.

To a solution of the acid chloride in dichloromethane were added triethylamine (0.074 mL) followed by (R)-2-Oxo-2lambda*4*-[1,2]oxathiolan-4-ylamine (trifluoroacetic acid salt) (59 mg). The reaction mixture was then stirred at room temperature for 24 hours. The reaction was quenched by adding water and the mixture extracted with ethyl acetate. The combined organic layers were washed with brine, dried (Na$_2$SO$_4$) and evaporated. Purification using reverse phase chromatography afforded 16 mg of a first mixture of 2 diastereomers as an oil, followed by 21 mg of a second mixture of 2 other diastereomers as an oil. Fraction 1: LCMS (Method F) 2.04 min, M−H 519/521. $^1$H-NMR (CDCl$_3$, 400 MHz): 7.56-7.47 (m, 4H), 7.46-7.42 (m, 1H), 7.41-7.34 (m, 1H), 6.24-6.04 (m, 1H), 5.23-5.12 (m, 1H), 4.99 (dd, 1H), 4.75 (dd, 1H), 4.08 (d, 1H), 3.70 (d, 1H), 3.34 (d, 1H), 3.09 (d, 1H, J=6.6 Hz), 2.50 (s, 3H). Fraction 2: LCMS (Method) min, M−H 519/521. $^1$H-NMR (CDCl$_3$, 400 MHz): 7.58-7.39 (m, 6H), 5.48-5.37 (m, 1H), 4.88 (d, 1H), 4.62 (d, 1H), 4.08 (d, 1H), 3.70 (d, 1H), 3.63-3.54 (m, 1H), 3.31 (d, 1H), 2.46 (s, 3H).

EXAMPLE 9

4-[5-(3,5-Dichloro-phenyl)-5-trifluoromethyl-4,5-dihydro-isoxazol-3-yl]-N-(2-ethyl-1,1-dioxo-1lambda*6*-isothiazolidin-4-ylmethyl)-2-methyl-benzamide (compound D1)

Step A: N-(3-Benzyloxy-2-hydroxy-propyl)-N-ethyl-methanesulfonamide

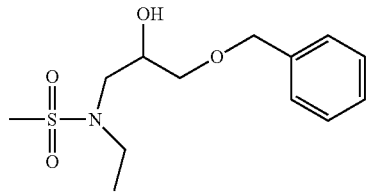 [SMILES: CCN(CC(O)COCc1ccccc1)S(C)(=O)=O]

Triethylamine (0.043 ml, 0.1 equiv) was added to a mixture of N-ethylmethanesulfonamide (413 mg, 1.1 equiv) and 2-benzyloxymethyloxirane (500 mg, 3.04 mmol) prepared according to (*J. Am. Chem. Soc.*, 1996, 118, 7094-7100) in anhydrous dioxane (1 ml). The reaction mixture was then heated to 50° C. overnight. As the reaction was not complete, it was heated to 100° C. for another 5 hours (reaction complete according to TLC). The volatiles were then removed in vacuo. Flash chromatography eluting with cyclohexane/Ethyl acetate (6/4 then 1/1) afforded 836 mg (2.91 mmol, 96%). LCMS (Method E) 1.44 min, M+H 288. $^1$H-NMR (CDCl$_3$, 400 MHz): 7.43-7.27 (m, 5H), 4.57 (s, 2H), 4.11-3.90 (m, 1H), 3.62-3.44 (m, 2H), 3.43-3.20 (m, 4H), 2.90 (s, 3H), 1.14-1.33 (m, 3H).

Step B: 4-Benzyloxymethyl-2-ethyl-isothiazolidine 1,1-dioxide

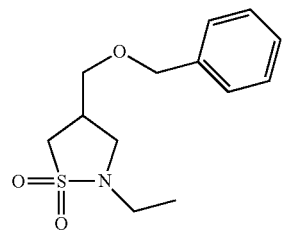 [SMILES: CCN1CC(COCc2ccccc2)CS1(=O)=O]

Benzenesulfonyl chloride (0.41 ml, 1.1 equiv) was added to a solution of N-(3-Benzyloxy-2-hydroxy-propyl)-N-ethyl-methanesulfonamide (836 mg, 2.91 mmol) in pyridine (5.8 ml). The reaction mixture was then heated to 50° C. for 24 hours. Ethyl acetate was added and a precipitate (pyridinium hydrochloride salt) formed. It was filtered and the residue was diluted in ethyl acetate. The organic phase was then washed with 1M aqueous HCl, water, CuSO$_4$ aqueous solution and NaHCO$_3$ saturated aqueous solution. The organic phase was then dried (Na$_2$SO$_4$) and evaporated.

To a solution of the aforementioned residue (2.61 mmol) in anhydrous tetrahydrofuran at −78° C. was added n-BuLi (5.4 mL, 2.5 equiv). The reaction mixture was then allowed to warm up to 0° C. and stirred at this temperature for 2 hours. It was quenched by addition of saturated aqueous NH$_4$Cl. The reaction mixture was then extracted with ethyl acetate. The combined organic phases were washed with brine, dried (Na$_2$SO$_4$) and evaporated. Flash chromatography eluting with cyclohexane/Ethyl acetate (7/3) afforded 274 mg (1.017 mmol, 40%). LCMS (Method E) 1.59 min, M+H 270. $^1$H-NMR (CDCl$_3$, 400 MHz): 7.40-7.27 (m, 5H), 4.60-4.45 (m, 2H), 3.54 (dd, 2H), 3.37-3.20 (m, 2H), 3.17-2.85 (m, 5H), 1.22 (t, 3H).

Step C: (2-Ethyl-1,1-dioxo-1lambda*6*-isothiazolidin-4-yl)-methanol

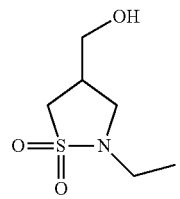

A mixture of 4-Benzyloxymethyl-2-ethyl-isothiazolidine 1,1-dioxide (254 mg) and Pd/C (108 mg, 0.1 equiv) in methanol was purged with H$_2$ and left to stir under an H$_2$ atmosphere for 24 h. As LCMS indicated completion, the reaction mixture was filtered through a pad of silica (rinsing with MeOH). The filtrate was evaporated and 162 mg of the expected alcohol were obtained. It was pure enough to be used as such in the next step. LCMS (Method E) 0.25 min, M+H 170. $^1$H-NMR (CDCl$_3$, 400 MHz): 3.8-3.70 (m, 2H), 3.39-3.25 (m, 2H), 3.20-3.01 (m, 4H), 2.94-2.78 (m, 1H), 1.24 (t, 3H).

Step D: 2-(2-Ethyl-1,1-dioxo-1lambda*6*-isothiazolidin-4-ylmethyl)-isoindole-1,3-dione

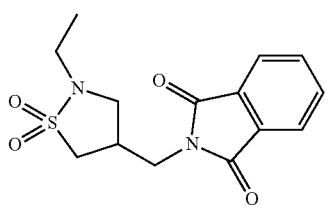 [SMILES: CCN1CC(CN2C(=O)c3ccccc3C2=O)CS1(=O)=O]

To a stirred solution of phthalimide (133 mg, 1 equiv) in tetrahydrofuran (4.5 ml) was added triphenylphosphine (237 mg, 1 equiv) and (2-Ethyl-1,1-dioxo-1lambda*6*-isothiazolidin-4-yl)-methanol (0.905 mmol). This solution was cooled down to 0° C. for the dropwise addition of diisopropylazodicarboxylate (0.18 ml, 1 equiv). The reaction mixture was stirred at room temperature over the weekend. It was then concentrated, and stirred in diethyl ether for 5 hours. Volatiles were removed in vacuo. Flash chromatography eluting with cyclohexane/ethyl acetate (7/3) afforded 261 mg (0.85 mmol, 94%). LCMS (Method E) 1.40 min, M+H 309. $^1$H-NMR (CDCl$_3$, 400 MHz): 7.93-7.84 (m, 2H), 7.83-7.72 (m, 2H), 3.89 (dd, 2H), 3.41-3.23 (m, 2H), 3.17-2.98 (m, 5H), 1.22 (t, 3H).

Step E: C-(2-Ethyl-1,1-dioxo-1lambda*6*-isothiazolidin-4-yl)-methylamine

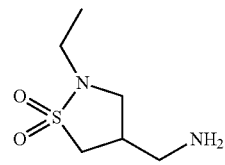

To a solution of 2-(2-Ethyl-1,1-dioxo-1lambda*6*-isothiazolidin-4-ylmethyl)-isoindole-1,3-dione (261 mg, 0.85 mmol) in EtOH (4 ml) was added hydrazine monohydrate (0.165 ml, 4 equiv). The reaction mixture was then refluxed overnight and a white gum formed. The reaction mixture was filtered (rinsing several times with EtOH) and the filtrate was evaporated to afford 81 mg of the expected amine contaminated by 10% of 2,3-Dihydro-phthalazine-1,4-dione. It was used as such in the next step.

$^1$H-NMR (MeOD, 400 MHz): 3.52-3.36 (m, 2H), 3.20-2.97 (m, 4H), 2.92-2.83 (m, 2H), 2.83-2.69 (m, 1H), 1.26 (t, 3H).

Step F: 4-[5-(3,5-Dichloro-phenyl)-5-trifluoromethyl-4,5-dihydro-isoxazol-3-yl]-N-(2-ethyl-1,1-dioxo-1lambda*6*-isothiazolidin-4-ylmethyl)-2-methyl-benzamide

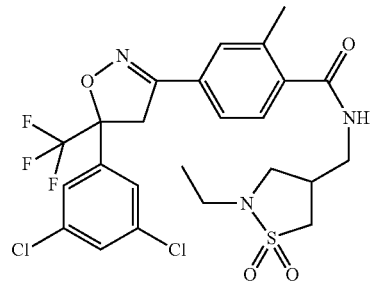 [SMILES: CCN1CC(CNC(=O)c2ccc(C3=NOC(c4cc(Cl)cc(Cl)c4)(C(F)(F)F)C3)cc2C)CS1(=O)=O]

Oxalyl chloride (0.027 ml) was added to a solution of 4-[5-(3,5-dichloro-phenyl)-5-trifluoromethyl-4,5-dihydro-isoxazol-3-yl]-2-methyl-benzoic acid (100 mg) (prepared according to WO 2009/080250) in dichloromethane (1.2 ml). After addition of two drops of N,N-dimethylformamide ("DMF") the reaction mixture was stirred at ambient temperature for 18 hours. The reaction mixture was concentrated to give the acid chloride as a yellow solid, which was used in the next step without further purification.

To a solution of the acid chloride in dichloromethane were added triethylamine (0.037 ml) followed by (C-(2-Ethyl-1,1-dioxo-1lambda*6*-isothiazolidin-4-yl)-methylamine (45 mg). The reaction mixture was then stirred at room temperature for 24 hours. The reaction was quenched by adding water and the mixture extracted with ethyl acetate. The combined organic layers were washed with brine, dried (Na$_2$SO$_4$) and evaporated. Purification using reverse phase chromatography afforded 18 mg of a mixture of two diastereomers as an oil. LCMS (Method D) 2.21 min, M+H 578/580. $^1$H-NMR (CDCl$_3$, 400 MHz): 7.56-7.49 (m, 4H), 7.47-7.40 (m, 2H), 6.23-6.32 (m, 1H), 4.09 (d, 1H), 3.74-3.53 (m, 3H), 3.46-3.27 (m, 2H), 3.17-3.00 (m, 5H), 2.47 (s, 3H), 1.23 (t, 3H).

EXAMPLE 10

4-[5-(3,5-Dichloro-phenyl)-5-trifluoromethyl-4,5-dihydroisoxazol-3-yl]-N-(2-ethyl-isoxazolidin-4-yl)-2-methyl-benzamide (compound A3)

Step A: 2-[4-(2-Nitro-benzenesulfonylamino)-isoxazolidine-2-carbonyl]-benzoic acid methyl ester

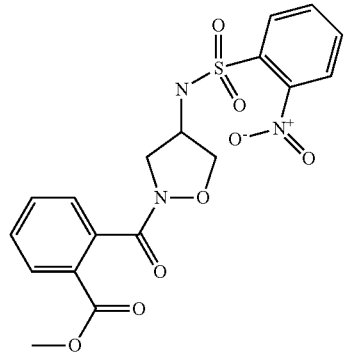 [SMILES: COC(=O)c1ccccc1C(=O)N1CC(NS(=O)(=O)c2ccccc2[N+](=O)[O-])CO1]

Triethylamine (0.11 ml, 0.1 equiv) was added to a mixture of N-hydroxyphthalimide (1.13 g, 6.9 mmol) and 2-Bromomethyl-1-(2-nitro-benzenesulfonyl)-aziridine (7.6 mmol, 1.1 equiv) (prepared according to *Org. Biomol. Chem.* 2008, 6, 1902-1904) in anhydrous dioxane (4.5 ml). The reaction mixture was then heated to 50° C. over the weekend. Then methanol (2.5 ml) and triethylamine (1.1 ml, 1 equiv) were added and the reaction mixture was heated at 50° C. for another 4 hours. Volatiles were then removed in vacuo. Flash chromatography eluting with cyclohexane/ethyl actetate (1/1 then 3/7) afforded 2.46 g of the title compound (5.67 mmol, 74%). LCMS (Method E) 1.55 min, M+H 435. $^1$H-NMR (CDCl$_3$, 400 MHz): 8.21-8.11 (m, 1H), 8.00 (d, 1H), 7.90-7.67 (m, 3H), 7.63-7.56 (m, 1H), 7.55-7.46 (m, 1H), 7.41 (d, 1H), 6.87-6.73 (m, 1H), 4.77-4.67 (m, 1H), 4.22-3.95 (m, 5H), 3.93-3.75 (m, 2H).

Step B: 2-(4-Amino-isoxazolidine-2-carbonyl)-benzoic acid methyl ester

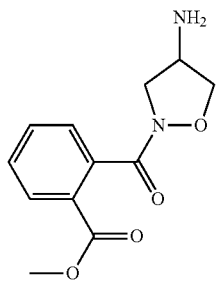 [SMILES: COC(=O)c1ccccc1C(=O)N1CC(N)CO1]

A solution of 2-[4-(2-Nitro-benzenesulfonylamino)-isoxazolidine-2-carbonyl]-benzoic acid methyl ester (200 mg, 0.46 mmol) and PhSH (0.035 ml, 1.1 equiv) in acetonitrile (2.3 ml) under argon at rt was treated with K$_2$CO$_3$ (95 mg, 1.5 equiv). The reaction mixture turned bright yellow. The reaction was left to stir overnight. As TLC indicated complete consumption of starting material, volatiles were removed in vacuo. Flash column chromatography eluting with dichloromethane:methanol (9/1) afforded 85 mg of the expected amine (0.34 mmol, 74%). LCMS (Method E) 0.55 and 1.41 min, M+H 251. $^1$H-NMR (CDCl$_3$, 400 MHz): 7.95 (d, 1H), 7.63-7.52 (m, 1H), 7.51-7.36 (m, 2H), 4.17-3.92 (m, 3H), 3.87 (s, 3H), 3.80-3.55 (m, 2H), 2.04-1.75 (m, 2H).

Step C: 2-(4-{4-[5-(3,5-Dichloro-phenyl)-5-trifluoromethyl-4,5-dihydro-isoxazol-3-yl]-2-methyl-benzoylamino}-isoxazolidine-2-carbonyl)-benzoic acid methyl ester

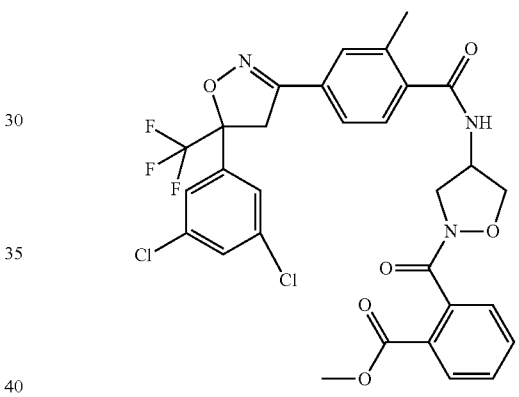

Oxalyl chloride (0.037 ml) was added to a solution of 4-[5-(3,5-dichloro-phenyl)-5-trifluoromethyl-4,5-dihydro-isoxazol-3-yl]-2-methyl-benzoic acid (135 mg) (prepared according to WO 2009/080250) in dichloromethane (1.6 ml). After addition of two drops of N,N-dimethylformamide ("DMF") the reaction mixture was stirred at ambient temperature for 18 hours. The reaction mixture was concentrated to give the acid chloride as a yellow solid, which was used in the next step without further purification.

To a solution of the acid chloride in dichloromethane (3.2 ml) were added triethylamine (0.090 ml) followed by 2-(4-Amino-isoxazolidine-2-carbonyl)-benzoic acid methyl ester (85 mg). The reaction mixture was then stirred at room temperature for 24 hours. The reaction was quenched by adding water and the mixture extracted with ethyl acetate. The combined organic layers were washed with brine, dried (Na$_2$SO$_4$) and evaporated. Flash column chromatography eluting with cyclohexane/EtOAc (1/1) afforded 187 mg the expected amine as a mixture of (separable) diastereomers (0.29 mmol, 90%). LCMS (Method F) 2.11 and 2.15 min, M−H 648/650. $^1$H-NMR (CDCl$_3$, 400 MHz): 7.96 (d, 1H), 7.81-7.68 (m, 1H), 7.68-7.60 (m, 1H), 7.60-7.42 (m, 8H), 5.39-5.42 (m, 1H), 4.57-4.43 (m, 1H), 4.31-4.24 (m, 1H), 4.08 (d, 1H), 4.01-3.88 (m, 1H), 3.87-3.78 (m, 1H), 3.72 (d, 1H), 3.62 (s, 3H), 2.52 (s, 3H).

Step D: 4-(2-Nitro-benzenesulfonylamino)-isoxazolidine-2-carboxylic acid tert-butyl ester

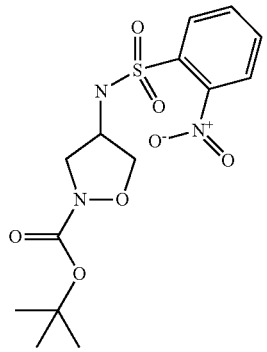 [SMILES: CC(C)(C)OC(=O)N1CC(NS(=O)(=O)c2ccccc2[N+](=O)[O-])CO1]

2-[4-(2-Nitro-benzenesulfonylamino)-isoxazolidine-2-carbonyl]-benzoic acid methyl ester (2.67 g, 6.14 mmol) was suspended in 20 ml 2M aqueous HCl and the mixture was refluxed for 48 hours. It was then filtered and the solids were washed with water. The filtrate was then evaporated and dried under vacuum. The residue was triturated in i-PrOH. The solid was filtered and the filtrate evaporated. This filtrate (177 mg) was used as such without further purification. LCMS (Method E) 0.87 and 0.95 min, M+H 274.

A suspension of the aforementioned residue in MeCN (30 ml) was treated with Et₃N (3.62 ml, 4.2 equiv) and the reaction mixture turned clear. Then Boc₂O (2.01 g, 1.5 equiv) was added and the reaction mixture was left to stir under argon at rt for 36 hours. It was quenched by addition of water and extracted with EtOAc. The combined organic extracts were dried (Na₂SO₄) and evaporated. Flash chromatography eluting with cyclohexane/ethyl acetate (6/4) afforded 1.69 g (4.52 mmol, 74%). LCMS (Method D) 1.66 min, M+Na 396. ¹H-NMR (CDCl₃, 400 MHz): 8.18-8.13 (m, 1H), 7.95-7.88 (m, 1H), 8.85-7.74 (m, 2H), 5.78 (d, 1H), 4.54-4.42 (m, 1H), 3.95 (dd, 1H), 3.91-3.80 (m, 2H), 3.49 (dd, 1H), 1.49 (s, 9H).

Step E: 4-Amino-isoxazolidine-2-carboxylic acid tert-butyl ester

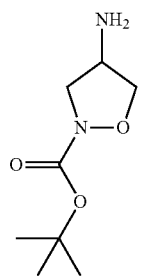

A solution of 4-(2-Nitro-benzenesulfonylamino)-isoxazolidine-2-carboxylic acid tert-butyl ester (694 mg, 1.86 mmol) and PhSH (0.142 ml, 1.1 equiv) in MeCN (10 ml) under argon at room temperature was treated with K₂CO₃ (386 mg, 1.5 equiv). The reaction mixture turned bright yellow. The reaction was left to stir overnight. As TLC indicated complete consumption of starting material, volatiles were removed in vacuo. Flash column chromatography eluting with dichloromethane:methanol (10/0 then 9/1) afforded 336 mg of the title amine (1.8 mmol, 96%). ¹H-NMR (CDCl₃, 400 MHz): 4.03-3.92 (m, 3H), 3.89-3.76 (m, 1H), 3.70 (dd, 1H), 3.37 (dd, 1H), 1.51 (s, 9H).

Step F: 4-{4-[5-(3,5-Dichloro-phenyl)-5-trifluoromethyl-4,5-dihydro-isoxazol-3-yl]-2-methyl-benzoylamino}-isoxazlidine-2-carboxylic acid tert-buty ester

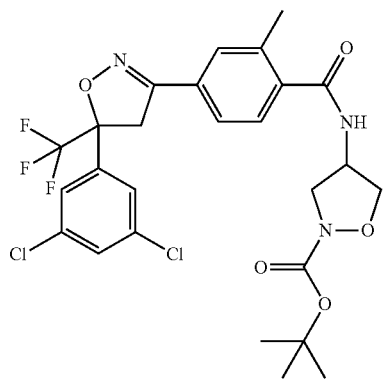 [SMILES: Cc1cc(C2=NOC(c3cc(Cl)cc(Cl)c3)(C(F)(F)F)C2)ccc1C(=O)NC1CON(C(=O)OC(C)(C)C)C1]

Oxalyl chloride (0.20 ml) was added to a solution of 4-[5-(3,5-dichloro-phenyl)-5-trifluoromethyl-4,5-dihydro-isoxazol-3-yl]-2-methyl-benzoic acid (749 mg) (prepared according to WO 2009/080250) in dichloromethane (9 ml). After addition of two drops of N,N-dimethylformamide ("DMF") the reaction mixture was stirred at ambient temperature for 18 hours. The reaction mixture was concentrated to give the acid chloride as a yellow solid, which was used in the next step without further purification.

To a solution of the acid chloride in dichloromethane (18 ml) were added triethylamine (0.30 ml) followed by 4-Amino-isoxazolidine-2-carboxylic acid tert-butyl ester (336 mg). The reaction mixture was then stirred at room temperature for 24 hours. The reaction was quenched by adding water and the mixture extracted with ethyl acetate. The combined organic layers were washed with brine, dried (Na₂SO₄) and evaporated. Flash column chromatography eluting with cyclohexane/EtOAc (1/1) afforded 197 mg the expected amine as a mixture of diastereomers.

¹H-NMR (CDCl₃, 400 MHz): 7.60-7.48 (m, 4H), 7.47-7.36 (m, 2H), 6.23.6.15 (m, 1H), 5.08-4.98 (m, 1H), 4.20-3.94 (m, 4H), 3.70 (d, 1H), 3.66-3.58 (m, 1H), 2.48 (s, 3H), 1.50 (s, 9H).

Step G: 4-[5-(3,5-Dichloro-phenyl)-5-trifluoromethyl-4,5-dihydro-isoxazol-3-yl]-N-isoxazolidin-4-yl-2-methyl-benzamide trifluoroacetic acid salt

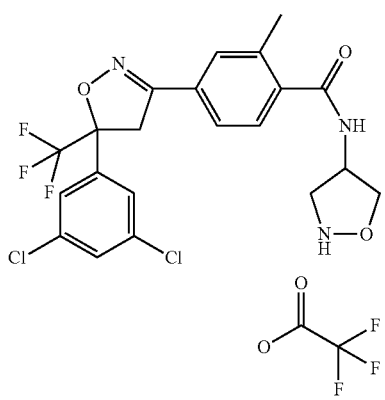

To a solution of 4-{4-[5-(3,5-Dichloro-phenyl)-5-trifluoromethyl-4,5-dihydro-isoxazol-3-yl]-2-methyl-benzoylamino}-isoxazlidine-2-carboxylic acid tert-butyl ester (198 mg, 0.34 mmol) in dichloromethane (1.7 ml) was added trifluoroacetic acid (0.15 ml, 5 equiv). The reaction mixture immediately turned black. The reaction mixture was left to stir for 6 hours. Volatiles were then removed in vacuo. Flash column chromatography eluting with ethyl acetate/methanol (10/0 to 9/1) afforded 92 mg of the expected compound as a mixture of diastereomers. LCMS (Method E) 1.93 min, M+H 488/490.

Step H: 4-[5-(3,5-Dichloro-phenyl)-5-trifluoromethyl-4,5-dihydro-isoxazol-3-yl]-N-(2-ethyl-isoxazolidin-4-yl)-2-methyl-benzamide

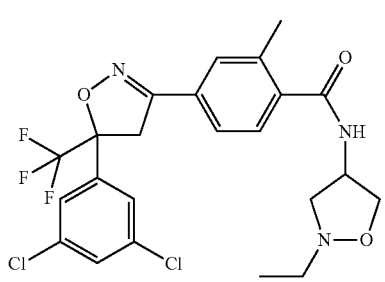 [SMILES: CCN1CC(NC(=O)c2ccc(C3=NOC(c4cc(Cl)cc(Cl)c4)(C(F)(F)F)C3)cc2C)CO1]

Crude 4-[5-(3,5-Dichloro-phenyl)-5-trifluoromethyl-4,5-dihydro-isoxazol-3-yl]-N-isoxazolidin-4-yl-2-methyl-benzamide trifluoroacetic acid salt (0.16 mmol) was dissolved in MeOH (0.8 ml). Then acetaldehyde (0.090 ml, 10 equiv) was added at 0° C. under an argon atmosphere. After stirring for 1 hour at 0° C., NaBH₃CN (20 mg, 2 equiv) was added. The reaction mixture was left to stir over the weekend. It was then evaporated. Flash column chromatography eluting with ethyl acetate/methanol (10/0 to 9/1) afforded 7.5 mg of the expected compound as a mixture of diastereomers. LCMS (Method E) 2.02 min, M+H 516/518. ¹H-NMR (MeOD, 400 MHz): 7.70-7.53 (m, 5H), 7.52-7.37 (m, 1H), 4.92-4.85 (m, 1H), 4.40-4.22 (m, 2H), 4.00 (d, 1H), 3.83-3.62 (m, 1H), 3.29-2.52 (m, 4H), 2.43 (s, 3H), 1.16 (t, 3H).

EXAMPLE 11

4-[5-(3,5-dichlorophenyl)-5-(trifluoromethyl)-4H-isoxazol-3-yl]-2-methyl-N-[(2-oxido-1,3,2-dioxathiolan-2-ium-4-yl)methyl]benzamide (Compound F5)

Step A: Preparation of 4-[5-(3,5-dichloro-phenyl)-5-methyl-4,5-dihydro-isoxazol-3-yl]-N-(2,3-dihydroxy-propyl)-2-methylbenzamide

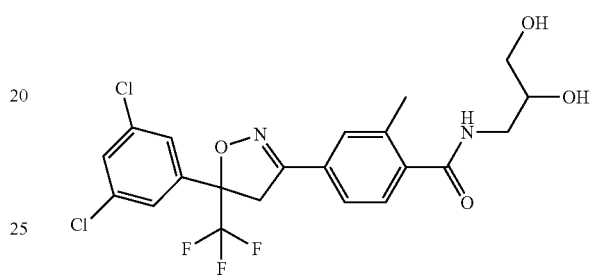

A solution of 10% Sulfuric acid (0.1 ml) and 4-[5-(3,5-dichloro-phenyl)-5-methyl-4,5-dihydro-isoxazol-3-yl]-N-(2,2-dimethyl-[1,3]dioxolane-4-ylmethyl)-2-methylbenzamide (1 g, 1.9 mmol) in methanol (50 ml) was stirred at 70° C. for 4 hours. The solvent was evaporated and the crude mixture was diluted with ethyl acetate (100 ml), washed with a saturated aqueous solution of sodium hydrogencarbonate (20 ml×2) and then with water (50 ml). The combined organic extracts were dried over sodium sulfate and concentrated in vacuo to give the title compound as a solid (0.7 g). M.p. 98-98° C. LCMS (Method G) 3.65 min, MH⁺ 491. ¹HNMR (CDCl₃, 400 MHz): 7.37-7.49 (m, 6H), 6.59 (t, 1H), 4.12 (d, 1H), 3.88 (m, 1H), 3.67 (d, 1H), 3.60 (m, 4H), 2.41 (s, 3H).

Step B: Preparation of 4-[5-(3,5-dichlorophenyl)-5-(trifluoromethyl)-4H-isoxazol-3-yl]-2-methyl-N-[2-oxido-1,3,2-dioxathiolan-2-ium-4-yl)methyl]benzamide

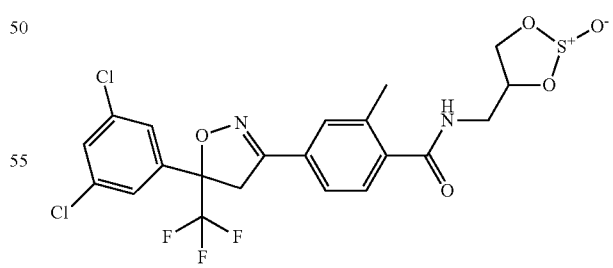

A solution of 4-[5-(3,5-dichloro-phenyl)-5-methyl-4,5-dihydro-isoxazol-3-yl]-N-(2,3-dihydroxy-propyl)-2-methylbenzamide (100 mg, 0.2 mmol) in dichloromethane (10 ml) was cooled to 0° C., treated with Pyridine (0.08 ml, 1.0 mmol) and thionyl chloride (0.03, 0.4 mmol), and stirred for 6 hours. The mixture was diluted with dichloromethane (50 ml), neutralized with 2N hydrochloric acid and washed with water (50 ml). The organic layer was separated, dried over sodium sulfate and concentrated to give the title compound (65 mg) as a mixture of diastereoisomers. Purification by preparative HPLC gave the diastereoisomer 1 (28 mg) and the diastereoisomer 2 (18 mg);

Diastereoisomer 1: LCMS (Method G) 4.07 min, MH$^+$ 536. $^1$HNMR (CDCl$_3$, 400 MHz): 7.37-7.50 (m, 6H), 6.26 (m, 1H), 5.16 (m, 1H), 4.79 (m, 1H), 4.32 (m, 1H), 4.10 (m, 2H), 3.71 (m, 2H), 2.45 (s, 3H).

Diastereoisomer 2: LCMS (Method G) 4.17 min, MH$^+$ 536. $^1$HNMR (CDCl$_3$, 400 MHz): 7.47-7.52 (m, 5H), 7.42 (s, 1H), 6.58 (m, 1H), 4.88 (m, 1H), 4.59 (m, 1H), 4.47 (m, 1H), 4.10 (m, 2H), 3.75 (m, 2H), 2.45 (s, 3H).

EXAMPLE 12

N-(2-Benzyl-isoxazolidin-5-ylmethyl)-4-[5-(3,5-dichloro-phenyl)-5-trifluoromethyl-4,5-dihydro-isoxazol-3-yl]-2-methyl-benzamide (compound F1)

Step A:
(2-Benzyl-isoxazolidin-5-ylmethyl)-carbamic acid tert-butyl ester

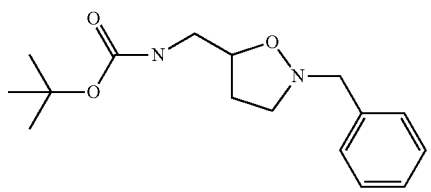 [SMILES: CC(C)(C)OC(=O)NCC1CCN(Cc2ccccc2)O1]

Following the procedure described in Tetrahedron 55, 1999, 4685-4698, N—BOC-allylamine (2 g) was dissolved in toluene (130 ml) and ethanol (45 ml) then benzylhydroxylamine hydrochloride (3.05 g), paraformaldehyde (3.16 g) and triethylamine (1.93 g) were added. The reaction mixture was allowed to stir at room temperature for 24 hours, then the solvent was evaporated in vacuo. The resulting residue was diluted in ethyl acetate and the hydrochloride salt of triethylamine was filtered off. The filtrate was concentrated in vacuo and the residue purified by column chromatography (ethyl acetate/cyclohexane 1:1) to afford the title compound as a colorless oil (4.37 g). LCMS (Method F) 1.53 min, M+H 293.

Step B: C-(2-Benzyl-isoxazolidin-5-yl)-methylamine

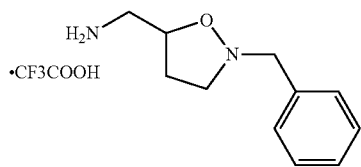 [SMILES: NCC1CCN(Cc2ccccc2)O1]

A solution of (2-benzyl-isoxazolidin-5-ylmethyl)-carbamic acid tert-butyl ester (Step A, 0.5 g) in dichloromethane (10 ml) was treated with trifluoroacetic acid (1.95 g). The solution was stirred at room temperature for 4 hours then concentrated in vacuo to afford the crude title product, which was used directly for the next step. LCMS (Method F) 0.20 min, M+H 194.

Step C: N-(2-Benzyl-isoxazolidin-5-ylmethyl)-4-[5-(3,5-dichloro-phenyl)-5-trifluoromethyl-4,5-dihydro-isoxazol-3-yl]-2-methyl-benzamide

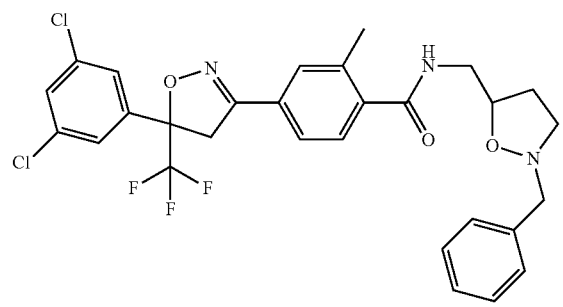 [SMILES: Cc1cc(C2=NOC(c3cc(Cl)cc(Cl)c3)(C(F)(F)F)C2)ccc1C(=O)NCC1CCN(Cc2ccccc2)O1]

To a stirred solution of 4-[5-(3,5-dichloro-phenyl)-5-trifluoromethyl-4,5-dihydro-isoxazol-3-yl]-2-methyl-benzoic acid (1.75 g) (prepared according to WO 2009/080250) in acetonitrile (35 ml) and triethylamine (2.04 ml) were added under nitrogen atmosphere TBTU (1.61 g), AZA.HOBT (0.68 g) and C-(2-Benzyl-isoxazolidin-5-yl)-methylamine (Step B, 1.61 g) were added. The resulting solution was stirred at room temperature for 4 hours, then quenched by addition of aqueous saturated ammonium chloride solution. The mixture was then extracted with ethyl acetate, dried over sodium sulfate, filtered then concentrated in vacuo. The residue purified by column chromatography (ethyl acetate/cyclohexane 1:1) to afford the title compound as a white solid (60 mg, (mixture of diastereoisomers). LCMS (Method F) 2.20 min, M+H 636/638.

The following compound was prepared following a similar method to that described in Example 12: N-(2-methyl-isoxazolidin-5-ylmethyl)-4-[5-(3,5-dichloro-phenyl)-5-trifluoromethyl-4,5-dihydro-isoxazol-3-yl]-2-methyl-benzamide (compound F2).

EXAMPLE 13

4-[5-(3,5-Dichloro-phenyl)-5-trifluoromethyl-4,5-dihydro-isoxazol-3-yl]-2-methyl-N-[3-oxo-2-ethyl-isoxazolidin-5-ylmethyl]-benzamide (compound F3)

Step A:
(3-Bromo-4,5-dihydro-isoxazol-5-ylmethyl)-carbamic acid tert-butyl ester

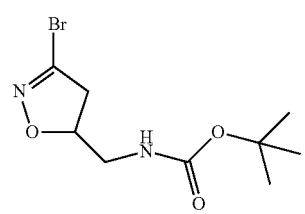

Following the procedure described in Tetrahedron 46, 1990, 1975-1986, N—BOC-allylamine (1.8 g) was dissolved in ethyl acetate and treated with sodium hydrogenocarbonate (4.38 g) and dibromoformaldoxime (2.55 g). The reaction mixture was stirred at room temperature for 4 hours, then poured into water, extracted with ethyl acetate, the organic layer was dried over sodium sulfate and the solvent removed in vacuo. The title crude product was thus obtained as a colorless oil (3.16 g). LCMS (Method F) 1.48 min, M+H 179/181 (M-BOC).

Step B: (3-Oxo-isoxazolidin-5-ylmethyl)-carbamic acid tert-butyl ester

Following the procedure described in Tetrahedron 46, 1990, 1975-1986, the crude product obtained in Step A (1.5 g) was dissolved in THF and treated with 1N aqueous sodium hydroxide (150 ml) in the presence of tetrabutyl ammonium sulfate (0.54 g). After 24 hours stirring at room temperature, aqueous sodium hydroxide (1N, 50 ml) was added again and the reaction mixture stirred for another 48 hours at 60° C. The reaction mixture was then cooled to room temperature, extracted with diethyl ether and the pH of the aqueous layer adjusted to 1 by addition of 2N HCL. The aqueous layer was then extracted with ethyl acetate, the organic layers were combined, dried over sodium sulfate and the solvents removed in vacuo. Column chromatography (ethyl acetate/cyclohexane 1:1) afforded the title product as a white solid (220 mg). LCMS (Method F) 1.06 min, M+H 217. $^1$HNMR (CDCl$_3$, 400 MHz): 4.90 (m, 1H), 4.70 (m, 1H), 3.40 (m, 2H), 2.75 (dd, 1H), 2.60 (dd, 1H), 1.50 (s, 9H).

Step C: (2-Ethyl-3-oxo-isoxazolidin-5-ylmethyl)-carbamic acid tert-butyl ester

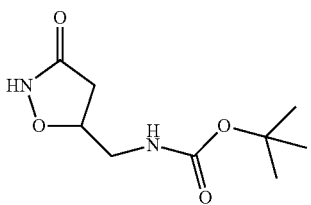

The product obtained in Step B (0.1 g) was alkylated with bromoethane as described in Example 4, step A to afford the O-alkylated product (18 mg), $^1$HNMR (CDCl$_3$, 400 MHz): 4.90 (m, 1H), 4.70 (m, 1H), 4.2 (q, 2H), 3.35 (m, 2H), 3.00 (dd, 1H), 2.75 (dd, 1H), 1.50 (s, 9H), 1.35 (t, 3H); and the title N-alkylated product (63 mg). $^1$HNMR (CDCl$_3$, 400 MHz): 4.85 (m, 1H), 4.55 (m, 1H), 3.60 (m, 2H), 3.40 (m, 2H), 2.80 (dd, 1H), 2.60 (dd, 1H), 1.50 (s, 9H), 1.20 (t, 3H).

Step D: 5-Aminomethyl-2-ethyl-isoxazolidin-3-one

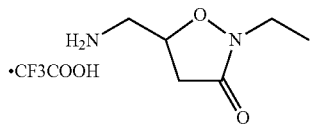

A solution of the product obtained in Step C in dichloromethane (2 ml) was treated with trifluoroacetic acid (0.15 g). The solution was stirred at room temperature for 4 hours then concentrated in vacuo to afford the crude title product, which was used directly for the next step. LCMS (Method F) 0.18 min, M+H 145.

Step E: 4-[5-(3,5-Dichloro-phenyl)-5-trifluoromethyl-4,5-dihydro-isoxazol-3-yl]-2-methyl-N-[3-oxo-2-ethyl-isoxazolidin-5-ylmethyl]-benzamide 4-[5-(3,5-Dichloro-phenyl)-5-trifluoromethyl-4,5-dihydro-isoxazol-3-yl]-2-methyl-benzoic acid (0.3 g) (prepared according to WO 2009/080250) was coupled with the amine obtained in Step D (0.12 g) as described in Example 12, Step C to afford the title product as a beige solid (62 mg, mixture of diasteroisomers). LCMS (Method F) 2.02 min, M+H 542/544.

The following compound was prepared following a similar method to that described in Example 13: 4-[5-(3,5-Dichlorophenyl)-5-trifluoromethyl-4,5-dihydro-isoxazol-3-yl]-2-methyl-N-[3-oxo-2-(1,1,1-trifluoroethyl)-isoxazolidin-5-ylmethyl]-benzamide (compound F4).

EXAMPLE 14

4-[5-(3,5-Dichloro-phenyl)-5-trifluoromethyl-4,5-dihydro-isoxazol-3-yl]-N-[2-(4-methoxy-phenyl)-1,1-dioxo-1lambda*6*-isothiazolidin-5-ylmethyl]-2-methyl-benzamide (compound F6)

Step A: 2-Nitrilo-ethanesulfonic acid (4-methoxy-phenyl)-amid

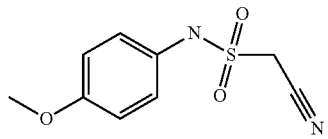

To a solution of para-anisidine (1.95 g) in acetonitrile (25 ml) at 15° C. under argon atmosphere was added pyridine (1.25 g), then cyanomethanesulfonyl chloride (2 g) and the reaction mixture was stirred at room temperature for 1 hour. The reaction mixture was poured into 50 ml water and the pH was made basic by addition of 1N aqueous sodium hydroxide. The aqueous layer was extracted with ethyl acetate, the combined organic layers were dried over sodium sulfate, then concentrated in vacuo. Column chromatography (ethyl acetate/cyclohexane 1:1) afforded the title product as an orange solid (590 mg). $^1$HNMR (CDCl$_3$, 400 MHz): 7.30 (d, 2H), 6.95 (d, 2H), 6.70 (m, 1H), 3.95 (s, 2H), 3.85 (s, 3H).

Step B: 2-(4-Methoxy-phenyl)-1,1-dioxo-1lambda*6*-isothiazolidine-5-carbonitrile

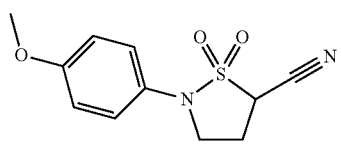 [SMILES: COc1ccc(N2CCC(C#N)S2(=O)=O)cc1]

To a solution of the compound obtained in Step A (0.59 g) in dimethylformamide (40 ml) was added potassium carbonate (1.1 g). Then, a solution of 1,2-dibromoethane (0.59 g) in dimethylformamide (25 ml) was added dropwise at 55° C. The reaction mixture was then stirred at 55° C. for 2 hours, cooled to room temperature, poured into 15 ml water, and aqueous 2N hydrochloric acid was added to acidic pH. The aqueous layer was then extracted with dichloromethane, the combined organic layers washed two times with 2% aqueous hydrochloric acid, dried over sodium sulfate and concentrated in vacuo. Column chromatography (ethyl acetate/cyclohexane 7:3) afforded the title product as a beige solid (310 mg). $^1$HNMR (CDCl$_3$, 400 MHz): 7.30 (d, 2H), 6.90 (d, 2H), 4.25 (m, 1H), (m, 1H), 3.70-3.90 (m, 5H), 2.95 (m, 1H), 2.80 (m, 1H).

Step C: [2-(4-Methoxy-phenyl)-1,1-dioxo-1lambda*6*-isothiazolidin-5-ylmethyl]-carbamic acid tert-butyl ester

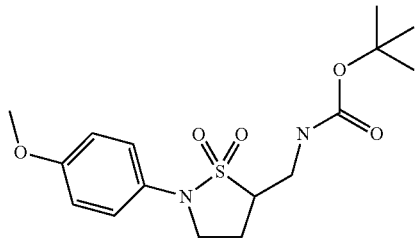 [SMILES: COc1ccc(N2CCC(CNC(=O)OC(C)(C)C)S2(=O)=O)cc1]

To a solution at 0° C. of the product obtained in Step B (500 mg) in methanol (15 ml) were added di-tert-butyldicarbonate (807 mg) and nickel (II) chloride hexahydrate (90 mg). Sodium borohydride (490 mg) was added portionwise. The reaction mixture was allowed to stir at room temperature for 24 hours. Diethylenetriamine (190 mg) was added, the reaction mixture was stirred for 30 min at room temperature then the solvent was removed in vacuo. The purple solid residue was diluted in ethyl acetate then washed with aqueous saturated hydrogen bicarbonate. The aqueous layer was extracted with ethyl acetate, the combined organic layers were dried over sodium sulfate and concentrated in vacuo. Purification using the Combi Flash200 afforded the title product as an impure brown oil (80 mg), which was used directly in the next step.

Step D: 4-[5-(3,5-Dichloro-phenyl)-5-trifluoromethyl-4,5-dihydro-isoxazol-3-yl]-N-[2-(4-methoxy-phenyl)-1,1-dioxo-1lambda*6*-isothiazolidin-5-ylmethyl]-2-methyl-benzamide

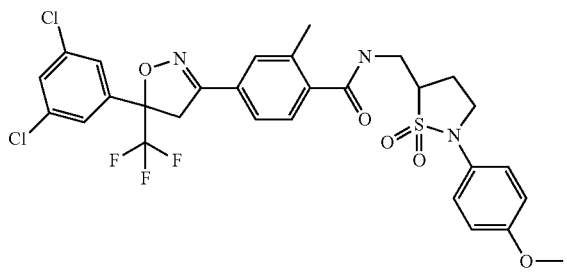 [SMILES: COc1ccc(N2CCC(CNC(=O)c3ccc(C4=NOC(c5cc(Cl)cc(Cl)c5)(C(F)(F)F)C4)cc3C)S2(=O)=O)cc1]

The compound obtained in Step C (94 mg) was deprotected and coupled with 4-[5-(3,5-dichloro-phenyl)-5-trifluoromethyl-4,5-dihydro-isoxazol-3-yl]-2-methyl-benzoic acid (0.125 g) (prepared according to WO 2009/080250) as described in Example 4, Steps B and C to afford the title compound as a brown solid (65 mg). LCMS (Method F) 2.02 min, M−H 654/655.

The following compounds were prepared following a similar method to that described in Example 14: 4-[5-(3,5-Dichloro-phenyl)-5-trifluoromethyl-4,5-dihydro-isoxazol-3-yl]-N-[2-(2,2,2-trifluoroethyl)-1,1-dioxo-1lambda*6*-isothiazolidin-5-ylmethyl]-2-methyl-benzamide (Compound F7).

EXAMPLE 15

Preparation of enantiomerically pure isomers of 4-[5-(3,5-dichloro-phenyl)-5-trifluoromethyl-4,5-dihydro-isoxazol-3-yl]-2-methyl-N-(2-ethyl-3-oxo-isoxazolidin-4-yl)-benzamide 4-[5-(3,5-Dichloro-phenyl)-5-trifluoromethyl-4,5-dihydro-isoxazol-3-yl]-2-methyl-benzoic acid (prepared as described in WO 2009/080250) was separated through chiral phase preparative HPLC (Column: CHIRALPAK® AD-H 5 μm; Mobile Phase: 80/20 Carbon Dioxide/Ethanol+1% Diethylamine; Flow Rate: 120 ml/min; Detection: 270 nm; Temperature: 25° C.; Outlet Pressure: 150 bars) to afford 4-[5-(3,5-dichloro-phenyl)-5-(S)-trifluoromethyl-4,5-dihydro-isoxazol-3-yl]-2-methyl-benzoic acid ($\alpha_D$+51.43°) and 4-[5-(3,5-dichloro-phenyl)-5-(R)-trifluoromethyl-4,5-dihydro-isoxazol-3-yl]-2-methyl-benzoic acid ($\alpha_D$−51.90°).

Amide coupling with (R)-4-Amino-2-ethyl-isoxazolidin-3-one and (S)-4-Amino-2-ethyl-isoxazolidin-3-one using the procedure described in Example 12, Step C afforded the 4 isomers of 4-[5-(3,5-dichloro-phenyl)-5-trifluoromethyl-4,5-dihydro-isoxazol-3-yl]-2-methyl-N-(2-ethyl-3-oxo-isoxazolidin-4-yl)-benzamide:

4-[5-(3,5-dichloro-phenyl)-5-(S)-trifluoromethyl-4,5-dihydro-isoxazol-3-yl]-2-methyl-N-((R)-2-ethyl-3-oxo-isoxazolidin-4-yl)-benzamide (Compound G1) Chiral HPLC (method H) RT 21.30 min, purity 97%.

4-[5-(3,5-dichloro-phenyl)-5-(R)-trifluoromethyl-4,5-dihydro-isoxazol-3-yl]-2-methyl-N-((R)-2-ethyl-3-oxo-isoxazolidin-4-yl)-benzamide (Compound G2): Chiral HPLC (method H) RT 19.79, purity 82%.

4-[5-(3,5-dichloro-phenyl)-5-(S)-trifluoromethyl-4,5-dihydro-isoxazol-3-yl]-2-methyl-N-((S)-2-ethyl-3-oxo-isoxazolidin-4-yl)-benzamide (Compound G3): Chiral HPLC (method H) RT 21.11, purity 91%.

4-[5-(3,5-dichloro-phenyl)-5-(R)-trifluoromethyl-4,5-dihydro-isoxazol-3-yl]-2-methyl-N-((S)-2-ethyl-3-oxo-isoxazolidin-4-yl)-benzamide (Compound G4): Chiral HPLC (method H) RT 17.07, purity 95%.

EXAMPLE 16

4-[(S)-5-(3,5-Dichloro-phenyl)-5-trifluoromethyl-4,5-dihydro-isoxazol-3-yl]-N-[(R)-2-(2,2-difluoro-ethyl)-3-oxo-isoxazolidin-4-yl]-2-methyl-benzamide (compound G6)

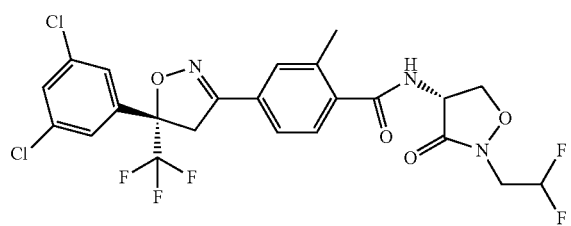 [SMILES: Cc1cc(C2=NO[C@@](c3cc(Cl)cc(Cl)c3)(C(F)(F)F)C2)ccc1C(=O)N[C@@H]1CON(CC(F)F)C1=O]

Step A: [(R)-2-(2,2-Difluoro-ethyl)-3-oxo-isoxazolidin-4-yl]-carbamic acid tert-butyl ester

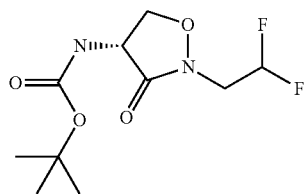 [SMILES: CC(C)(C)OC(=O)N[C@@H]1CON(CC(F)F)C1=O]

As described in Example 4, Step A, (3-oxo-isoxazolidin-4-yl)-carbamic acid tert-butyl ester (0.30 g) was alkylated with 2,2-difluoroethyl trifluoromethanesulfonate (0.35 g). to afford the title product as a white solid (138 mg); ¹H-NMR (CDCl₃, 400 MHz): 6.05 (tt, 1H), 5.10 (m, 1H), 4.90 (m, 1H), 4.35 (dt, 2H), 4.20 (dd, 1H), 1.50 (s, 9H); along with the O-alkylated product (179 mg): ¹H-NMR (CDCl₃, 400 MHz): 5.95 (tt, 1H), 4.80 (m, 1H), 4.60 (m, 1H), 3.80-4.10 (m, 3H), 1.50 (s, 9H).

Step B: (R)-4-Amino-2-(2,2-difluoroethyl)-isoxazolidin-3-one

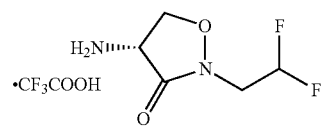 [SMILES: "·CF3COOH" ; N[C@@H]1CON(CC(F)F)C1=O]

The BOC protecting group was removed as described in Example 4, Step B to afford (R)-4-amino-2-(2,2-difluoroethyl)-isoxazolidin-3-one (trifluoroacetic acid salt), which was used directly in the next step.

Step C: 4-[5-(3,5-Dichloro-phenyl)-5-(S)-trifluoromethyl-4,5-dihydro-isoxazol-3-yl]-2-methyl-N-((R)-2-(2,2-difluoro ethyl)-3-oxo-isoxazolidin-4-yl)-benzamide

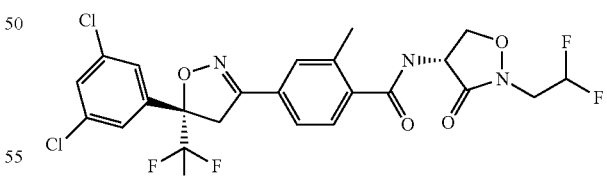

Amide coupling was performed using 4-[5-(3,5-dichloro-phenyl)-5-(S)-trifluoromethyl-4,5-dihydro-isoxazol-3-yl]-2-methyl-benzoic acid (0.27 g, prepared according to Example 15) as described in Example 12, step C. The title compound was obtained as a white solid (158 mg). M.p. 77-78° C.; LCMS (Method F) 2.09 min, M+H 564/566.

The following compound was prepared following a similar method to that described in Example 16: 4-[5-(3,5-Dichloro-phenyl)-5-(S)-trifluoromethyl-4,5-dihydro-isoxazol-3-yl]-2- methyl-N-((R)-2-(2,2-difluoroethyl)-3-oxo-isoxazolidin-4-yl)-benzamide (compound G5).

EXAMPLE 17

6-[5-(3,5-Dichloro-phenyl)-5-trifluoromethyl-4,5-dihydro-isoxazol-3-yl]-4-methyl-N-[(R)-3-oxo-2-(2,2-trifluoro-ethyl)-isoxazolidin-4-yl]-nicotinamide (compound C6)

Step A: 5-Bromo-2-iodo-4-methyl-pyridine

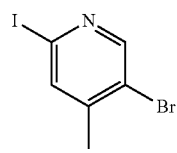

To a solution of 2,5-dibromo-4-methylpyridine (2 g) in acetonitrile (40 ml) at room temperature under argon were added sodium iodide (4.8 g) then acetyl chloride (0.94 g). After 3 hours stirring at room temperature the white solid formed was filtered off and the filtrate was neutralized with aqueous saturated solution of sodium hydrogenocarbonate. The organic phase was dried over sodium sulfate and concentrated in vacuo. The residue was purified by column chromatography (ethyl acetate/cyclohexane) to afford the title product as a brown solid (2.04 g). $^1$H-NMR (CDCl$_3$, 400 MHz): 8.40 (s, 1H), 7.60 (s, 1H), 2.30 (s, 3H), Step B: 5-Bromo-4-methyl-pyridine-2-carbaldehyde

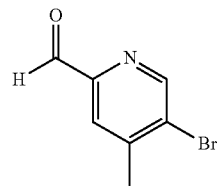

In an oven-dried flask the compound obtained in Step A (4.67 g) was dissolved in tetrahydrofuran (22 ml). The solution was cooled to −15° C., then isopropyl magnesium bromide (17.2 ml, 15% solution in THF) was added dropwise at a rate to keep the internal temperature between −15° C. to −10° C. The reaction was stirred at this temperature for 1 hour, then anhydrous dimethylformamide (1.8 ml) was added at a rate to keep the internal temperature below 0° C. The reaction was stirred at this temperature for 1 hour, then poured into water and extracted with diethyl ether. The organic layer was dried over sodium sulfate and concentrated in vacuo. The crude title aldehyde product (2.4 g, brown solid) was used as such in the next step.

Step C: 5-Bromo-4-methyl-pyridine-2-carbaldehyde oxime

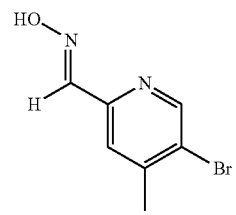

To a solution of the compound obtained in Step B (3.1 g) in EtOH (47.5 ml) and water (23 ml) were added hydroxylamine hydrochloride (1.4 g) and sodium acetate (1.9 g). The reaction was stirred for 15 min at room temperature. The white solid was filtered off and the solution concentrated in vacuo to afford the crude title product (2.2 g, white solid), which was used directly for the next step. LCMS (Method F) 2.09 min, M+H 564/566.

Step D: 5-Bromo-2-[5-(3,5-dichloro-phenyl)-5-trifluoromethyl-4,5-dihydro-isoxazol-3-yl]-4-methyl-pyridine

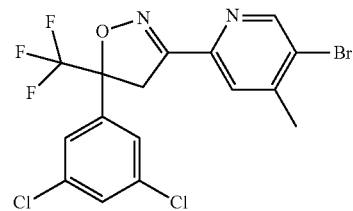 [SMILES: Cc1cc(C2=NOC(c3cc(Cl)cc(Cl)c3)(C(F)(F)F)C2)ncc1Br]

To a solution of the compound obtained in Step C (2.2 g) in dimethylformamide (24 ml) was added N-chlorosuccinimide (1.4 g) in three portions at room temperature under argon. The reaction mixture was allowed to stir overnight at room temperature then a solution of 1,3-dichloro-5-(1-trifluoromethyl-vinyl)-benzene (2.7 g, prepared as described in WO 2009/080250) in DMF (6 ml) was added followed by triethylamine (1.43 ml) in DMF (14 ml). The reaction stirred at room temperature for 1 hour then poured into ice water. A white solid precipitated, which was filtered, washed with water and dried under vacuum to give the title product (4.1 g). $^1$H-NMR (CDCl₃, 400 MHz): 8.60 (s, 1H), 7.90 (s, 1H), 7.50 (s, 2H), 7.40 (s, 1H), 4.20 (d, 1H), 3.85 (d, 1H), 2.45 (s, 3H), Step E: 6-[5-(3,5-Dichloro-phenyl)-5-trifluoromethyl-4,5-dihydro-isoxazol-3-yl]-4-methyl-nicotinic acid

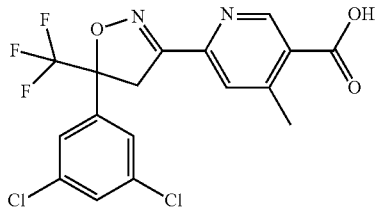 [SMILES: Cc1cc(C2=NOC(c3cc(Cl)cc(Cl)c3)(C(F)(F)F)C2)ncc1C(=O)O]

In a 300 ml flask were charged n-butanol (90 ml), palladium acetate (38 mg) and n-butyl-diadamantylphosphine (184 mg). Then, tetramethylendiamine (1.93 ml) and 5-bromo-2-[5-(3,5-dichloro-phenyl)-5-trifluoromethyl-4,5-dihydro-isoxazol-3-yl]-4-methyl-pyridine (7.5 g, obtained as described in Step D) were added.

The reaction was performed under carbon monoxide at 15 bar at room temperature for 20 min. The reaction mixture was then diluted in toluene and the suspension was filtered on Celite and washed with toluene. The solvent was removed under reduced pressure to obtain a red oil. The residue was purified by column chromatography (ethyl acetate, cyclohexane) to yield the butyl ester of the title product as a liquid (3.45 g). ¹H-NMR (CDCl₃, 400 MHz): 9.03 (s, 1H), 7.90 (s, 1H), 7.50 (s, 2H), 7.40 (s, 1H), 4.35 (t, 2H), 4.25 (d, 1H), 3.90 (d, 1H), 2.55 (s, 3H), 1.80 (q, 2H9, 1.50 (q, 2H), 1.00 (t, 3H). This ester was dissolved in tetrahydrofuran (8 ml), and sodium hydroxide (0.58 g) in methanol (8 ml) and water (16 ml) was added dropwise. The reaction mixture was stirred at room temperature for 3 hours, diluted with ethyl acetate and acidified with 1N hydrochloric acid. The aqueous layer was extracted with ethyl acetate and the combined organic layers were dried over sodium sulfate then concentrated in vacuo. The residue was triturated in heptane and filtered to obtain the title product as a beige solid (2 g). LCMS (Method F) 2.22 min, M+H 419/421.

Step F: 6-[5-(3,5-Dichloro-phenyl)-5-trifluoromethyl-4,5-dihydro-isoxazol-3-yl]-4-methyl-N-[(R)-3-oxo-2-(2,2,2-trifluoro-ethyl)-isoxazolidin-4-yl]-nicotinamide

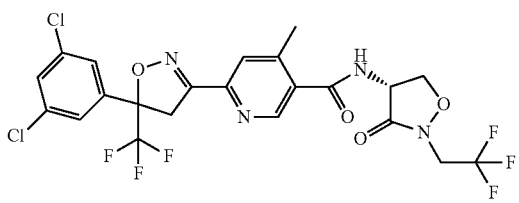 [SMILES: Cc1cc(C2=NOC(c3cc(Cl)cc(Cl)c3)(C(F)(F)F)C2)ncc1C(=O)N[C@@H]1CON(CC(F)(F)F)C1=O]

The title compound was obtained by coupling the carboxylic acid obtained in Step E (0.15 g) with (R)-4-Amino-2-(2,2,2-trifluoro-ethyl)-isoxazolidin-3-one (0.10 g, obtained as described in Example 3 for the preparation of compound B5) as described in Example 12, Step C. The title product was obtained as a white solid (48 mg). M.p. 53-55° C. LCMS (Method F) 2.13 min, M+H 583/585.

The following compound was prepared following a similar method to that described in Example 17: 6-[5-(3,5-Dichloro-phenyl)-5-trifluoromethyl-4,5-dihydro-isoxazol-3-yl]-4-methyl-N-[(R)-3-oxo-2-(2,2,2-trifluoro-ethyl)-isoxazolidin-4-yl]-nicotinamide (compound C7).

Similarly, when this reaction was carried out to obtain 2-methyl-N-[(R)-3-oxo-2-(2,2,2-trifluoro-ethyl)-isoxazolidin-4-yl]-4-[5-(3,4,5-trichloro-phenyl)-5-trifluoromethyl-4,5-dihydro-isoxazol-3-yl]-benzamide (compound C8), it was possible to separate the two diastereoisomers by precipitation after the purification by column chromatography. The product obtained after column chromatography was thus stirred with diethyl ether and a solid precipitated out of the solution. The solid (enriched in one diastereomer) was analysed by chiral HPLC (method K): 8.90 min (91.02%), 11.97 min (08.98%). The filtrate (enriched in the other diastereomer) was also analysed by chiral HPLC (method K): 8.66 min (17.50%), 11.02 min (69.38%).

Similarly, when this reaction was carried out to obtain 4-[5-(3,5-dichloro-4-fluoro-phenyl)-5-trifluoromethyl-4,5-dihydro-isoxazol-3-yl]-2-methyl-N-[(R)-3-oxo-2-(2,2,2-trifluoro-ethyl)-isoxazolidin-4-yl]-benzamide (compound C9), it was possible to separate the two diastereoisomers by precipitation after the purification by column chromatography. The residue was stirred with diethyl ether and a solid precipitated out of the solution. The solid (enriched in one diastereomer) was analysed by chiral HPLC (method K): 8.31 min (87.79%). The filtrate (enriched in the other diastereomer) was also analysed by chiral HPLC (method K): 8.28 min (18.15%), 10.75 min (81.85%).

EXAMPLE 18

General Method for Preparing the Compounds of the Invention in Parallel

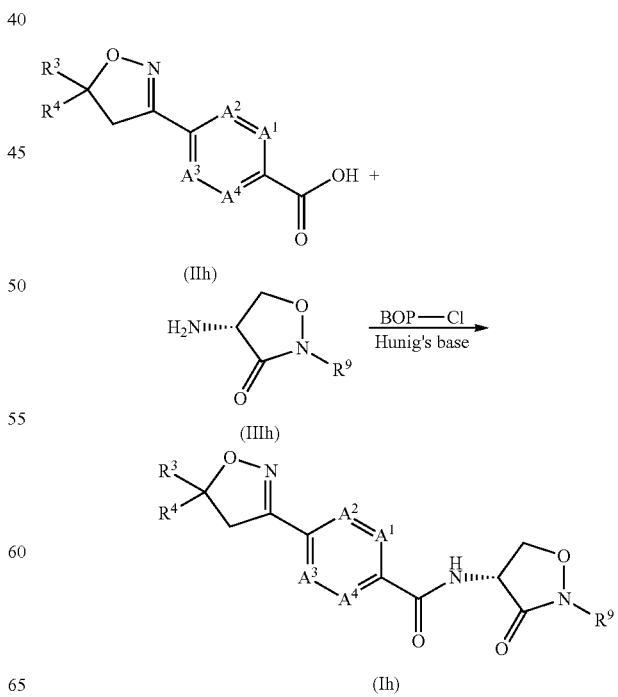

To a solution of a benzoic acid of the formula (IIh) (20 μmol) in N,N-dimethylacetamide ("DMA") (0.4 ml) was added successively a solution of an amine of the formula (IIIh) (26 μmol) in N,N-dimethylacetamide ("DMA") (0.4 ml), diisopropylethylamine (Hunig's Base) (0.03 ml), and a solution of bis(2-oxo-3-oxazolidinyl)phosphonic chloride ("BOP-Cl") (10.2 mg) in N,N-dimethylacetamide ("DMA") (0.2 ml). The reaction mixture was stirred at 90° C. for 16 hours. The reaction mixture was concentrated and the crude mixture was redissolved in acetonitrile/N,N-dimethylacetamide (4:1) (0.8 ml) and purified by HPLC. This method was used to prepare a number of compounds (Compound Nos. H1 to H26 of Table H) in parallel. The starting carboxylic acids used for the preparation of compounds of Table H were obtained as described in Examples 19 to 31.

EXAMPLE 19

2-Methyl-4-[5-(3-trifluoromethoxy-phenyl)-5-trifluoromethyl-4,5-dihydro-isoxazol-3-yl]-benzoic acid

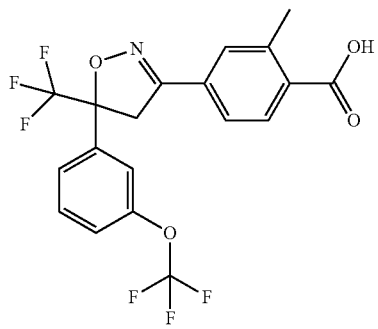 [SMILES: Cc1cc(C2=NOC(c3cccc(OC(F)(F)F)c3)(C(F)(F)F)C2)ccc1C(=O)O]

This compound was prepared following a similar route to that described in Example 24.

EXAMPLE 20

6-[5-(3,5-Dichloro-phenyl)-5-trifluoromethyl-4,5-dihydro-isoxazol-3-yl]-2-methyl-nicotinic acid

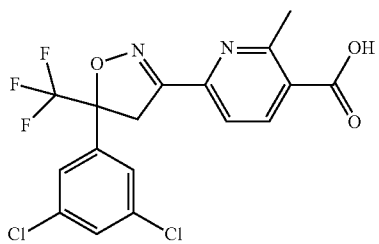 [SMILES: Cc1nc(C2=NOC(c3cc(Cl)cc(Cl)c3)(C(F)(F)F)C2)ccc1C(=O)O]

This compound was prepared from 2,5-dibromo-6-methyl-pyridine following a similar route to that described in Example 17, Steps A-E.

EXAMPLE 21

8-[5-(3,5-Dichloro-phenyl)-5-trifluoromethyl-4,5-dihydro-isoxazol-3-yl]-quinoline-5-carboxylic acid

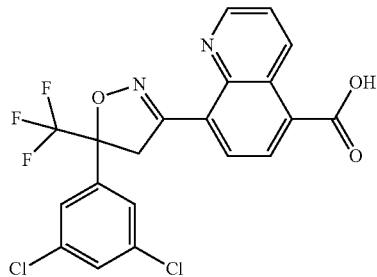 [SMILES: O=C(O)c1ccc(C2=NOC(c3cc(Cl)cc(Cl)c3)(C(F)(F)F)C2)c2ncccc12]

The title product was prepared from 5-bromo-quinoline-8-carbaldehyde using the same synthetic route described in Example 17, Steps C-E.

5-Bromo-quinoline-8-carbaldehyde was prepared as follows:

Step A: 5-Bromo-8-methyl-quinoline

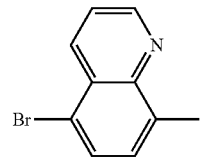

A solution of 5-Bromo-2-methylaniline (7.44 g), glycerol (7.4 g), nitrobenzene (4.9 g) in 75% sulfuric acid (20 ml) was heated at 150° C. for 3 hrs. The solution was cooled to 0° C. then carefully neutralized with aqueous sodium hydroxide. The reaction mixture became a dark gum and was diluted with water and extracted three times with ethyl acetate. The combined organic layers were washed with saturated brine, then dried with sodium sulphate and the solvent removed in vacuo. The crude product was purified by column chromatography (dichloromethane) to afford the title compound as a solid (6 g). $^1$H-NMR (CDCl$_3$, 400 MHz) 8.91 (m, 1H), 8.51 (m, 1H), 7.7 (m, 1H), 7.50 (m, 1H), 7.4 (m, 1H), 2.72 (s, 3H).

Step B: 5-Bromo-8-dibromomethyl-quinoline

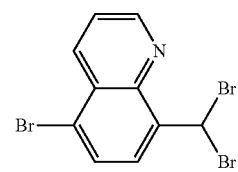 [SMILES: Brc1ccc(C(Br)Br)c2ncccc12]

Radical dibromination was performed using standard method from the compound obtained in Step A (4.4 g), N-bromo-succinimide (8.9 g) in tetrachloromethane (200 ml) at reflux for 12 hours in the presence of dibenzoyl peroxide (245 mg). At the end of the reaction, the succinimide was filtered off, the solvent was removed in vacuo, and the crude product used as such for the next step. $^1$H-NMR (CDCl$_3$, 400 MHz) 8.90 (m, 1H), 8.45 (dd, 1H), 8.15 (d, 1H), 8.10 (s, 1H), 7.80 (d, 1H), 7.45 (m, 1H).

Step C: 5-Bromo-quinoline-8-carbaldehyde

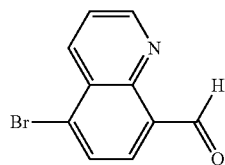 [SMILES: O=Cc1ccc(Br)c2cccnc12]

Hydrolysis of the dibromo compound obtained using the method described in Step B (9 g) was carried out in acetone (138 ml) and water (23 ml) in the presence of silver nitrate (9.7 g) in the dark at room temperature for 5 hours. The silver salts were filtered off through a pad of Celite. The filtrate was diluted with ethyl acetate (150 ml), transferred to a separatory funnel, then washed successively with saturated aqueous sodium bicarbonate (100 ml), water (3×50 ml), and brine (50 ml). The organic layer was dried over sodium sulphate filtered, and evaporated under reduced pressure to afford the title product (4.70 g) as a yellow solid. $^1$H-NMR (CDCl$_3$, 400 MHz) 11.4 (s, 1H, CHO) 9.05 (m, 1H), 8.61 (dd, 1H), 8.15 (d, 1H), 8.0 (d, 1H), 7.60 (m, 1H)

EXAMPLE 22

4-[5-(3,5-Dichloro-phenyl)-5-trifluoromethyl-4,5-dihydro-isoxazol-3-yl]-pyridine-2-carboxylic acid

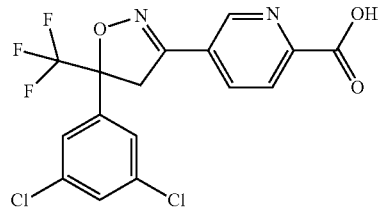 [SMILES: O=C(O)c1ccc(C2=NOC(c3cc(Cl)cc(Cl)c3)(C(F)(F)F)C2)cn1]

This compound was prepared from 5-formyl-pyridine-2-carboxylic acid methyl ester using the standard synthesis described in WO 2009/080250. 5-Formyl-pyridine-2-carboxylic acid methyl ester was synthesized by reductive formylation of 5-bromo-pyridine-2-carboxylic acid methyl ester using the conditions described in Angewandte Chemie, International Edition (2006), 45(1), 154-158.

EXAMPLE 23

2-Cyclopropyl-4-[5-(3,5-dichloro-phenyl)-5-trifluoromethyl-4,5-dihydro-isoxazol-3-yl]-benzoic acid

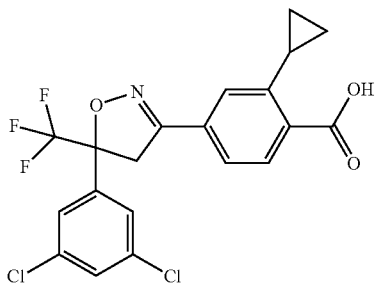 [SMILES: O=C(O)c1ccc(C2=NOC(c3cc(Cl)cc(Cl)c3)(C(F)(F)F)C2)cc1C1CC1]

This acid was prepared from the methyl ester of 2-bromo-4-[5-(3,5-dichloro-phenyl)-5-trifluoromethyl-4,5-dihydro-isoxazol-3-yl]-benzoic acid (Example 27) as follows:

A solution of cyclopropyl boronic acid (0.67 g), 2-bromo-4-[5-(3,5-dichloro-phenyl)-5-trifluoromethyl-4,5-dihydro-isoxazol-3-yl]-benzoic acid methyl ester (3 g) and Bis(triphenylphosphine)palladium(II) chloride (210 mg) were sequentially added to degassed toluene (38 ml). The reaction mixture was stirred for 30 min at room temperature then a degassed aqueous 2N solution of potassium phosphate (7 ml) was added and the resulting mixture was heated at 110° C. overnight. The reaction mixture was filtered over Hyflo and the resulting solution was concentrated in vacuo to give a yellow oil, which was poured into ethyl acetate. The organic phase was washed with water, dried over sodium sulfate, and the solvents were evaporated in vacuo. The product was used as such for the saponification step, as described in Example 17, Step E to afford the title acid compound (2.5 g) as a yellow solid. LCMS (Method F) 2.15 min M−H 442/444.

EXAMPLE 24

2-Methyl-4-[5-(4-cyano-3,5-dichloro-phenyl)-5-trifluoromethyl-4,5-dihydro-isoxazol-3-yl]-benzoic acid

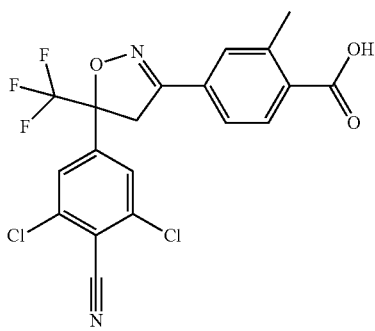 [SMILES: Cc1cc(C2=NOC(c3cc(Cl)c(C#N)c(Cl)c3)(C(F)(F)F)C2)ccc1C(=O)O]

Steps A-C: Preparation of 2,6-Dichloro-4-(1-trifluoromethyl-vinyl)-benzonitrile

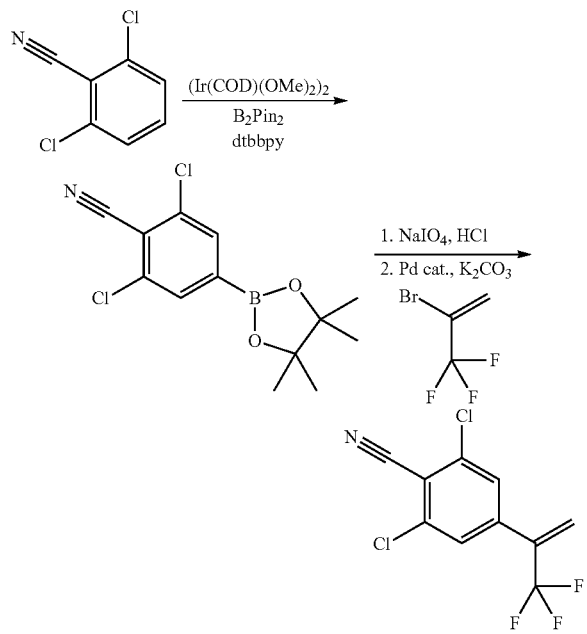

Step A

To a solution of Bis(1,5-cyclooctadiene)dimethoxydiiridium (35 mg) in hexane (10 ml) under argon was added 4,4'-Di-tert-butyl-2,2'-bipyridine (110 mg). To this dark brown suspension was added pinacol diborane (2.23 g) and the solution was stirred at room temperature for 5 min. To this solution was added 2,6-Dichloro-benzonitrile (1 g) and the mixture was heated at 50° C. for 22 hours. The solution was then filtered on a Celite pad and the filtrate was concentrated. The residue was then dissolved with ethyl acetate and extracted with saturated ammonium chloride. The organic layer was washed with water, dried over sodium sulfate and concentrated. The residue was used as such in the next reaction.

Step B

To a solution of crude 2,6-dichloro-4-(4,4,5,5-tetramethyl-[1,3,2]dioxaborolan-2-yl)-benzonitrile (2.32 g) in a 4:1 mixture THF/H$_2$O (63 ml) was added sodium periodate (5.01 g). The solution was stirred for 30 min. At room temperature aqueous hydrochloric acid (1N, 5.5 ml) was added to the suspension. The solution was further stirred at room temperature for 6 hours then water and diethyl ether were added and the phases were separated. The organic layer was washed with water, dried over sodium sulfate and concentrated. The residue was used as such in the next reaction.

Step C

To a solution of crude 2,6-dichloro-4-(boronic acid)-benzonitrile (1.2 g) in a 2:1 mixture THF/H$_2$O (27 ml) was added 2-Bromo-3,3,3-trifluoro-propene (1.2 ml), potassium carbonate (1.54 g), and then 1,3-bis(2,6-diisopropylphenyl)-imidazol-2-ylidene(1,4-naphthoquinone)palladium (438 mg). The reaction mixture was stirred at 60° C. for 3 hours. The solution was allowed to cool to room temperature and then filtered on a Celite pad. The filtrate was concentrated undervacuo and the residue was then dissolved with diethyl ether, extracted with water, dried over magnesium sulfate and concentrated. The residue was purified by chromatography on silica gel to give 2,6-Dichloro-4-(1-trifluoromethyl-vinyl)-benzonitrile (1.37 g). $^{19}$F-NMR (CDCl$_3$, 75 MHz): −64.65 ppm.

Similarly, 1-Chloro-3-trifluoromethyl-5-(1-trifluoromethyl-vinyl)-benzene was obtained. $^{19}$F-NMR (CDCl$_3$, 75 MHz): −63.00 and −65.04 ppm.

Similarly, 1-Bromo-3-chloro-5-(1-trifluoromethyl-vinyl)-benzene was obtained. $^{19}$F-NMR (CDCl$_3$, 75 MHz): −64.95 ppm.

Step D: Preparation of 1-Trifluoromethoxy-3-(1-trifluoromethyl-vinyl)-benzene

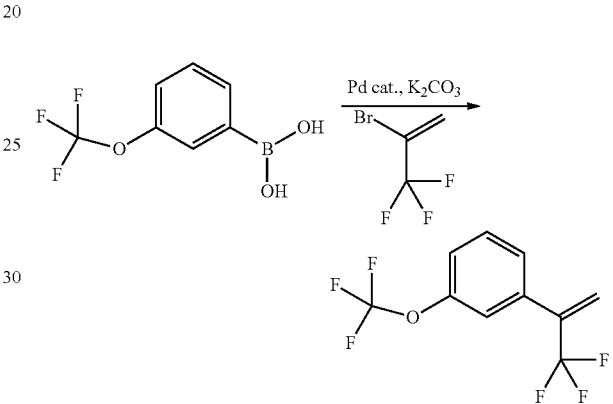

To a solution of 3-Trifluoromethoxy-benzeneboronic acid (2.5 g) in a 2:1 mixture THF/H$_2$O (36 ml) was added 2-Bromo-3,3,3-trifluoro-propene (3.1 ml), potassium carbonate (3.35 g), then Bis(triphenylphosphine)palladium(II) dichloride (169 mg). The reaction mixture was stirred at 60° C. for 7 hours. The solution was allowed to cool to room temperature then filtered on a Celite pad. The filtrate was concentrated in vacuo and the residue was then dissolved with ethyl acetate, extracted with water, dried over magnesium sulfate and concentrated. The residue was purified by chromatography on silica gel to give 1-Trifluoromethoxy-3-(1-trifluoromethyl-vinyl)-benzene (1.23 g). $^{19}$F-NMR (CDCl$_3$, 75 MHz): −57.87 ppm and −64.94 ppm.

Step E: Preparation of 4-[5-(3,5-Dichloro-4-cyanophenyl)-5-trifluoromethyl-4,5-dihydro-isoxazol-3-yl]-2-methyl-benzoic acid tert-butyl ester

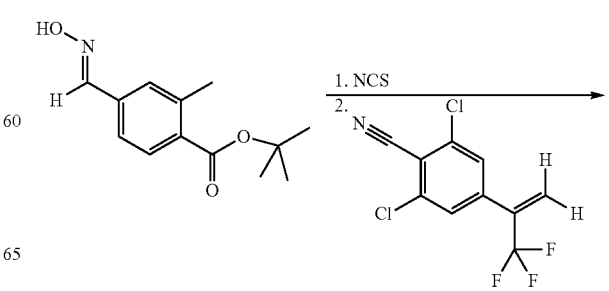

-continued

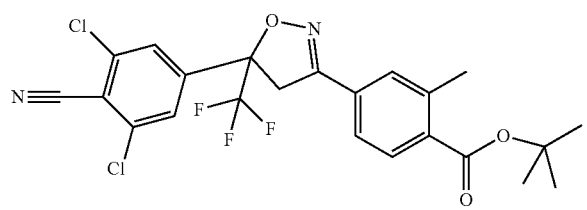

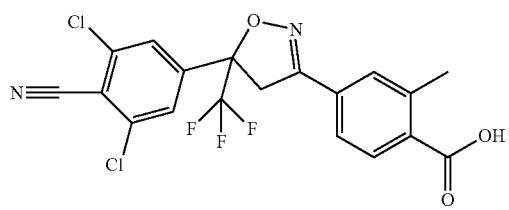

To a solution of 4-(hydroxyimino-methyl)-2-methyl-benzoic acid tert-butyl ester (1.47 g) in N,N-dimethylformamide (13 ml) was added N-chlorosuccinimide ("NCS") (832 mg). The reaction mixture was stirred at ambient temperature for 2 hours. More N-chlorosuccinimide ("NCS") (850 mg) was added and the reaction mixture was stirred at ambient temperature for 1 hour. A solution of 2,6-Dichloro-4-(1-trifluoromethyl-vinyl)-benzonitrile (1.37 g) and triethylamine (0.72 ml) in N,N-dimethylformamide (13 ml) was added dropwise to the reaction mixture. The reaction mixture was stirred at ambient temperature for 17 hours. Water and ethyl acetate were added and the phases were separated. The organic layer was washed with water, dried over sodium sulfate and concentrated. The residue was purified by chromatography on silica gel to give 4-[5-(3,5-Dichloro-4-cyano-phenyl)-5-trifluoromethyl-4,5-dihydro-isoxazol-3-yl]-2-methyl-benzoic acid tert-butyl ester (0.902 g). $^{19}$F-NMR (CDCl$_3$, 75 MHz): −78.93 ppm.

Similarly, 4-[5-(3-Bromo-5-chloro-phenyl)-5-trifluoromethyl-4,5-dihydro-isoxazol-3-yl]-2-methyl-benzoic acid tert-butyl ester was obtained when 1-Bromo-3-chloro-5-(1-trifluoromethyl-vinyl)-benzene was used as reagent. $^{19}$F-NMR (CDCl$_3$, 75 MHz): −79.49 ppm.

Similarly, 4-[5-(3-Chloro-5-trifluoromethyl-phenyl)-5-trifluoromethyl-4,5-dihydro-isoxazol-3-yl]-2-methyl-benzoic acid tert-butyl ester was obtained when 1-Chloro-3-trifluoromethyl-5-(1-trifluoromethyl-vinyl)-benzene was used as reagent. $^{19}$F-NMR (CDCl$_3$, 75 MHz): −62.83 and −79.59 ppm.

Similarly, 2-Methyl-4-[5-trifluoromethyl-5-(3-trifluoromethoxy-phenyl)-4,5-dihydro-isoxazol-3-yl]-benzoic acid tert-butyl ester was obtained when 1-Trifluoromethoxy-3-(1-trifluoromethyl-vinyl)-benzene was used as reagent. $^{19}$F-NMR (CDCl$_3$, 75 MHz): −57.87 ppm and −79.85 ppm.

Step F: Preparation of 4-[5-(3,5-dichloro-4-cyanophenyl)-5-trifluoromethyl-4,5-dihydro-isoxazol-3-yl]-2-methyl-benzoic acid

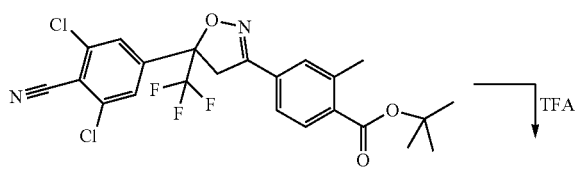

To a solution of 4-[5-(3,5-Dichloro-4-cyano-phenyl)-5-trifluoromethyl-4,5-dihydro-isoxazol-3-yl]-2-methyl-benzoic acid tert-butyl ester (763 mg) in dichloromethane (9 ml) was added trifluoromethyl acetic acid ("TFA") (0.9 ml). The reaction mixture was stirred at ambient temperature for 20 hours. Ethyl acetate was added and the mixture was washed with water, dried over sodium sulfate and concentrated to give 4-[5-(3,5-Dichloro-4-cyano-phenyl)-5-trifluoromethyl-4,5-dihydro-isoxazol-3-yl]-2-methyl-benzoic acid. $^{19}$F-NMR (CDCl$_3$, 75 MHz): −78.91 ppm.

Similarly, 4-[5-(3-Bromo-5-chloro-phenyl)-5-trifluoromethyl-4,5-dihydro-isoxazol-3-yl]-2-methyl-benzoic acid was obtained when 4-[5-(3-Bromo-5-chloro-phenyl)-5-trifluoromethyl-4,5-dihydro-isoxazol-3-yl]-2-methyl-benzoic acid tert-butyl ester was used as starting material. $^{19}$F-NMR (CDCl$_3$, 75 MHz): −79.46 ppm.

Similarly, 4-[5-(3-Chloro-5-trifluoromethyl-phenyl)-5-trifluoromethyl-4,5-dihydro-isoxazol-3-yl]-2-methyl-benzoic acid was obtained when 4-[5-(3-Chloro-5-trifluoromethyl-phenyl)-5-trifluoromethyl-4,5-dihydro-isoxazol-3-yl]-2-methyl-benzoic acid tert-butyl ester was used as starting material. $^{19}$F-NMR (CDCl$_3$, 75 MHz): −62.84 and −79.56 ppm.

Similarly, 2-Methyl-4-[5-trifluoromethyl-5-(3-trifluoromethoxy-phenyl)-4,5-dihydro-isoxazol-3-yl]-benzoic acid was obtained when 2-Methyl-4-[5-trifluoromethyl-5-(3-trifluoromethoxy-phenyl)-4,5-dihydro-isoxazol-3-yl]-benzoic acid tert-butyl ester was used as starting material. $^{19}$F-NMR (CDCl$_3$, 75 MHz): −57.87 ppm and −79.83 ppm.

EXAMPLE 25

1-[5-(3,5-Dichloro-phenyl)-5-trifluoromethyl-4,5-dihydro-isoxazol-3-yl]-isoquinoline-4-carboxylic acid

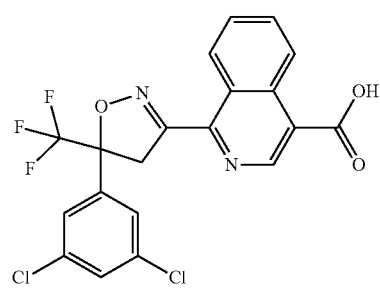 [SMILES: O=C(O)c1cnc(C2=NOC(c3cc(Cl)cc(Cl)c3)(C(F)(F)F)C2)c2ccccc12]

The title product was prepared from 4-bromo-1-methyl-isoquinoline following a similar route to that described in described in Example 21.

EXAMPLE 26

4-[5-(3,5-Dichloro-phenyl)-5-trifluoromethyl-4,5-dihydro-isoxazol-3-yl]-benzoic acid

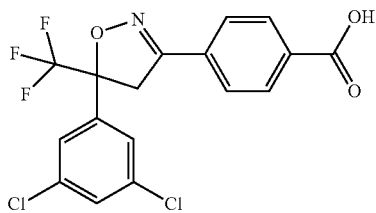

This compound was prepared as described in WO 2005/085216.

EXAMPLE 27

2-Bromo-4-[5-(3,5-dichloro-phenyl)-5-trifluoromethyl-4,5-dihydro-isoxazol-3-yl]-benzoic acid

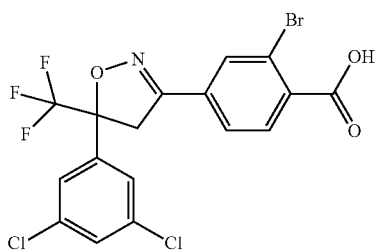 [SMILES: O=C(O)c1ccc(C2=NOC(c3cc(Cl)cc(Cl)c3)(C(F)(F)F)C2)cc1Br]

This compound was prepared as described in WO 2009/080250.

EXAMPLE 28

4-[5-(3,5-Dichloro-phenyl)-5-trifluoromethyl-4,5-dihydro-isoxazol-3-yl]-naphthalene-1-carboxylic acid

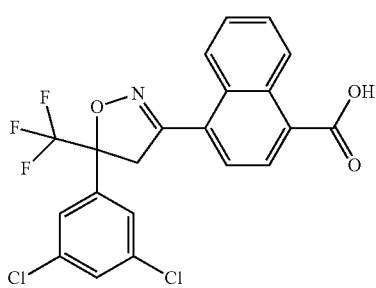 [SMILES: O=C(O)c1ccc(C2=NOC(c3cc(Cl)cc(Cl)c3)(C(F)(F)F)C2)c2ccccc12]

This compound was prepared as described in WO 2010/025998.

EXAMPLE 29

2-Methyl-4-[5-(3-chloro-5-trifluoromethyl-phenyl)-5-trifluoromethyl-4,5-dihydro-isoxazol-3-yl]-benzoic acid

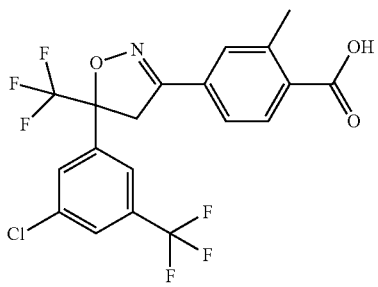 [SMILES: Cc1cc(C2=NOC(c3cc(Cl)cc(C(F)(F)F)c3)(C(F)(F)F)C2)ccc1C(=O)O]

This compound was prepared following a similar route to that described in Example 24.

EXAMPLE 30

2-Methyl-4-[5-(3-chloro-5-bromo-phenyl)-5-trifluoromethyl-4,5-dihydro-isoxazol-3-yl]-benzoic acid

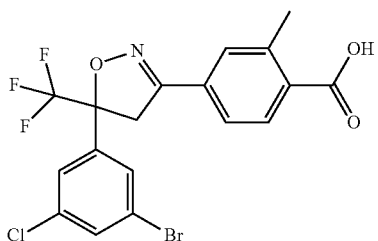 [SMILES: Cc1cc(C2=NOC(c3cc(Cl)cc(Br)c3)(C(F)(F)F)C2)ccc1C(=O)O]

This compound was prepared following a similar route to that described in Example 24.

EXAMPLE 31

2-Methyl-4-[5-(3,5-dichloro-phenyl)-5-chlorodifluoromethyl-4,5-dihydro-isoxazol-3-yl]-benzoic acid

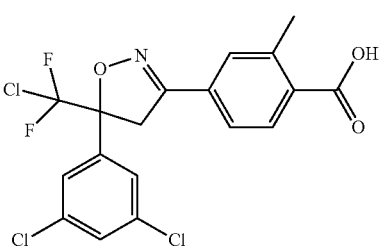 [SMILES: Cc1cc(C2=NOC(c3cc(Cl)cc(Cl)c3)(C(F)(F)Cl)C2)ccc1C(=O)O]

Step A: Preparation of 4-[5-(Chloro-difluoro-methyl)-5-(3,5-dichloro-phenyl)-4,5-dihydro-isoxazol-3-yl]-2-methyl-benzoic acid tert-butyl ester

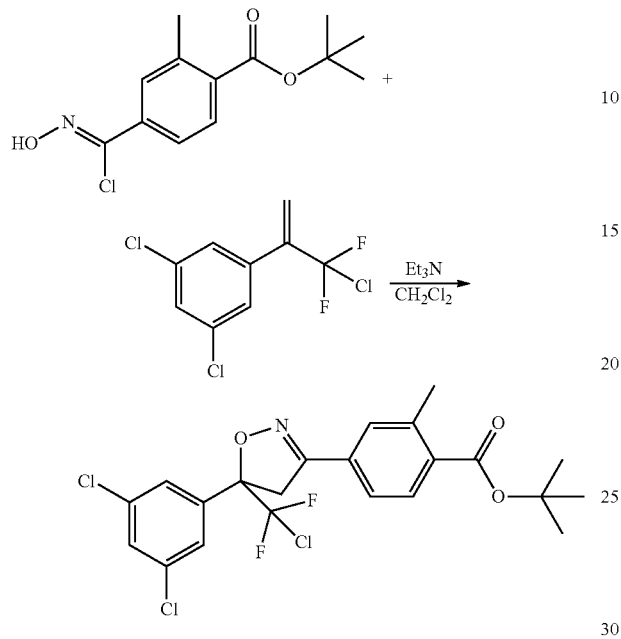

To a solution of benzoic acid 4-[chloro(hydroxyimino)methyl]-2-(trifluoromethyl) tert-butyl ester (prepared according to WO 2009/080250) (1.25 g) and 1,3-dichloro-5-[1-(chloro-difluoro-methyl)-vinyl]-benzene (1.19 g) (prepared according to WO 2005/085216) in dichloromethane (30 ml) triethylamine (1.9 ml) was added. The reaction mixture was filtered over a plug of silica and concentrated to give (1.95 g) 4-[5-(Chloro-difluoro-methyl)-5-(3,5-dichloro-phenyl)-4,5-dihydro-isoxazol-3-yl]-2-methyl-benzoic acid tert-butyl ester (1.69 g) which was used in the following step without any further purification.

Step B: 4-[5-(Chloro-difluoro-methyl)-5-(3,5-dichloro-phenyl)-4,5-dihydro-isoxazol-3-yl]-2-methyl-benzoic acid

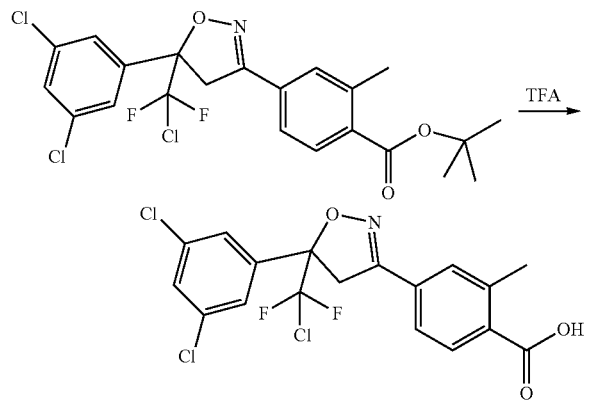

To a solution of 4-[5-(chloro-difluoro-methyl)-5-(3,5-dichloro-phenyl)-4,5-dihydro-isoxazol-3-yl]-2-methyl-benzoic acid tert-butyl ester (1.95 g) in dichloromethane (20 ml) was added trifluoromethyl acetic acid ("TFA") (3 ml). The reaction mixture was stirred at ambient temperature for 16 hours. The dichloromethane was removed by distillation. The residue was purified over silica gel (eluent: ethyl acetate/heptane gradient from 1:1 to 1:0) to give 4-[5-(Chloro-difluoro-methyl)-5-(3,5-dichloro-phenyl)-4,5-dihydro-isoxazol-3-yl]-2-methyl-benzoic acid (1.37 g). $^1$H-NMR (CDCl$_3$, 400 MHz): 8.10 (d, 1H), 7.65-7.45 (m, 5H), 4.15 (m, 1H), 3.75 (d, 1H), 2.70 (s, 3H).

EXAMPLE 32

Preparation of (5{4-[5-(3,5-dichloro-phenyl)-5-trifluoromethyl-4,5-dihydro-isoxazol-3-yl]-2-methyl-benzoylamino}-methyl-2-oxo-[1,2,3]oxathiazolidine-3-carboxylic acid carbamic acid ter-butyl ester (Compound F8)

Step A: Preparation of (3 {4-[5-(3,5-dichloro-phenyl)-5-trifluoromethyl-4,5-dihydro-isoxazol-3-yl]-2-methyl-benzoylamino}-2-hydroxy-propyl)-carbamic acid tert-butyl ester

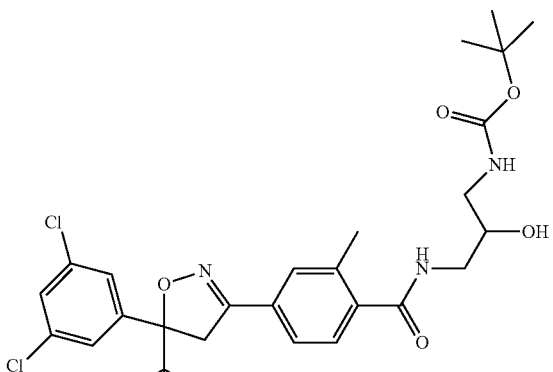

Oxalyl chloride (0.9 ml) was added dropwise to a solution of 4-[5-(3,5-dichloro-phenyl)-5-methyl-4,5-dihydro-isoxazol-3-yl]-2-methylbenzoic acid (0.9 g) in dichloromethane (20 ml) and 1 drop of N,N-dimethylformamide and stirred at room temperature under nitrogen for 6 hours. The mixture was concentrated and the residue was dissolved in acetonitrile (50 ml), treated with a solution of (3-amino-2-hydroxy-propyl)-carbamic acid ter-butyl ester (0.8 g) (*J. Med. Chem.* 1998, 41, 236-246), and a solution of triethylamine (0.9 ml) in acetonitrile (50 ml) and stirred for 16 hours under nitrogen atmosphere. The reaction mixture was concentrated and purified by chromatography on silica gel (eluent hexane/ethyl acetate 50:50) to give the title compound (0.51 g). LCMS (Method G) 4.00 min, MH$^+$ 590. $^1$HNMR (CDCl$_3$, 400 MHz): 7.42-7.51 (m, 6H), 6.77 (m, 1H), 5.11 (t, 1H), 4.09 (d, 1H), 3.86 (m, 1H), 3.80 (m, 1H), 3.72 (d, 1H), 3.67 (m, 1H), 3.48 (m, 1H), 3.26 (m, 2H), 2.47 (s, 3H), 1.42 (s, 9H).

Step B: Preparation of (5{4-[5-(3,5-dichloro-phenyl)-5-trifluoromethyl-4,5-dihydro-isoxazol-3-yl]-2-methyl-benzoylamino}-methyl-2-oxo-[1,2,3]oxathiazolidine-3-carboxylic acid carbamic acid tert-butyl ester

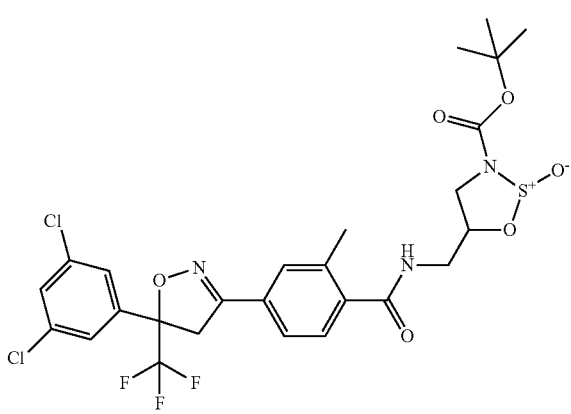 [SMILES: Cc1cc(C2=NOC(c3cc(Cl)cc(Cl)c3)(C(F)(F)F)C2)ccc1C(=O)NCC1CN(C(=O)OC(C)(C)C)[S+]([O-])O1]

A solution of (3{4-[5-(3,5-dichloro-phenyl)-5-trifluoromethyl-4,5-dihydro-isoxazol-3-yl]-2-methyl-benzoylamino}-2-hydroxy-propyl)-carbamic acid tert-butyl ester (150 mg) in dichloromenthane (10 ml) was cooled to 0° C., treated with pyridine (0.16 ml) and thionyl chloride (0.04 ml) and stirred for 2 hours. The mixture was diluted with dichloromenthane (50 ml), neutralized with 2N hydrochloric acid and washed with water (50 ml). The organic layer was separated, dried over sodium sulfate and concentrated. Purification by chromatography on silica gel (eluent hexane/ethyl acetate 40:60) gave the title compound (50 mg). LCMS (Method G) 4.29 min, MH+ 636. $^1$HNMR (CDCl$_3$, 400 MHz): 7.13-7.59 (m, 6H), 5.15 (m, 1H), 5.45 (m, 1H), 3.94-4.23 (m, 3H), 3.72 (m, 2H), 3.40 (m, 1H), 2.45 (s, 3H), 1.51 (s, 9H).

EXAMPLE 33

Preparation of 4-[5-(3,5-Dichloro-phenyl)-5-trifluoromethyl-4,5-dihydro-isoxazol-3-yl]-2-methyl-N-(2-oxo-[1,2,3]oxathiazolidin-5-ylmethyl)-benzamide (Compound F9)

Step A: Preparation of N-(3-amino-2-hydroxy-propyl)-4-[5-(3,5-dichloro-phenyl)-5-trifluoromethyl-4,5-dihydro-isoxazol-3-yl]-2-methyl-benzamide

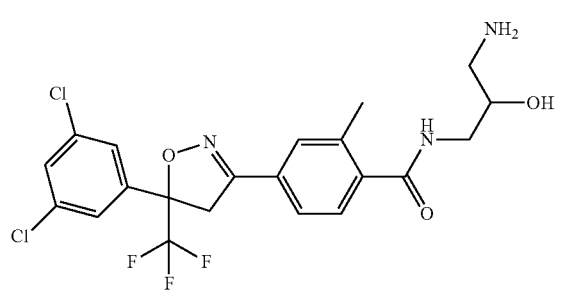 [SMILES: Cc1cc(C2=NOC(c3cc(Cl)cc(Cl)c3)(C(F)(F)F)C2)ccc1C(=O)NCC(O)CN]

A solution of (3{4-[5-(3,5-dichloro-phenyl)-5-trifluoromethyl-4,5-dihydro-isoxazol-3-yl]-2-methyl-benzoylamino}-2-hydroxy-propyl)-carbamic acid tert-butyl ester (0.2 g) in dichloromethane (10 ml) was cooled to 0° C., treated with trifluoroacetic acid (0.5 ml) and stirred for 10 h. The reaction mixture was concentrated in vacuo and diluted with dichloromethane (50 ml), washed with saturated aqueous solution of sodium bicarbonate (20 ml) and finally with water (2×20 ml). The organic layer was separated, dried over sodium sulfate and concentrated to give the title compound (0.13 g). LCMS (Method G) 2.84 min, MH+ 490. $^1$HNMR (CDCl$_3$, 400 MHz): 8.05 (t, 1H), 7.81 (m, 1H), 7.80 (brs, 2H), 7.59 (m, 4H), 7.48 (d, 1H), 4.36 (dd, 2H), 3.85 (m, 2H), 3.28 (m, 2H), 2.50 (m, 1H), 2.37 (s, 3H).

Step B: Preparation of 4-[5-(3,5-Dichloro-phenyl)-5-trifluoromethyl-4,5-dihydro-isoxazol-3-yl]-2-methyl-N-(2-oxo-[1,2,3]oxathiazolidin-5-ylmethyl)-benzamide

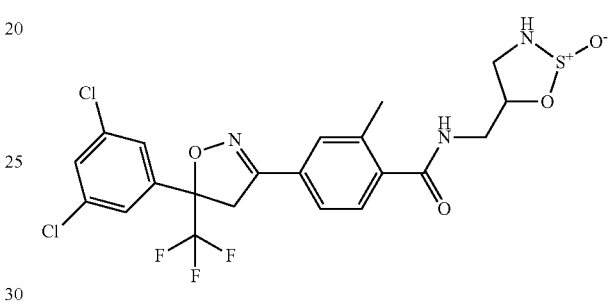

A solution of N-(3-amino-2-hydroxy-propyl)-4-[5-(3,5-dichloro-phenyl)-5-trifluoromethyl-4,5-dihydro-isoxazol-3-yl]-2-methyl-benzamide (0.2 g) in dichloromethane (10 ml) was cooled to 0° C., treated with pyridine (0.32 ml) and thionyl chloride (0.06 ml), and stirred for 4 hours. The mixture was diluted with dichloromethane (50 ml), neutralized with 2N hydrochloric acid, and washed with water (50 ml). The organic layer was separated, dried over sodium sulfate and concentrated. Purification by chromatography on silica gel (eluent hexane/ethyl acetate 40:60) gave the title compound (20 mg). LCMS (Method G) 3.88 min, (M–H)− 534. $^1$HNMR (CDCl$_3$, 400 MHz): 7.45-7.52 (m, 6H), 6.50 (m, 1H), 4.05 (d, 1H), 3.98 (m, 1H), 3.72 (d, 1H), 3.62 (m, 1H), 3.51 (m, 3H), 2.46 (s, 3H).

EXAMPLE 34

Preparation of 4-[5-(3,5-dichloro-phenyl)-5-methyl-4,5-dihydro-isoxazol-3-yl]-N-(1-methyl-3-oxo-pyrazolodin-4-yl)-benzamide (Compound A4)

Step A: Preparation of 4-amino-1-methyl-pyrazolidin-3-one

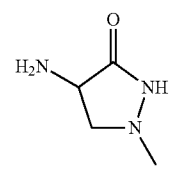

A solution of 4-benzyloxycarbonylamino-1-methyl-pyrazolidin-3-one (240 mg, 1 mmol) (Tetrahedron 1998, 44(1), 3231-3240) in methanol (50 ml) was treated with 10% Pd/C (24 mg) and hydrogenated at 3 bar pressure for 3 hours. The suspension was filtered through Celite and the filtrate was concentrated under reduced pressure to give the title compound (110 mg). LCMS (Method G) 0.42 min, (M−H)+ 116. ¹HNMR (MeOD, 400 MHz): 2.96 (t, 1H), 3.00 (s, 3H), 3.55 (m, 1H), 3.72 (t, 1H), 3.85 (bs, 2H).

Step B: Preparation of 4-[5-(3,5-dichloro-phenyl)-5-methyl-4,5-dihydro-isoxazol-3-yl]-N-(1-methyl-3-oxo-pyrazolodin-4-yl)-benzamide

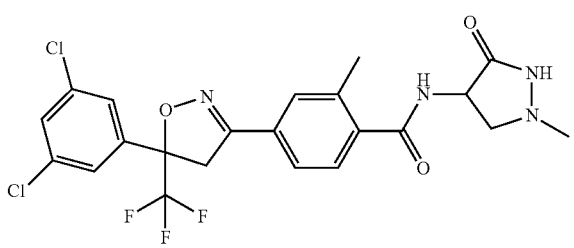 [SMILES: Cc1cc(C2=NOC(c3cc(Cl)cc(Cl)c3)(C(F)(F)F)C2)ccc1C(=O)NC1CN(C)NC1=O]

Oxalyl chloride (0.18 ml) was added dropwise to a solution of 4-[5-(3,5-dichloro-phenyl)-5-methyl-4,5-dihydro-isoxazol-3-yl]-2-methylbenzoic acid (0.398 g) in dichloromethane (10 ml) and 1 drop of N,N-dimethylformamide and stirred at room temperature under nitrogen for 6 hours. The mixture was concentrated and the residue was dissolved in dichloromethane (30 ml), treated with a solution of 4-amino-1-methyl-pyrazolidin-3-one (0.11 g), a solution of triethylamine (0.5 ml) in tetrahydrofuran (20 ml), and stirred for 16 hours under nitrogen. The reaction mixture was concentrated and purified by chromatography on silica gel (eluent hexane/ethyl acetate 60:40) to give 4-[5-(3,5-dichloro-phenyl)-5-methyl-4,5-dihydro-isoxazol-3-yl]-N-(1-methyl-3-oxo-pyrazolodin-4-yl)-benzamide as a solid compound which is a mixture of diasteromers (5 mg). ¹HNMR (CDCl₃): 2.42 (s, 3H), 3.01 (s, 3H), 3.55 (t, 1H), 3.71 (dd, 2H), 3.86 (m, 1H), 4.08 (dd, 1H), 5.13 (m, 1H), 6.29 (br. d, 1H), 7.4-7.6 (m, 6H).

EXAMPLE 35

Preparation of Compounds of the Invention in Parallel

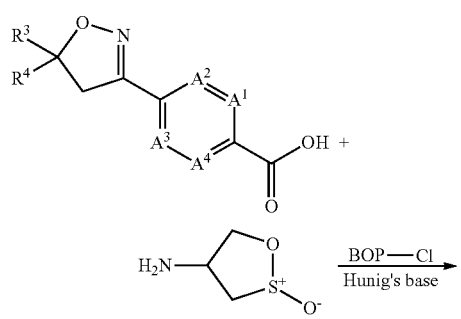

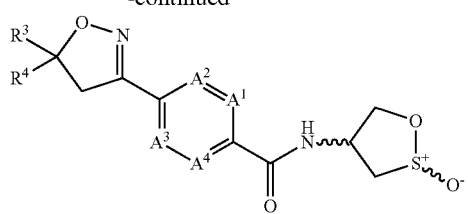

Following the general procedure described in Example 18, several compounds of formula (Ij) were prepared in parallel (compounds J1-J32 in Table J). Two diastereoisomers were separated in each case, named A and B in Table J.

EXAMPLE 36

Preparation of 4-[3-(3,5-dichloro-phenyl)-4,4,4-trifluoro-but-2-enoyl]-N-((R)-2-ethyl-3-oxo-isoxazolidin-4-yl)-2-methyl-benzamide Step A: 4-Acetyl-N-((R)-2-ethyl-3-oxo-isoxazolidin-4-yl)-2-methyl-benzamide

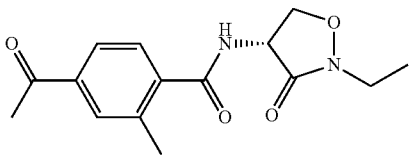 [SMILES: CCN1OC[C@@H](NC(=O)c2ccc(C(C)=O)cc2C)C1=O]

To a suspension of 4-acetyl-2-methyl-benzoic acid (1 g, prepared as described in WO2009001942) in dichloromethane (200 ml) and dimethylformamide (0.2 ml) under argon atmosphere at room temperature, was added dropwise oxalyl chloride (0.53 ml) then the resulting mixture was stirred 1 hour at room temperature until the solid was dissolved. The solvent was removed in vacuo to afford crude 4-acetyl-2-methyl-benzoic acid chloride. To a solution of (R)-4-amino-2-ethyl-isoxazolidin-3-one (1.64 g, Example 4, Step B) in dry dichloromethane (10 ml) was added dropwise at room temperature triethylamine (5 ml). The solution of acid chloride in dichloromethane (5 ml) was added dropwise at room temperature. The resulting mixture was allowed to stir 4 hours at room temperature, then quenched with water. The organic phase was washed with 1N aqueous hydrochloric acid solution. The organic layer was dried over sodium sulphate and the solvent was removed under reduced pressure to afford a residue, which was purified by crystallization from diethyl ether to give a beige solid (1 g). LCMS (Method A) 1.23 min, (M+H)+ 291. Chiral HPLC (method H) 30.18 min (98.99%), 33.62 min (1.01%). ¹HNMR (CDCl3, 400 MHz):

1.20 (t, 3H), 2.50 (s, 3H), 2.60 (s, 3H), 3.65 (m, 2H), 4.05 (m, 1H), 4.85 (m, 1H), 5.0 (t, 1H), 6.45 (bs, 1H), 7.50 (d, 1H), 7.70-7.90 (m, 2H).

Step B: 4-[3-(3,5-dichloro-phenyl)-4,4,4-trifluoro-but-2-enoyl]-N-((R)-2-ethyl-3-oxo-isoxazolidin-4-yl)-2-methyl-benzamide

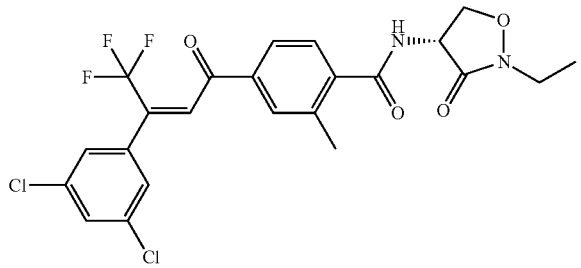 [SMILES: CCN1OC[C@@H](NC(=O)c2ccc(C(=O)/C=C(/c3cc(Cl)cc(Cl)c3)C(F)(F)F)cc2C)C1=O]

To a solution of 4-Acetyl-N-((R)-2-ethyl-3-oxo-isoxazolidin-4-yl)-2-methyl-benzamide (1 g) in 1,2-dichloroethane (5 ml) were added 3,5 dichloro 2,2,2 trifluoroacetophenon (0.92 g), potassium carbonate (0.48 g), and triethylamine (35 mg). The mixture was heated at 100° C. overnight, cooled to room temperature, then partitioned between ethyl acetate and water. The aqueous layer was extracted twice with ethyl acetate and the combined organic layers were dried over sodium sulphate and the solvents removed in vacuo. The residue was purified by column chromatography (ethyl acetate/cyclohexane) to obtain the title compound as a yellow solid (1 g). LCMS (Method A) 2.02 min, (M+H)$^+$ 515/517. $^1$HNMR (CDCl$_3$, 400 MHz): 83:17 mixture of diastereoisomers ((E) and (Z)). Major isomer: 1.25 (t, 3H), 2.50 (s, 3H), 3.70 (m, 2H), 4.05 (m, 1H), 4.85 (m, 1H), 5.0 (t, 1H), 6.35 (bd, 1H), 7.15-7.65 (m, 6H), Minor isomer: 1.25 (t, 3H), 2.55 (s, 3H), 3.70 (m, 2H), 4.05 (m, 1H), 4.85 (m, 1H), 5.0 (t, 1H), 6.40 (bd, 1H), 7.15-7.65 (m, 6H).

EXAMPLE 37

Asymmetric preparation of 4-[5-(3,5-dichloro-phenyl)-5-trifluoromethyl-4,5-dihydro-isoxazol-3-yl]-2-methyl-N-((R)-2-ethyl-3-oxo-isoxazolidin-4-yl)-benzamide Step A: Catalyst preparation:
2,3,4,5,6-pentafluorophenyl-methyl quininium bromide

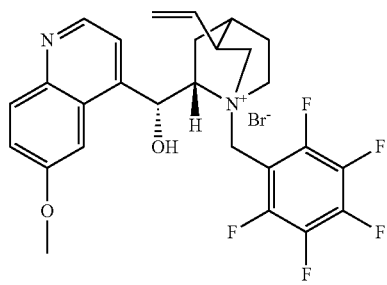 [SMILES: C=CC1C[N+]2(Cc3c(F)c(F)c(F)c(F)c3F)CCC1C[C@H]2[C@H](O)c1ccnc2ccc(OC)cc12 ; [Br-]]

A solution of 1-bromomethyl-2,3,4,5,6-pentafluorobenzene (0.52 g) and quinine (0.5 g) in toluene (9 ml) was heated at 80° C. for 18 hours. The reaction mixture was poured in diethyl ether and then filtrate to afford the title product as a white solid (0.90 g). M.p. 162-165° C. (decomposed). LCMS (method G) 1.08 min, M$^+$505; $^1$H NMR (400 MHz, CDCl$_3$) 8.78 (d, 1H), 8.05 (d, 1H), 7.78 (d, 1H), 7.39 (dd, 1H), 7.18 (d, 1H), 6.73 (m, 1H), 6.41 (d, 1H), 6.09 (d, 1H), 5.50 (m, 1H), 5.04 (d, 1H), 4.98 (d, 1H), 4.70 (m, 1H), 4.63 (d, 1H), 3.98 (s, 3H), 3.97 (m, 1H), 3.74 (m, 2H), 3.10 (m, 1H), 2.81 (m, 1H), 2.30 (m, 2H), 2.05 (m, 2H), 1.41 (m, 1H). $^{19}$F NMR (376 MHz, CDCl$_3$)-132.67 (s, 1F), -146.60 (s, 2F), -158.28 (s, 2F).

Similarly were prepared the two catalysts 3,4,5-trimethoxybenzyl quininium bromide and anthracenyl-methyl dihydroquininium bromide.

Step B: 4-[5-(3,5-Dichloro-phenyl)-5-trifluoromethyl-4,5-dihydro-isoxazol-3-yl]-2-methyl-N-(2-ethyl-3-oxo-isoxazolidin-4-yl)-benzamide

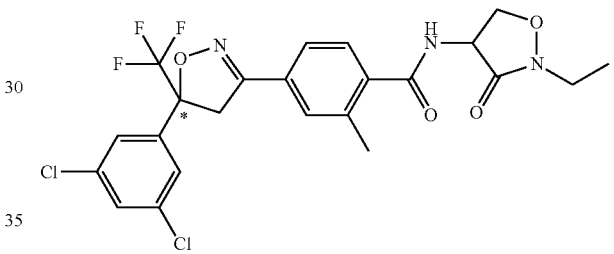

A pre-cooled solution of 5M sodium hydroxide (0.09 ml) was added to a solution of hydroxylamine (50% in water, 0.024 ml) at 5° C. (ice bath). The solution was stirred for 15 min at 5° C. then added to a vigorously stirred solution of 4-[3-(3,5-dichloro-phenyl)-4,4,4-trifluoro-but-2-enoyl]-N-((R)-2-ethyl-3-oxo-isoxazolidin-4-yl)-2-methyl-benzamide (100 mg) and anthracenyl-methyl quininium bromide (20 mg) (Step A) in dichloroethane (1 ml) cooled in an ice-acetone bath. The mixture was stirred rapidly at 0° C. for 4 hours. The reaction mixture was diluted with dichloromethane, passed through an isolute phase separating cartridge and concentrated in vacuo to leave yellow oil. This residue was purified by chromatography on silica gel (eluent: heptane/ethyl acetate 5%) to give the title compound (9 mg). The product was analysed by chiral HPLC (method H): 18.7 min (42.5%), 19.6 min (24.2%), 21.4 min (8.5%), 22.8 min (24.8%).

Similarly, using 3,4,5-trimethoxybenzyl quininium bromide as a catalyst, the following ratio of isomers was obtained (38 mg): 18.5 min (14.9%), 19.5 min (35.9%), 21.2 min (12.5%), 22.7 min (36.7%).

Similarly, using 2,3,4,5,6-pentafluorophenyl-methyl quininium bromide as a catalyst, the following ratio of isomers was obtained (23 mg): 18.6 min (16.8%), 19.6 min (38.0%), 21.3 min (9.2%), 22.7 min (36.0%).

TABLE A

Compounds of formula (Ia):

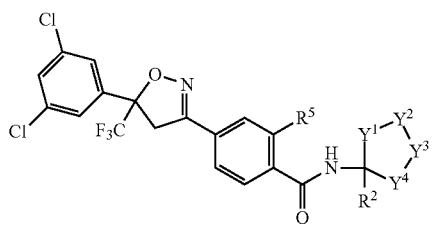

(Ia)

| Comp. No. | R⁵ | Y¹ | Y² | Y³ | Y⁴ | R² | LCMS Method | RT (min) | mass spectrum |
|---|---|---|---|---|---|---|---|---|---|
| A1 | Me | CH₂ | S | S | CH₂ | H | F | 2.20 | 519/521 |
| A2 | Me | CH₂ | S(O) | O | CH₂ | H | F | 2.04 | 519/521 |
| A3 | Me | CH₂ | O | N—Et | CH₂ | H | E | 2.02 | 516/518 |
| A4 | Me | CH₂ | N—Me | N—H | C(O) | H | NMR | see Example 34 | |

TABLE B

Compounds of formula (Ib):

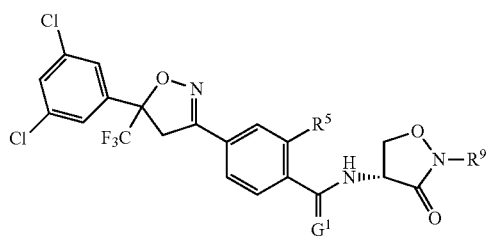

(Ib)

| Comp No. | R⁵ | G¹ | R⁹ | LCMS Method | RT (min) | mass spectrum |
|---|---|---|---|---|---|---|
| B1 | Me | O | H | F | 1.99 | 500/502 |
| B2 | Me | O | CH₃ | A | 1.99 | 516/518 |
| B3 | Me | O | propargyl | A | 2.06 | 538/540 |
| B4 | Me | O | benzyl | F | 2.17 | 590/592 |
| B5 | Me | O | 2,2,2-trifluoroethyl | F | 2.11 | 582/584 |
| B6 | Me | O | CH₂CH₃ | F | 2.05 | 528/530 |
| B7 | Me | O | 2-methoxyethyl | F | 2.02 | 558/560 |
| B8 | Me | O | n-butyl | F | 2.14 | 556/558 |
| B9 | Me | O | 2-hydroxyethyl | F | 1.94 | 544/546 |
| B10 | Me | O | thietan-3yl | F | 2.13 | 572/574 |
| B11 | Me | O | cyclobutyl | F | 2.16 | 554/556 |
| B12 | Me | O | oxetan-3yl | F | 2.06 | 556/558 |
| B13 | Me | O | 3-methyl-but-2-enyl | J | 2.04 | 570.29 |
| B14 | Me | O | 4-nitro-benzyl | J | 1.90 | 637.28 |
| B15 | Me | O | 1,1,1-trifluoropropan-3-yl | J | 1.96 | 598.24 |
| B16 | Me | O | 4-fluoro-benzyl | J | 2.04 | 610.27 |
| B17 | Me | O | 1,1,1-trifluorobutan-4-yl | J | 2.01 | 612.27 |
| B18 | Me | O | 2-cyanoethyl | J | 1.80 | 555.24 |
| B19 | Me | O | 2,6-difluoro-benzyl | J | 2.04 | 628.29 |
| B20 | Me | O | cyclopropylmethyl | J | 1.95 | 556.3 |
| B21 | Me | O | 2-[1,3]dioxan-2-yl-ethyl | J | 1.88 | 616.3 |
| B22 | Me | O | 5-trifluoromethyl-furan-2-yl methyl | J | 2.07 | 650.24 |
| B23 | Me | O | 2,5-dimethyl-2H-[1,2,3]triazol-4-yl methyl | J | 1.85 | 611.32 |
| B24 | Me | O | cyclobutylmethyl | J | 2.05 | 570.29 |
| B25 | Me | O | 3-cyanopropyl | J | 1.82 | 569.27 |
| B26 | Me | O | tetrahydro-pyran-2-ylmethyl | J | 1.96 | 600.33 |
| B27 | Me | O | 3-phenyl-propyl | J | 2.14 | 620.33 |
| B28 | Me | O | but-2-ynyl | J | 1.92 | 554.25 |
| B29 | Me | O | cyclohexylmethyl | J | 2.18 | 598.34 |
| B30 | Me | O | (propan-2-one O-methyl-oxime)-1-yl | J | 1.93 | 587.26 |

TABLE C

Compounds of formula (Ic):

(Ic)

| Comp No. | R⁴ | A³ | R⁹ | LCMS Method | RT (min) | mass spectrum |
|---|---|---|---|---|---|---|
| C1 | 3,4,5-trichloro-phenyl | CH | ethyl | F | 2.09 | 562/564/566 |
| C2 | 3,5-dichloro-4-bromo-phenyl | CH | ethyl | F | 2.09 | 605/607/609 |
| C3 | 3,5-dichloro-4-fluoro-phenyl | CH | ethyl | F | 2.04 | 546/548 |
| C4 | 3,5-trifluoro-methyl-4-chloro-phenyl | CH | ethyl | F | 2.15 | 630/632 |
| C5 | 3-chloro-5-fluoro-phenyl | CH | ethyl | F | 1.99 | 512/514 |
| C6 | 3,5-dichloro-phenyl | N | 2,2,2-trifluoro-ethyl | F | 2.13 | 583/585 |
| C7 | 3,5-dichlorophenyl | N | ethyl | F | 2.03 | 529/531 |
| C8 | 3,4,5-trichloro-phenyl | CH | 2,2,2-trifluoro-ethyl | F | 2.18 | 616/618/620 |
| C9 | 3,5-dichloro-4-fluoro-phenyl | CH | 2,2,2-trifluoro-ethyl | F | 2.13 | 600/602 |

TABLE D

Compounds of formula (Id):

(Id)

| Comp No. | R⁴ | R⁹ | LCMS Method | RT (min) | mass spectrum |
|---|---|---|---|---|---|
| D1 | 3,5-trichloro-phenyl | ethyl | D | 2.21 | 578/580 |

TABLE E

Compounds of formula (Ie):

(Ie)

| Comp No. | R⁵ | G¹ | R⁹ | LCMS Method | RT (min) | mass spectrum |
|---|---|---|---|---|---|---|
| E1 | Me | O | CH₃ | F | 1.98 | 514/516 |
| E2 | Me | O | CH₂CH₃ | F | 2.06 | 528/530 |

TABLE F

Compounds of formula (If):

(If)

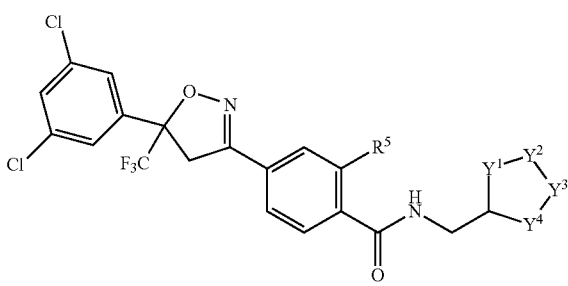

| Comp No. | R⁵ | Y¹ | Y² | Y³ | Y⁴ | LCMS Method | RT (min) | mass spectrum |
|---|---|---|---|---|---|---|---|---|
| F1 | Me | CH₂ | CH₂ | N—CH₂Ph | O | F | 2.20 | 590/591 |
| F2 | Me | CH₂ | CH₂ | N—CH₃ | O | F | 1.80 | 514/516 |
| F3 | Me | CH₂ | C(O) | N—CH₂CH₃ | O | F | 2.02 | 542/544 |
| F4 | Me | CH₂ | C(O) | N—CH₂CF₃ | O | F | 2.11 | 596/598 |
| F5 | Me | CH₂ | O | S(O) | O | G | 4.07 | 536 |
| F6 | Me | CH₂ | CH₂ | N-(4-methoxy-phenyl) | SO₂ | F | 2.02 | 654/655 |
| F7 | Me | CH₂ | CH₂ | N-(2,2,2-trifluoro-ethyl) | SO₂ | F | 2.41 | 630/632 |
| F8 | Me | CH₂ | N—COOtBu | S(O) | O | G | 4.29 | 636 |
| F9 | Me | CH₂ | NH | S(O) | O | G | 3.88 | 534 |

TABLE G

Compounds of formula (Ig):

(Ig)

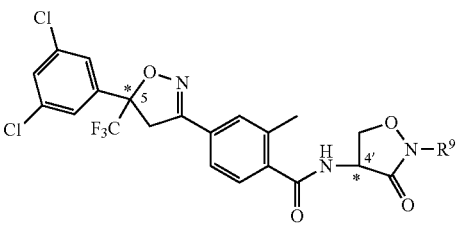

| Comp No. | Stereochemistry at C-5 | Stereochemistry at C-4' | R⁹ | HPLC Method | RT (min) | mass spectrum |
|---|---|---|---|---|---|---|
| G1 | (S) | (R) | ethyl | H | 21.3 | — |
| G2 | (R) | (R) | ethyl | H | 19.8 | — |
| G3 | (S) | (S) | ethyl | H | 21.1 | — |
| G4 | (R) | (S) | ethyl | H | 17.1 | — |
| G5 | (S) | (R) | 2,2,2-trifluoro-ethyl | F | 2.25 | 582/584 |
| G6 | (S) | (R) | 2,2-difluoro-ethyl | F | 2.09 | 564/566 |

TABLE H

Compounds of formula (Ih):

(Ih)

| Comp No. | A²–A¹ / A³–A⁴ | R⁴ | R³ | R⁹ | LCMS Method | RT (min) | MH⁺ |
|---|---|---|---|---|---|---|---|
| H1 | methylphenyl | 3-(trifluoromethoxy)phenyl | CF₃ | CH₂CH₃ | J | 1.78 | 546.31 |
| H2 | methylpyridinyl | 3,5-dichlorophenyl | CF₃ | CH₂CH₃ | J | 1.85 | 530.64 |
| H3 | quinolinyl | 3,5-dichlorophenyl | CF₃ | CH₂CH₃ | J | 1.92 | 567.25 |
| H4 | pyridinyl | 3,5-dichlorophenyl | CF₃ | CH₂CH₃ | J | 1.85 | 517.24 |
| H5 | cyclopropylphenyl | 3,5-dichlorophenyl | CF₃ | CH₂CH₃ | J | 1.94 | 556.27 |
| H6 | methylphenyl | 2,6-dichloro-4-cyanophenyl | CF₃ | CH₂CH₃ | J | 1.75 | 555.26 |
| H7 | isoquinolinyl | 3,5-dichlorophenyl | CF₃ | CH₂CH₃ | J | 2 | 567.25 |

TABLE H-continued
Compounds of formula (Ih):
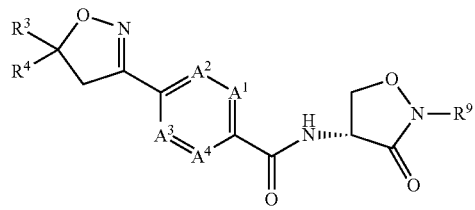
(Ih)
| Comp No. | A²-A¹ / A³-A⁴ | R⁴ | R³ | R⁹ | LCMS Method | RT (min) | MH⁺ |
|---|---|---|---|---|---|---|---|
| H8 | | 3,5-diCl-phenyl | CF₃ | CH₂CH₃ | J | 1.82 | 516.26 |
| H9 | 2-Br-phenyl | 3,5-diCl-phenyl | CF₃ | CH₂CH₃ | J | 1.9 | 594.14 |
| H10 | naphthyl | 3,5-diCl-phenyl | CF₃ | CH₂CH₃ | J | 1.97 | 566.27 |
| H11 | 2-CH₃-phenyl | 3-Cl-5-CF₃-phenyl | CF₃ | CH₂CH₃ | J | 1.89 | 564.28 |
| H12 | 2-CH₃-phenyl | 3-Br-5-Cl-phenyl | CF₃ | CH₂CH₃ | J | 1.89 | 574.19 |
| H13 | 2-CH₃-phenyl | 3,5-diCl-phenyl | CClF₂ | CH₂CH₃ | J | 1.9 | 546.23 |
| H14 | 2-CH₃-phenyl | 3-OCF₃-phenyl | CF₃ | CH₂CF₃ | J | 1.95 | 677.26 |

TABLE H-continued

Compounds of formula (Ih):

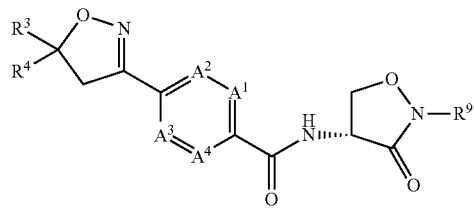

(Ih)

| Comp No. | ![A ring] | R⁴ | R³ | R⁹ | LCMS Method | RT (min) | MH⁺ |
|---|---|---|---|---|---|---|---|
| H15 | 2-methylpyridin-3,6-diyl | 3,5-dichlorophenyl | CF₃ | CH₂CF₃ | J | 1.88 | 600.28 |
| H16 | quinolin-5,8-diyl | 3,5-dichlorophenyl | CF₃ | CH₂CF₃ | J | 1.95 | 585.24 |
| H17 | pyridin-2,5-diyl | 3,5-dichlorophenyl | CF₃ | CH₂CF₃ | J | 2.02 | 621.25 |
| H18 | 2-cyclopropylphenyl | 3,5-dichlorophenyl | CF₃ | CH₂CF₃ | J | 1.95 | 571.22 |
| H19 | 2-methylphenyl | 2,6-dichloro-4-cyanophenyl | CF₃ | CH₂CF₃ | J | 2.03 | 610.25 |
| H20 | isoquinolin-1,4-diyl | 3,5-dichlorophenyl | CF₃ | CH₂CF₃ | J | 1.85 | 609.21 |
| H21 | phenyl | 3,5-dichlorophenyl | CF₃ | CH₂CF₃ | J | 1.93 | 569.83 |

TABLE H-continued
Compounds of formula (Ih):
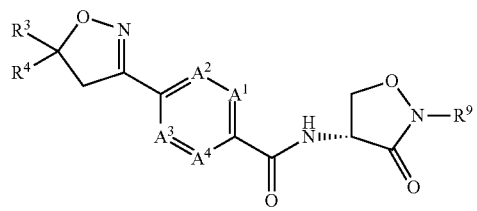
(Ih)
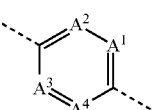
| Comp No. | (ring) | R⁴ | R³ | R⁹ | LCMS Method | RT (min) | MH⁺ |
|---|---|---|---|---|---|---|---|
| H22 | 2-Br-phenyl | 3,5-diCl-phenyl | $CF_3$ | $CH_2CF_3$ | J | 1.99 | 648.15 |
| H23 | naphthyl | 3,5-diCl-phenyl | $CF_3$ | $CH_2CF_3$ | J | 2.05 | 620.25 |
| H24 | 2-methyl-phenyl | 3-Cl-5-$CF_3$-phenyl | $CF_3$ | $CH_2CF_3$ | J | 1.98 | 618.26 |
| H25 | 2-methyl-phenyl | 3-Br-5-Cl-phenyl | $CF_3$ | $CH_2CF_3$ | J | 1.98 | 628.2 |
| H26 | 2-methyl-phenyl | 3,5-diCl-phenyl | $CClF_2$ | $CH_2CF_3$ | J | 2 | 600.22 |

TABLE J

Compounds of formula (Ij):

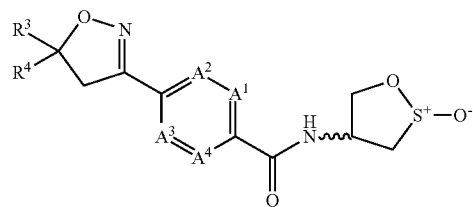

| Comp No. | A²–A¹ / A³–A⁴ | R⁴ | R³ | Diastereoisomer | LCMS Method | RT (min) | MH⁺ |
|---|---|---|---|---|---|---|---|
| J1 | 2-methylphenyl | 3,5-dichlorophenyl | CClF₂ | A | J | 1.82 | 537.23 |
| J2 | 2-methylphenyl | 3,5-dichlorophenyl | CClF₂ | B | J | 1.88 | 537.14 |
| J3 | 2-methylphenyl | 2,3-dichlorophenyl | CF₃ | A | J | 1.9 | 555.13 |
| J4 | 2-methylphenyl | 2,3-dichlorophenyl | CF₃ | B | J | 1.95 | 555.15 |
| J5 | 2-methylphenyl | 3-chloro-5-CF₃-phenyl | CF₃ | A | J | 1.82 | 555.22 |
| J6 | 2-methylphenyl | 3-chloro-5-CF₃-phenyl | CF₃ | B | J | 1.86 | 555.22 |
| J7 | 2-methylphenyl | 2-bromo-3,5-dichlorophenyl | CF₃ | A | J | 1.91 | 599.13 |

TABLE J-continued

Compounds of formula (Ij):

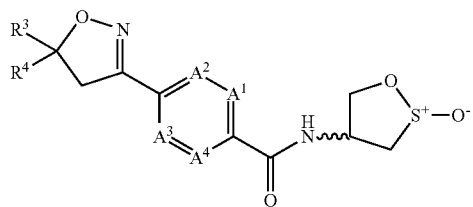

(Ij)

| Comp No. | $\begin{array}{c}A^2\phantom{0}A^1\\A^3\phantom{0}A^4\end{array}$ | R⁴ | R³ | Diatereoisomer | LCMS Method | RT (min) | MH⁺ |
|---|---|---|---|---|---|---|---|
| J8 | 2-methylphenyl | 2-Br-3,5-diCl-phenyl | CF₃ | B | J | 1.95 | 599.17 |
| J9 | 2-methylphenyl | 2-I-3,5-diCl-phenyl | CF₃ | A | J | 1.9 | 647.07 |
| J10 | 2-methylphenyl | 2-I-3,5-diCl-phenyl | CF₃ | B | J | 1.95 | 647.09 |
| J11 | 2-methylphenyl | 3-Br-5-Cl-phenyl | CF₃ | A | J | 1.82 | 565.14 |
| J12 | 2-methylphenyl | 3-Br-5-Cl-phenyl | CF₃ | B | J | 1.86 | 565.14 |
| J13 | 2-methylphenyl | 2-F-3,5-diCl-phenyl | CF₃ | A | J | 1.82 | 539.19 |
| J14 | 2-methylphenyl | 2-F-3,5-diCl-phenyl | CF₃ | B | J | 1.86 | 539.16 |

TABLE J-continued

Compounds of formula (Ij):

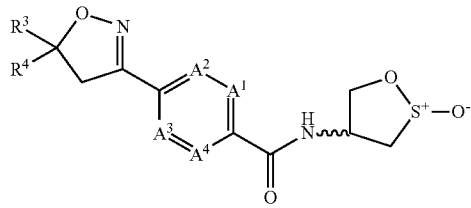

(Ij)

| Comp No. | A²⟨⟩A¹ / A³⟨⟩A⁴ | R⁴ | R³ | Diatereoisomer | LCMS Method | RT (min) | MH⁺ |
|---|---|---|---|---|---|---|---|
| J15 | 4-methyl-pyridin-3,5-diyl | 3,5-dichlorophenyl | $CF_3$ | A | J | 1.75 | 522.19 |
| J16 | 4-methyl-pyridin-2,5-diyl | 3,5-dichlorophenyl | $CF_3$ | B | J | 1.78 | 522.19 |
| J17 | 2-bromophenyl | 3,5-dichlorophenyl | $CF_3$ | A | J | 1.82 | 585.12 |
| J18 | 2-bromophenyl | 3,5-dichlorophenyl | $CF_3$ | B | J | 1.87 | 585.09 |
| J19 | naphthalen-1,4-diyl | 3,5-dichlorophenyl | $CF_3$ | A | J | 1.9 | 557.15 |
| J20 | naphthalen-1,4-diyl | 3,5-dichlorophenyl | $CF_3$ | B | J | 1.94 | 557.2 |
| J21 | 2-cyclopropyl-pyridin-diyl | 3,5-dichlorophenyl | $CF_3$ | A | J | 1.86 | 547.21 |

TABLE J-continued

Compounds of formula (Ij):

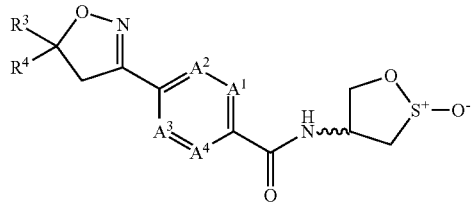

| Comp No. | A² A¹ / A³ A⁴ | R⁴ | R³ | Diatereoisomer | LCMS Method | RT (min) | MH⁺ |
|---|---|---|---|---|---|---|---|
| J22 | 2-cyclopropylphenyl | 3,5-dichlorophenyl | CF₃ | B | J | 1.92 | 547.2 |
| J23 | 2-methylphenyl | 2,6-dichloro-4-cyanophenyl | CF₃ | A | J | 1.68 | 546.18 |
| J24 | 2-methylphenyl | 2,6-dichloro-4-cyanophenyl | CF₃ | B | J | 1.72 | 546.18 |
| J25 | phenyl | 3,5-dichlorophenyl | CF₃ | A | J | 1.77 | 507.16 |
| J26 | phenyl | 3,5-dichlorophenyl | CF₃ | B | J | 1.81 | 507.15 |
| J27 | 2-methylphenyl | 3-(trifluoromethyl)phenyl | CF₃ | A | J | 1.66 | 521.26 |
| J28 | 2-methylphenyl | 3-(trifluoromethyl)phenyl | CF₃ | B | J | 1.71 | 520.72 |
| J29 | 2-methylphenyl | 3,5-bis(trifluoromethyl)phenyl | CF₃ | A | J | 1.85 | 589.24 |

TABLE J-continued

Compounds of formula (Ij):

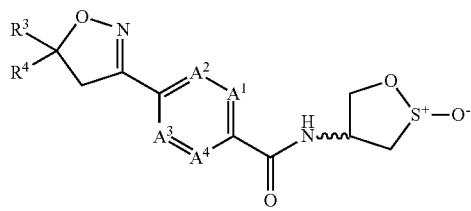

| Comp No. | A²,A¹/A³,A⁴ | R⁴ | R³ | Diatereoisomer | LCMS Method | RT (min) | MH⁺ |
|---|---|---|---|---|---|---|---|
| J30 | (2-methylphenyl) | 3,5-bis(CF₃)phenyl | CF₃ | B | J | 1.89 | 589.23 |
| J31 | (2-CF₃-phenyl) | 3,5-diCl-phenyl | CF₃ | A | J | 1.86 | 575.16 |
| J32 | (2-CF₃-phenyl) | 3,5-diCl-phenyl | CF₃ | B | J | 1.91 | 575.15 |

BIOLOGICAL EXAMPLES

This Example illustrates the pesticidal/insecticidal properties of compounds of formula (I). Tests were performed as follows:

*Spodoptera littoralis* (Egyptian cotton leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*:

A1, A3, B1, B2, B3, B4, B5, B6, B7, B8, B9, B10, B11, B12, C1, C2, C3, C4, C5, C6, C7, D1, E1, E2, F1, F2, F3, F4, F5, F6, G1, G3, G5, G6, H1, H2, H3, H5, H6, H7, H8, H9, H10, H11, H12, H13, H14, H15, H16, H18, H19, H20, H21, H22, H23, H24, H25, and H26.

*Heliothis virescens* (Tobacco budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*:

A1, A3, B1, B2, B3, B4, B5, B6, B7, B8, B9, B10, B12, C1, C2, C3, C4, C5, C6, C7, D1, E1, E2, F1, F2, F3, F4, F5, F6, G1, G3, G5, G6, H1, H2, H3, H5, H6, H7, H8, H9, H10, H11, H12, H13, H14, H15, H16, H18, H19, H20, H21, H22, H23, H24, H25, H26, J10, and J16.

*Plutella xylostella* (Diamond back moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*:

A1, A3, B1, B2, B3, B4, B5, B6, B7, B8, B9, B10, B11, B12, C1, C2, C3, C4, C5, C6, C7, D1, E1, E2, F1, F2, F3, F4, F5, F6, G1, G3, G5, G6, H1, H5, H6, H7, H8, H9, H10, H11, H12, H13, H14, H15, H16, H18, H19, H20, H21, H22, H23, H24, H25, H26, J1, J10, and J13.

*Diabrotica balteata* (Corn root worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*:

A1, A3, B2, B3, B4, B5, B6, B7, B8, B9, B10, B11, B12, C1, C2, C3, C4, C5, C6, C7, D1, E1, E2, F1, F2, F3, F4, F5, F6,

G1, G3, G5, G6, H1, H5, H6, H7, H8, H9, H10, H11, H12, H13, H14, H15, H16, H18, H19, H20, H21, H22, H23, H24, H25, H26, J4, and J20.

*Myzus persicae* (Green peach aphid), systemic test:

Roots of pea seedlings, infested with an aphid population of mixed ages, are placed directly in the test solutions at an application rate of 12.5 ppm. 6 days after introduction, samples are checked for mortality and special effects on the plant. The following compounds gave at least 80% control of *Myzus persicae*:

A3, B2, B3, B5, B6, B7, B8, B11, B12, C1, C2, C3, C4, C5, C6, C7, D1, E1, E2, G1, G3, G5, G6, H1, H5, H6, H9, H10, H11, H12, H13, H14, H18, H19, H20, H24, H25, and H26.

*Thrips tabaci* (Onion thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*:

A1, A3, B2, B3, B4, B5, B6, B7, B8, B9, B10, B11, B12, C1, C2, C3, C4, C5, C6, C7, D1, E1, E2, F1, F2, F3, F4, F5, G1, G3, G5, G6, H1, H2, H3, H5, H6, H7, H8, H9, H10, H11, H12, H13, H14, H15, H18, H19, H20, H21, H22, H23, H24, H25, H26, J3, J6, J8, J10, J19, and J20.

*Tetranychus urticae* (Two-spotted spider mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*:

A3, B1, B2, B3, B4, B5, B6, B7, B8, B9, B10, B11, B12, C1, C2, C3, C4, C5, C6, C7, D1, E1, E2, F1, F2, F3, F4, F5, F6, G1, G3, G5, G6, H1, H2, H5, H6, H7, H8, H9, H10, H11, H12, H13, H14, H15, H18, H19, H20, H21, H22, H23, H24, H25, and H26.

The invention claimed is:

1. A compound of formula (I):

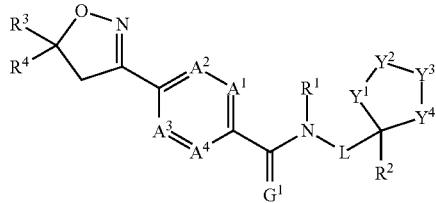

(I)

wherein
$A^1$, $A^2$, $A^3$ and $A^4$ are independently of one another C—H, C—$R^5$, or nitrogen;
$G^1$ is oxygen or sulfur;
L is a single bond or $C_1$-$C_8$alkylene;
$R^1$ is hydrogen, $C_1$-$C_8$alkyl, $C_1$-$C_8$alkylcarbonyl-, $C_1$-$C_8$alkoxy, $C_1$-$C_8$alkoxy-$C_1$-$C_8$alkyl, or $C_1$-$C_8$alkoxycarbonyl-;
$R^2$ is hydrogen, $C_1$-$C_8$haloalkyl or $C_1$-$C_8$alkyl;
$R^3$ is $C_1$-$C_8$haloalkyl;
$R^4$ is aryl or aryl substituted by one to three $R^6$, or $R^4$ is heterocyclyl or heterocyclyl substituted by one to three $R^6$;

each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH═CH—CH═CH— bridge or a —N═CH—CH═CH— bridge;
each $R^6$ is independently halogen, cyano, nitro, $C_1$-$C_8$alkyl, $C_1$-$C_8$haloalkyl, $C_1$-$C_8$alkoxy, or $C_1$-$C_8$-haloalkoxy;
$Y^1$ is $CR^7R^8$ is O, $Y^3$ is N-$R^9$ and $Y^4$ is C═O;
each $R^7$ and $R^8$ is independently hydrogen, halogen, $C_1$-$C_8$alkyl, or $C_1$-$C_8$haloalkyl;
each $R^9$ is independently hydrogen, cyano, cyano-$C_1$-$C_8$ alkyl, $C_1$-$C_8$ alkyl, $C_1$-$C_8$ haloalkyl, $C_3$-$C_8$cycloalkyl, $C_3$-$C_8$cycloalkyl where one carbon atom is replaced by O, S, S(O) or SO$_2$, or $C_3$-$C_8$ cycloalkyl-$C_1$-$C_8$ alkyl, $C_3$-$C_8$ cycloalkyl-$C_1$-$C_8$ alkyl where one carbon atom in the cycloalkyl group is replaced by O, S, S(O) or SO$_2$, or $C_3$-$C_8$cycloalkyl-$C_1$-$C_8$haloalkyl, $C_1$-$C_8$ hydroxyalkyl, $C_1$-$C_8$ alkoxy-$C_1$-$C_8$ alkyl, $C_2$-$C_8$alkenyl, $C_2$-$C_8$ haloalkenyl, $C_2$-$C_8$ alkynyl, $C_2$-$C_8$haloalkynyl, phenyl, phenyl substituted by one to three $R^{10}$, phenyl-$C_1$-$C_4$alkyl, phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$, or $C_1$-$C_4$ alkyl-($C_1$-$C_4$ alkyl-O—N═) C—CH$_2$—;
each $R^{10}$ is independently halogen, cyano, nitro, $C_1$-$C_8$ alkyl, $C_1$-$C_8$ haloalkyl, $C_1$-$C_8$ alkoxy, or $C_1$-$C_8$ haloalkoxy;
or a salt or N-oxide thereof.

2. A compound according to claim 1, wherein the compound is a compound of formula (Ia.E):

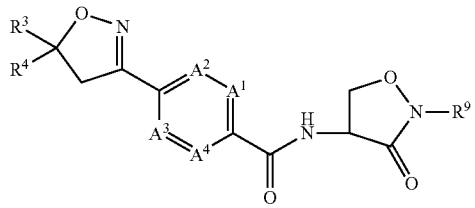

(Ia.E)

3. A compound according to claim 1, wherein $R^9$ is hydrogen, cyano-$C_1$-$C_8$alkyl, $C_1$-$C_8$alkyl, $C_3$-$C_8$cycloalkyl, $C_3$-$C_8$cycloalkyl where one carbon atom in the cycloalkyl group is replaced by O, S, S(O) or SO$_2$, or $C_1$-$C_8$haloalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^{10}$, 5-6 membered heteroaryl-$C_1$-$C_4$alkyl or 5-6 membered heteroaryl-$C_1$-$C_4$alkyl wherein the heteroaryl moiety is substituted by one to three $R^{10}$, and wherein the heteroaryl is pyridyl, pyridazinyl, pyrimidinyl, pyrazinyl, pyrazolyl, furanyl, thiophenyl, oxazolyl, isoxazolyl or thiazolyl.

4. A method of combating and/or controlling an invertebrate animal pest which comprises applying to the pest, to a locus of the pest, or to a plant susceptible to attack by the pest a pesticidally effective amount of a compound of formula (I) as defined in claim 1.

5. A composition comprising a pesticidally effective amount of a compound of formula (I) as defined in claim 1 optionally comprising an additional pesticidally active ingredient.

6. A combination product comprising a pesticidally effective amount of a component A and a pesticidally effective amount of component B, wherein component A is a compound of formula (I) as defined in claim 1, and compound B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

7. A compound according to claim 1, wherein $A^1$ is C—$R^5$, $A^2$ is C—H, $A^3$ is C—H, $A^4$ is C—H.

8. A compound according to claim 1, wherein $R^3$ is chlorodifluoromethyl or trifluoromethyl.

9. A compound according to claim 1, wherein $R^4$ is phenyl substituted by one to three $R^6$.

10. A compound according to claim 1, wherein $R^5$ is bromo, chloro, fluoro, cyclopropyl, vinyl, or methyl.

11. A compound according to claim 1, wherein each $R^6$ is independently chloro, fluoro, cyano, nitro, methyl, ethyl, trifluoromethyl, methoxy, or trifluoromethoxy.

12. A compound according to claim 1, wherein $R^9$ is hydrogen, $C_1$-$C_4$alkyl, $C_3$-$C_6$cyclo alkyl, $C_1$-$C_4$halo alkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^{10}$, furanyl or furanyl substituted by one to three $R^{10}$, thietanyl, oxetanyl, oxo-thietanyl, or dioxo-thietanyl.

13. A compound according to claim 1, wherein $R^9$ is methyl, ethyl, cyclopropyl, cyclobutyl, oxetanyl, thietanyl, trifluoroethyl, difluoroethyl, allyl, propargyl, cyanomethyl, benzyl, benzyl substituted by one to three $R^{10}$, or pyridine-methyl- or pyridine-methyl-substituted by one to three $R^{10}$.

14. A compound according to claim 1, wherein $R^9$ is ethyl or trifluoroethyl.

15. A compound according to claim 2, wherein
$A^1$ is C-$R^5$, $A^2$ is C-H, $A^3$ is C-H, $A^4$ is C-H;
$R^3$ is chlorodifluoromethyl or trifluoromethyl;
$R^4$ is phenyl substituted by one to three $R^6$;
$R^5$ is bromo, chloro, fluoro, cyclopropyl, vinyl, or methyl;
each $R^6$ is independently chloro, fluoro, cyano, nitro, methyl, ethyl, trifluoromethyl, methoxy, or trifluoromethoxy;
$R^9$ is ethyl or trifluoroethyl.

\* \* \* \* \*